US008318892B2

(12) United States Patent
Côté et al.

(10) Patent No.: US 8,318,892 B2
(45) Date of Patent: Nov. 27, 2012

(54) CAPPED STRUCTURED ORGANIC FILM COMPOSITIONS

(75) Inventors: Adrien P. Côté, Clarkson (CA); Matthew A. Heuft, Oakville (CA)

(73) Assignee: Xerox Corporation, Norwalk, CT (US)

( * ) Notice: Subject to any disclaimer, the term of this patent is extended or adjusted under 35 U.S.C. 154(b) by 88 days.

(21) Appl. No.: 12/845,053

(22) Filed: Jul. 28, 2010

(65) Prior Publication Data

US 2012/0029236 A1 Feb. 2, 2012

(51) Int. Cl.
*C08G 65/40* (2006.01)

(52) U.S. Cl. ............... 528/211; 252/182.12; 252/182.3; 257/40; 427/384; 427/542; 428/332

(58) Field of Classification Search ............ 252/182.12, 252/182.3; 257/40; 427/384, 542, 557; 428/332; 528/211
See application file for complete search history.

(56) References Cited

U.S. PATENT DOCUMENTS

| | | | |
|---|---|---|---|
| 2,324,550 A | 7/1943 | Wolfe | |
| 3,430,418 A | 3/1969 | Wagner | |
| 3,801,315 A | 4/1974 | Gundlach et al. | |
| 4,078,927 A | 3/1978 | Amidon et al. | |
| 4,081,274 A | 3/1978 | Horgan | |
| 4,115,116 A | 9/1978 | Stolka et al. | |
| 4,233,384 A | 11/1980 | Turner et al. | |
| 4,257,699 A | 3/1981 | Lentz | |
| 4,265,990 A | 5/1981 | Stolka et al. | |
| 4,286,033 A | 8/1981 | Neyhart et al. | |
| 4,291,110 A | 9/1981 | Lee | |
| 4,299,897 A | 11/1981 | Stolka et al. | |
| 4,304,829 A | 12/1981 | Limburg et al. | |
| 4,306,008 A | 12/1981 | Pai et al. | |
| 4,338,387 A | 7/1982 | Hewitt | |
| 4,387,980 A | 6/1983 | Ueno et al. | |
| 4,457,994 A | 7/1984 | Pai et al. | |
| 4,464,450 A | 8/1984 | Teuscher | |
| 4,489,593 A | 12/1984 | Pieters et al. | |
| 4,493,550 A | 1/1985 | Takekida | |
| 4,664,995 A | 5/1987 | Horgan et al. | |
| 4,855,203 A | 8/1989 | Badesha et al. | |
| 4,871,634 A | 10/1989 | Limburg et al. | |
| 4,917,711 A | 4/1990 | Xie et al. | |
| 4,921,769 A | 5/1990 | Yuh et al. | |
| 4,921,773 A | 5/1990 | Melnyk et al. | |
| 5,017,432 A | 5/1991 | Eddy et al. | |
| 5,061,965 A | 10/1991 | Ferguson et al. | |
| 5,110,693 A | 5/1992 | Friend et al. | |
| 5,139,910 A | 8/1992 | Law et al. | |
| 5,165,909 A | 11/1992 | Tennent et al. | |
| 5,166,031 A | 11/1992 | Badesha et al. | |
| 5,281,506 A | 1/1994 | Badesha et al. | |
| 5,300,271 A | 4/1994 | Golden et al. | |
| 5,366,772 A | 11/1994 | Badesha et al. | |
| 5,368,913 A | 11/1994 | Ortega | |
| 5,368,967 A | 11/1994 | Schank et al. | |
| 5,370,931 A | 12/1994 | Fratangelo et al. | |
| 5,432,539 A | 7/1995 | Anderson | |
| 5,455,136 A | 10/1995 | Yu et al. | |
| 5,456,897 A | 10/1995 | Moy et al. | |
| 5,500,200 A | 3/1996 | Mandeville et al. | |
| 5,569,635 A | 10/1996 | Moy et al. | |
| 5,658,702 A | 8/1997 | Nukada | |
| 5,702,854 A | 12/1997 | Schank et al. | |
| 5,707,916 A | 1/1998 | Snyder et al. | |
| 5,853,906 A | 12/1998 | Hsieh | |
| 5,877,110 A | 3/1999 | Snyder et al. | |
| 5,976,744 A | 11/1999 | Fuller et al. | |
| 6,002,907 A | 12/1999 | Berkes | |
| 6,020,426 A | 2/2000 | Yamaguchi et al. | |
| 6,107,117 A | 8/2000 | Bao et al. | |
| 6,107,439 A | 8/2000 | Yanus et al. | |
| 6,248,686 B1 | 6/2001 | Inagaki et al. | |
| 6,340,382 B1 | 1/2002 | Baksh et al. | |
| 6,464,756 B1 | 10/2002 | Plee | |
| 6,505,921 B2 | 1/2003 | Chwalek et al. | |
| 6,819,224 B2 | 11/2004 | Brierley | |
| 6,819,244 B2 | 11/2004 | Dukler et al. | |
| 7,067,687 B2 | 6/2006 | Pinnavaia et al. | |
| 7,177,572 B2 | 2/2007 | DiRubio et al. | |
| 7,196,210 B2 | 3/2007 | Yaghi et al. | |
| 7,202,002 B2 | 4/2007 | Tokarski et al. | |
| 7,384,717 B2 | 6/2008 | Dinh et al. | |
| 7,416,824 B2 | 8/2008 | Kondoh et al. | |
| 7,582,798 B2 | 9/2009 | Yaghi et al. | |
| 8,065,904 B1 | 11/2011 | Allendorf et al. | |
| 8,093,347 B2 | 1/2012 | Heuft et al. | |
| 8,119,314 B1 | 2/2012 | Heuft et al. | |
| 8,119,315 B1 | 2/2012 | Heuft et al. | |
| 2002/0098346 A1 | 7/2002 | Yitzchaik | |

(Continued)

FOREIGN PATENT DOCUMENTS

DE    10 2008 011 840 A1    9/2009

(Continued)

OTHER PUBLICATIONS

Peter M. Budd; Putting Order into Polymer Networks; Science, 2007, 316, 210-211.

Wan, S., Guo, J., Kim, J., Ihee, H. and Jiang, D.; A Photoconductive Covalent Organic Framework: Self-Condensed Arene Cubes Composed of Eclipsed 2D Polypyrene Sheets for Photocurrent Generation; Angewandte Chemie International Edition, 2009, 48, 5439-5442.

U.S. Appl. No. 13/351,561, filed Jan. 17, 2012 Matthew A. Heuft et al.

U.S. Appl. No. 13/246,109, filed Sep. 27, 2011 Matthew A. Heuft et al.

U.S. Appl. No. 13/246,268, filed Sep. 27, 2011 Matthew A. Heuft et al.

U.S. Appl. No. 13/351,589, filed Jan. 17, 2012 Matthew A. Heuft et al.

Nov. 14, 2011 Notice of Allowance issued in U.S. Appl. No. 12/854,957.

Nov. 14, 2011 Notice of Allowance issued in U.S. Appl. No. 12/854,962.

(Continued)

*Primary Examiner* — Terressa Boykin

(74) *Attorney, Agent, or Firm* — Oliff & Berridge, PLC

(57) ABSTRACT

A capped structured organic film comprising a plurality of segments and a plurality of linkers arranged as a covalent organic framework, wherein the structured organic film may be a multi-segment thick structured organic film.

30 Claims, 5 Drawing Sheets

U.S. PATENT DOCUMENTS

| | | |
|---|---|---|
| 2003/0099845 A1 | 5/2003 | Ogawa et al. |
| 2003/0126989 A1 | 7/2003 | Bancon et al. |
| 2003/0172808 A1 | 9/2003 | Le Bec |
| 2004/0171482 A1 | 9/2004 | Pinnavaia et al. |
| 2004/0244865 A1 | 12/2004 | Jung et al. |
| 2005/0017633 A1 | 1/2005 | Miyadera |
| 2005/0257685 A1 | 11/2005 | Baksh et al. |
| 2005/0260443 A1 | 11/2005 | Marks et al. |
| 2006/0046169 A1 | 3/2006 | Shoshi |
| 2006/0097393 A1 | 5/2006 | Uchimaru et al. |
| 2006/0154807 A1 | 7/2006 | Yaghi et al. |
| 2006/0182993 A1 | 8/2006 | Ogata et al. |
| 2006/0204742 A1 | 9/2006 | Gronbeck et al. |
| 2006/0236862 A1 | 10/2006 | Golden et al. |
| 2007/0123606 A1 | 5/2007 | Toma et al. |
| 2007/0287220 A1 | 12/2007 | Jeong et al. |
| 2008/0107980 A1 | 5/2008 | De Jong et al. |
| 2008/0132669 A1 | 6/2008 | Eriguchi et al. |
| 2008/0233343 A1 | 9/2008 | Cheng et al. |
| 2008/0268135 A1 | 10/2008 | Yokoyama et al. |
| 2008/0316247 A1 | 12/2008 | Cellura et al. |
| 2009/0025555 A1 | 1/2009 | Lively et al. |
| 2009/0046125 A1 | 2/2009 | Nystrom et al. |
| 2009/0053417 A1 | 2/2009 | Mino |
| 2009/0117476 A1 | 5/2009 | Heuft et al. |
| 2009/0149565 A1 | 6/2009 | Liu et al. |
| 2010/0015540 A1 | 1/2010 | Dinh et al. |
| 2010/0143693 A1 | 6/2010 | Yaghi et al. |
| 2010/0227071 A1 | 9/2010 | Heuft et al. |
| 2010/0227998 A1 | 9/2010 | Heuft et al. |
| 2010/0240781 A1 | 9/2010 | Cooper et al. |
| 2011/0011128 A1 | 1/2011 | Grover |
| 2011/0030555 A1 | 2/2011 | Jonschker et al. |
| 2011/0076605 A1 | 3/2011 | Doi et al. |
| 2011/0236301 A1 | 9/2011 | Kang et al. |
| 2012/0029236 A1 | 2/2012 | Cote et al. |
| 2012/0031268 A1 | 2/2012 | Yaghi et al. |
| 2012/0152117 A1 | 6/2012 | Lively et al. |

FOREIGN PATENT DOCUMENTS

| | | |
|---|---|---|
| EP | 0312376 A2 | 4/1989 |
| JP | 9 087849 A | 3/1997 |
| KR | 10-0832309 B1 | 5/2008 |
| WO | WO 91/15813 | 10/1991 |
| WO | WO 2006/064892 A1 | 6/2006 |
| WO | WO 2007/090864 A1 | 8/2007 |
| WO | WO 2007/098263 A2 | 8/2007 |
| WO | WO 2008/091976 A1 | 7/2008 |
| WO | WO 2009/022187 A1 | 2/2009 |
| WO | WO 2009/127896 A1 | 10/2009 |
| WO | WO 2010/102018 A1 | 9/2010 |
| WO | WO 2010/102025 A1 | 9/2010 |
| WO | WO 2010/102027 A1 | 9/2010 |
| WO | WO 2010/102036 A1 | 9/2010 |
| WO | WO 2010/102038 A1 | 9/2010 |
| WO | WO 2010/102043 A1 | 9/2010 |

OTHER PUBLICATIONS

Sep. 26, 2011 Office Action issued in U.S. Appl. No. 12/854,962.
Sep. 27, 2011 Office Action issued in U.S. Appl. No. 12/854,957.
Nov. 21, 2011 Office Action issued in U.S. Appl. No. 12/815,688.
Feb. 7, 2012 Office Action issued in U.S. Appl. No. 13/173,948.
Sep. 19, 2011 Notice of Allowance issued in U.S. Appl. No. 12/716,524.
Mar. 29, 2012 Office Action issued in U.S. Appl. No. 12/845,235.
Apr. 6, 2012 Office Action issued in U.S. Appl. No. 13/315,452.
May 16, 2012 Notice of Allowance issued in U.S. Appl. No. 13/173,948.
Colson et al. "Oriented 2D Covalent Organic Framework Thin Films on Single-Layer Graphene", Science, 332, 228-231 (2011).
K.S. Novoselov et al., "Electric Field Effect in Atomically Thin Carbon Films", Science, Oct. 22, 2004, pp. 666-669, vol. 306.
Stankovich et al., "Graphene-Based Composite Materials", Nature, Jul. 20, 2006, pp. 282-286, vol. 442.
U.S. Appl. No. 13/173,948, filed Jun. 30, 2011 Adrien Pierre Cote et al.
U.S. Appl. No. 13/042,950, filed Mar. 8, 2011 Adrien Pierre Cote et al.
U.S. Appl. No. 13/181,761, filed Jul. 13, 2011 Adrien Pierre Cote et al.
U.S. Appl. No. 13/181,912, filed Jul. 13, 2011 Adrien Pierre Cote et al.
U.S. Appl. No. 13/174,046, filed Jun. 30, 2011 Matthew A. Heuft et al.
U.S. Appl. No. 13/182,047, filed Jul. 13, 2011 Adrien Pierre Cote et al.
Jun. 1, 2011 Office Action issued in U.S. Appl. No. 12/716,524.
Shun Wan et al., "A Belt-Shaped, Blue Luminescent, and Semiconducting Covalent Organic Framework," Angew. Chem. Int. Ed., vol. 47, pp. 8826-8830 (published on Web Jan. 10, 2008).
Nikolas A. A. Zwaneveld et al., "Organized Formation of 2D Extended Covalent Organic Frameworks at Surfaces," J. Am. Chem. Soc., vol. 130, pp. 6678-6679 (published on web Apr. 30, 2008).
Adrien P. Cote et al., "Porous, Crystalline, Covalent Organic Frameworks," Science, vol. 310, pp. 1166-1170 (Nov. 18, 2005).
Hani El-Kaderi et al., "Designed Synthesis of 3D Covalent Organic Frameworks," Science, vol. 316, pp. 268-272 (Apr. 13, 2007).
Adrien P. Cote et al., "Reticular Synthesis of Microporous and Mesoporous Covalent Organic Frameworks" J. Am. Chem. Soc., vol. 129, 12914-12915 (published on web Oct. 6, 2007).
Omar M. Yaghi et al., "Reticular synthesis and the design of new materials," Nature, vol. 423, pp. 705-714 (Jun. 12, 2003).
Nathan W. Ockwig et al., "Reticular Chemistry: Occurrence and Taxonomy of Nets and Grammar for the Design of Frameworks," Acc. Chem. Res., vol. 38, No. 3, pp. 176-182 (published on web Jan. 19, 2005).
Pierre Kuhn et al., "Porous, Covalent Triazine-Based Frameworks Prepared by Ionothermal Synthesis," Angew. Chem. Int. Ed., vol. 47, pp. 3450-3453. (Published on web Mar. 10, 2008).
Jia-Xing Jiang et al., "Conjugated Microporous Poly(aryleneethylnylene) Networks," Angew. Chem. Int. Ed., vol. 46, (2008) pp. 1-5 (Published on web Sep. 26, 2008).
Hunt, J.R. et al. "Reticular Synthesis of Covalent-Organic Borosilicate Frameworks" J. Am. Chem. Soc., vol. 130, (2008), 11872-11873. (published on web Aug. 16, 2008).
Apr. 28, 2010 International Search Report issued in PCT/US 10/26082.
Apr. 28, 2010 Written Opinion issued in PCT/US 10/26082.
Apr. 27, 2010 International Search Report issued in PCT/US 10/26071.
Apr. 27, 2010 Written Opinion issued in PCT/US 10/26071.
Apr. 28, 2010 International Search Report issued in PCT/US 10/26091.
Apr. 28, 2010 Written Opinion issued in PCT/US 10/26091.
Apr. 28, 2010 International Search Report issued in PCT/US 10/26100.
Apr. 28, 2010 Written Opinion issued in PCT/US 10/26100.
Apr. 16, 2010 International Search Report issued in PCT/US 10/26079.
Apr. 16, 2010 Written Opinion issued in PCT/US 10/26079.
Apr. 20, 2010 International Search Report issued in PCT/US 10/26094.
Apr. 20, 2010 Written Opinion issued in PCT/US 10/26094.
U.S. Appl. No. 12/716,571, filed Mar. 3, 2010 Matthew A. Heuft et al.
U.S. Appl. No. 12/716,524, filed Mar. 3, 2010 Matthew A. Heuft et al.
U.S. Appl. No. 12/716,324, filed Mar. 3, 2010 Matthew A. Heuft et al.
U.S. Appl. No. 12/716,686, filed Mar. 3, 2010 Matthew A. Heuft et al.
U.S. Appl. No. 12/716,449, filed Mar. 3, 2010 Adrien Pierre Cote et al.
Cassie, A.B.D. et al., "Wettability of Porous Surfaces," Trans. Faraday Soc., vol. 40, pp. 546-551, Jun. 1944.
U.S. Appl. No. 12/854,962, filed Aug. 12, 2010 Matthew A. Heuft et al.
U.S. Appl. No. 12/815,688, filed Jun. 15, 2010 Adrien P. Cote et al.
U.S. Appl. No. 12/854,957, filed Aug. 12, 2010 Matthew A. Heuft et al.
U.S. Appl. No. 12/845,052, filed Jul. 28, 2010 Adrien P. Cote et al.
U.S. Appl. No. 12/845,235, filed Jul. 28, 2010 Adrien P. Cote et al.
U.S. Appl. No. 12/566,568, filed Sep. 24, 2009 Eugene M. Chow et al.

U.S. Appl. No. 12/566,518, filed Sep. 24, 2009 Eugene M. Chow et al.
U.S. Appl. No. 12/716,706, filed Mar. 3, 2010 Adrien Pierre Cote et al.
Jun. 19, 2012 German Search Report issued in Application No. 10 2011 079 277.5 (with translation).
Aug. 10, 2012 Notice of Allowance issued in U.S. Appl. No. 13/181,912.
Aug. 10, 2012 Office Action issued in U.S. Appl. No. 12/716,449.
Aug. 3, 2012 Office Action issued in U.S. Appl. No. 12/716,686.
Jul. 6, 2012 Office Action issued in U.S. Appl. No. 12/716,706.
Aug. 3, 2012 Office Action issued in U.S. Appl. No. 12/815,688.
Jun. 25, 2012 Office Action issued in U.S. Appl. No. 12/845,052.
Aug. 8, 2012 Office Action issued in U.S. Appl. No. 13/181,761.
U.S. Appl. No. 13/572,095, filed Aug. 10, 2012, Sara J. Vella et al.
U.S. Appl. No. 13/571,933, filed Aug. 10, 2012, Sara J. Vella et al.
Extended European Search Report for European Patent Application No. 10749278.7 dated Aug. 8, 2012.
European Search Report for European Patent Application No. 10749283.7 dated Aug. 10, 2012.
European Search Report for European Patent Application No. 10749285.2 dated Aug. 6, 2012.
European Search Report for European Patent Application No. 10749276.1 dated Aug. 6, 2012.
European Search Report for European Patent Application No. 10749274.6 dated Aug. 6, 2012.
European Search Report for European Patent Application No. 10749289.4 dated Aug. 10, 2012.
Notice of Allowance for U.S. Appl. No. 13/315,452 mailed Aug. 15, 2012.
Sep. 6, 2012 Office Action issued in U.S. Appl. No. 13/182,047.
Sep. 6, 2012 Office Action issued in U.S. Appl. No. 12/716,324.

CAPPED STRUCTURED ORGANIC FILM COMPOSITIONS

CROSS-REFERENCE TO RELATED APPLICATIONS

This nonprovisional application is related to U.S. patent application Ser. Nos. 12/716,524; 12/716,449; 12/716,706; 12/716,324; 12/716,686; 12/716,571; and 12/815,688, entitled "Structured Organic Films," "Structured Organic Films Having an Added Functionality," "Mixed Solvent Process for Preparing Structured Organic Films," "Composite Structured Organic Films," "Process For Preparing Structured Organic Films (SOFs) Via a Pre-SOF," "Electronic Devices Comprising Structured Organic Films," and "Periodic Structured Organic Films;" and U.S. Provisional Application No. 61/157,411, entitled "Structured Organic Films" filed Mar. 4, 2009, the disclosures of which are totally incorporated herein by reference in their entireties.

BACKGROUND OF THE INVENTION

Materials whose chemical structures are comprised of molecules linked by covalent bonds into extended structures may be placed into two classes: (1) polymers and cross-linked polymers, and (2) covalent organic frameworks (also known as covalently linked organic networks).

The first class, polymers and cross-linked polymers, is typically embodied by polymerization of molecular monomers to form long linear chains of covalently-bonded molecules. Polymer chemistry processes can allow for polymerized chains to, in turn, or concomitantly, become 'cross-linked.' The nature of polymer chemistry offers poor control over the molecular-level structure of the formed material, i.e. the organization of polymer chains and the patterning of molecular monomers between chains is mostly random. Nearly all polymers are amorphous, save for some linear polymers that efficiently pack as ordered rods. Some polymer materials, notably block co-polymers, can possess regions of order within their bulk. In the two preceding cases the patterning of polymer chains is not by design, any ordering at the molecular-level is a consequence of the natural intermolecular packing tendencies.

The second class, covalent organic frameworks (COFs), differ from the first class (polymers/cross-linked polymers) in that COFs are intended to be highly patterned. In COF chemistry molecular components are called molecular building blocks rather than monomers. During COF synthesis molecular building blocks react to form two- or three-dimensional networks. Consequently, molecular building blocks are patterned throughout COF materials and molecular building blocks are linked to each other through strong covalent bonds.

COFs developed thus far are typically powders with high porosity and are materials with exceptionally low density. COFs can store near-record amounts of argon and nitrogen. While these conventional. COFs are useful, there is a need, addressed by embodiments of the present invention, for new materials that offer advantages over conventional COFs in terms of enhanced characteristics.

SUMMARY OF THE DISCLOSURE

There is provided in embodiments capped structured organic films comprising a capping unit, a plurality of segments and a plurality of linkers arranged as a covalent organic framework, wherein at a macroscopic level the covalent organic framework is a film.

BRIEF DESCRIPTION OF THE DRAWINGS

Other aspects of the present disclosure will become apparent as the following description proceeds and upon reference to the following figures which represent illustrative embodiments.

Unless otherwise noted, the same reference numeral in different Figures refers to the same or similar feature.

DETAILED DESCRIPTION

Figure 1:
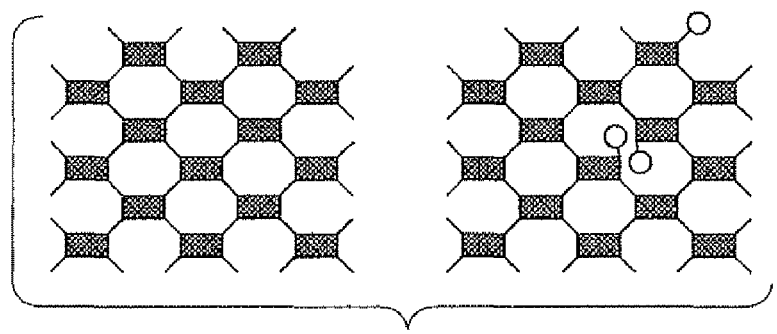
FIG. 1 illustrates the differences between typical SOF and a capped SOF. Left hand side: representation of a typical SOF network; right hand side: representation of capped SOF illustrating interruptions in the network and covalently linked capping group (circle).

"Structured organic film" (SOF) refers to a COF that is a film at a macroscopic level. The SOFs of the present disclosure have a capping unit or group added into the SOF formulation, which (after film formation), ultimately bonds to the SOF.

In this specification and the claims that follow, singular forms such as "a," "an," and "the" include plural forms unless the content clearly dictates otherwise.

The term "SOF" generally refers to a covalent organic framework (COP) that is a film at a macroscopic level. The phrase "macroscopic level" refers, for example, to the naked eye view of the present SOFs. Although COFs are a network at the "microscopic level" or "molecular level" (requiring use of powerful magnifying equipment or as assessed using scattering methods), the present SOF is fundamentally different at the "macroscopic level" because the film is for instance orders of magnitude larger in coverage than a microscopic level COF network. SOFs described herein have macroscopic morphologies much different than typical COFs previously synthesized.

Additionally, when a capping unit is introduced into the SOF, the SOF framework is locally 'interrupted' where the capping units are present. These SOF compositions are 'covalently doped' because a foreign molecule is bonded to the SOF framework when capping units are present. Capped SOF compositions may alter the properties of SOFs without changing constituent building blocks. For example, the mechanical and physical properties of the capped SOF where the SOF framework is interrupted may differ from that of an uncapped SOF.

The SOFs of the present disclosure are at the macroscopic level substantially pinhole-free SOFs or pinhole-free SOFs having continuous covalent organic frameworks that can extend over larger length scales such as for instance much greater than a millimeter to lengths such as a meter and, in theory, as much as hundreds of meters. It will also be appreciated that SOFs tend to have large aspect ratios where typically two dimensions of a SOF will be much larger than the third. SOFs have markedly fewer macroscopic edges and disconnected external surfaces than a collection of COF particles.

In embodiments, a "substantially pinhole-free SOF" or "pinhole-free SOF" may be formed from a reaction mixture deposited on the surface of an underlying substrate. The term "substantially pinhole-free SOF" refers, for example, to an SOF that may or may not be removed from the underlying substrate on which it was formed and contains substantially no pinholes, pores or gaps greater than the distance between the cores of two adjacent segments per square cm; such as, for example, less than 10 pinholes, pores or gaps greater than about 250 nanometers in diameter per cm$^2$, or less than 5 pinholes, pores or gaps greater than about 100 nanometers in diameter per cm$^2$. The term "pinhole-free SOF" refers, for example, to an SOF that may or may not be removed from the underlying substrate on which it was formed and contains no pinholes, pores or gaps greater than the distance between the cores of two adjacent segments per micron$^2$, such as no pinholes, pores or gaps greater than about 500 Angstroms in diameter per micron$^2$, or no pinholes, pores or gaps greater than about 250 Angstroms in diameter per micron$^2$, or no pinholes, pores or gaps greater than about 100 Angstroms in diameter per micron$^2$.

In embodiments, the SOF comprises at least one atom of an element that is not carbon, such at least one atom selected from the group consisting of hydrogen, oxygen, nitrogen, silicon, phosphorous, selenium, fluorine, boron, and sulfur. In further embodiments, the SOF is a boroxine-, borazine-, borosilicate-, and boronate ester-free SOF.

Molecular Building Block

The SOFs of the present disclosure comprise molecular building blocks having a segment (S) and functional groups (Fg). Molecular building blocks require at least two functional groups (x≧2) and may comprise a single type or two or more types of functional groups. Functional groups are the reactive chemical moieties of molecular building blocks that participate in a chemical reaction to link together segments during the SOF forming process. A segment is the portion of the molecular building block that supports functional groups and comprises all atoms that are not associated with functional groups. Further, the composition of a molecular building block segment remains unchanged after SOF formation.

Functional Group

Functional groups are the reactive chemical moieties of molecular building blocks that may participate in a chemical reaction to link together segments during the SOF forming process. Functional groups may be composed of a single atom, or functional groups may be composed of more than one atom. The atomic compositions of functional groups are those compositions normally associated with reactive moieties in chemical compounds. Non-limiting examples of functional groups include halogens, alcohols, ethers, ketones, carboxylic acids, esters, carbonates, amines, amides, imines, ureas, aldehydes, isocyanates, tosylates, alkenes, alkynes and the like.

Molecular building blocks contain a plurality of chemical moieties, but only a subset of these chemical moieties are intended to be functional groups during the SOF forming process. Whether or not a chemical moiety is considered a functional group depends on the reaction conditions selected for the SOF forming process. Functional groups (Fg) denote a chemical moiety that is a reactive moiety, that is, a functional group during the SOF forming process.

In the SOF forming process the composition of a functional group will be altered through the loss of atoms, the gain of atoms, or both the loss and the gain of atoms; or, the functional group may be lost altogether. In the SOF, atoms previously associated with functional groups become associated with linker groups, which are the chemical moieties that join together segments. Functional groups have characteristic chemistries and those of ordinary skill in the art can generally recognize in the present molecular building blocks the atom(s) that constitute functional group(s). It should be noted that an atom or grouping of atoms that are identified as part of the molecular building block functional group may be preserved in the linker group of the SOF. Linker groups are described below.

Capping Unit

Capping units of the present disclosure are molecules that 'interrupt' the regular network of covalently bonded building blocks normally present in an SOF. The differences between a SOF and a capped SOF are illustrated in FIG. 1. Capped SOF compositions are tunable materials whose properties can be varied through the type and amount of capping unit introduced. Capping units may comprise a single type or two or more types of functional groups and/or chemical moieties.

In embodiments, the capping units have a structure that is unrelated to the structure of any of the molecular building blocks that are added into the SOF formulation, which (after film formation) ultimately becomes the SOF.

In embodiments, the capping units have a structure that substantially corresponds to the structure of one of the molecular building blocks (such as the molecular building blocks for SOFs that are detailed in U.S. patent application Ser. Nos. 12/716,524; 12/716,449; 12/716,706; 12/716,324; 12/716,686; 12/716,571, and 12/815,688 which have been incorporated by reference) that is added to the SOF formulation, but one or more of the functional groups present on the building block is either missing or has been replaced with a different chemical moiety or functional group that will not participate in a chemical reaction (with the functional group(s) of the building blocks that are initially present) to link together segments during the SOF forming process.

For example, for a molecular building block, such as tris-(4-hydroxymethyl)triphenylamine:

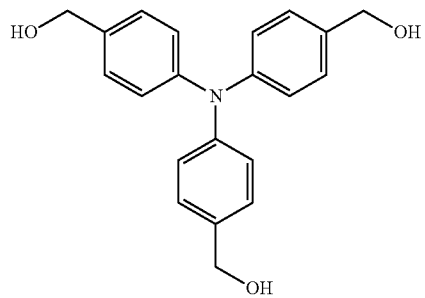

among the many possible capping units that may be used, suitable capping units may, for example, include:

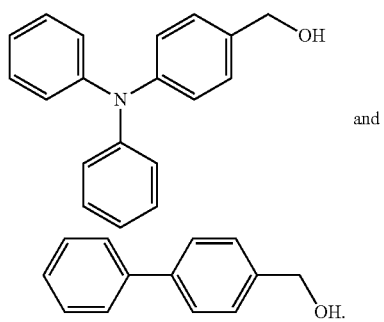

and

A capping group having a structure unrelated to the molecular building block may be, for example, an alkyl moiety (for example, a branched or unbranched saturated hydrocarbon group, derived from an alkane and having the general formula $C_nH_{2n+1}$, in which n is a number of 1 or more) in which one of the hydrogen atoms has been replaced by an —OH group. In such a formulation, a reaction between the capping unit and the molecular building block, for example, an acid catalyzed reaction between the alcohol (—OH) groups, would link the capping unit and the molecular building blocks together through the formation of (linking) ether groups.

In embodiments, the capping unit molecules may be monofunctionalized. For example, in embodiments, the capping units may comprise only a single suitable or complementary functional group (as described above) that participates in a chemical reaction to link together segments during the SOF forming process and thus cannot bridge any further adjacent molecular building blocks (until a building block with a suitable or complementary functional group is added, such as when an additional SOF is formed on top of a capped SOF base layer and a multilayer SOF is formed).

When such capping units are introduced into the SOF coating formulation, upon curing, interruptions in the SOF framework are introduced. Interruptions in the SOF framework are therefore sites where the single suitable or complementary functional group of the capping units have reacted with the molecular building block and locally terminate (or cap) the extension of the SOF framework and interrupt the regular network of covalently bonded building blocks normally present in an SOF. The type of capping unit (or structure or the capping unit) introduced into the SOF framework may be used to tune the properties of the SOF.

In embodiments, the capping unit molecules may comprise more than one chemical moiety or functional group. For example, the SOF coating formulation, which (after film formation), ultimately becomes bonded in the SOF may comprise a capping unit having at least two or more chemical moieties or functional groups, such as 2, 3, 4, 5, 6 or more chemical moieties or functional groups, where only one of the functional groups is a suitable or complementary functional group (as described above) that participates in a chemical reaction to link together segments during the SOF forming process. The various other chemical moieties or functional groups present on the molecular building block are chemical moieties or functional groups that are not suitable or complementary to participate in the specific chemical reaction to link together segments initially present during the SOF forming process and thus cannot bridge any further adjacent molecular building blocks. However, after the SOF is formed such chemical moieties and/or functional groups may be available for further reaction (similar to dangling functional groups, as discussed below) with additional components and thus allow for the further refining and tuning of the various properties of the formed SOF, or chemically attaching various other SOF layers in the formation of multilayer SOFs.

In embodiments, the molecular building blocks may have x functional groups (where x is three or more) and the capping unit molecules may comprise a capping unit molecule having x−1 functional groups that are suitable or complementary functional group (as described above) and participate in a chemical reaction to link together segments during the SOF forming process. For example, x would be three for tris-(4-hydroxymethyl)triphenylamine (above), and x would be four for the building block illustrated below, N,N,N',N'-tetrakis-[(4-hydroxymethyl)phenyl]-biphenyl-4,4'-diamine:

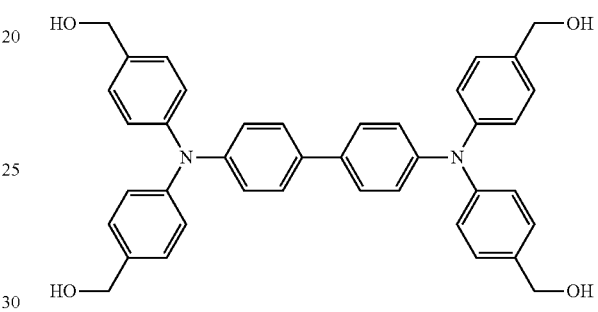

A capping unit molecule having x−1 functional groups that are suitable or complementary functional groups (as described above) and participate in a chemical reaction to link together segments during the SOF forming process would have 2 functional groups (for a molecular building block such as tris-(4-hydroxymethyl)triphenylamine), and 3 functional groups (for N,N,N',N'-tetrakis-[(4-hydroxymethyl)phenyl]-biphenyl-4,4'-diamine) that are suitable or complementary functional group (as described above) and participate in a chemical reaction to link together segments during the SOF forming process. The other functional group present may be a chemical moiety or a functional group that is not suitable or complementary to participate in the specific chemical reaction to link together segments during the SOF forming process and thus cannot bridge any further adjacent molecular building blocks. However, after the SOF is formed such functional groups may be available for further reaction with additional components and thus allowing for the further refining and tuning of the various properties of the formed SOF.

In embodiments, the Capping unit may comprise a mixture of capping units, such as any combination of a first capping unit, a second capping unit, a third capping unit, a fourth capping unit, etc., where the structure of the capping unit varies. In embodiments, the structure of a capping unit or a combination of multiple capping units may be selected to either enhance or attenuate the chemical and physical properties of SOF; or the identity of the chemical moieties or functional group(s) on that are not suitable or complementary to participate in the chemical reaction to link together segments during the SOF forming process may be varied to form a mixture of capping units. Thus, the type of capping unit introduced into the SOF framework may be selected to introduce or tune a desired property of SOF.

In embodiments, a SOF contains segments, which are not located at the edges of the SOF, that are connected by linkers to at least three other segments and/or capping groups. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks. In embodiments, Type 2 and 3 SOF contains at least one segment type, which are not located at the edges of the SOF, that are connected by linkers to at least three other segments and/or capping groups. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks.

In embodiments, the SOF comprises a plurality of segments, where all segments have an identical structure, and a plurality of linkers, which may or may not have an identical structure, wherein the segments that are not at the edges of the SOF are connected by linkers to at least three other segments and/or capping groups. In embodiments, the SOF comprises a plurality of segments where the plurality of segments comprises at least a first and a second segment that are different in structure, and the first segment is connected by linkers to at least three other segments and/or capping groups when it is not at the edge of the SOF.

In embodiments, the SOF comprises a plurality of linkers including at least a first and a second linker that are different in structure, and the plurality of segments either comprises at least a first and a second segment that are different in structure, where the first segment, when not at the edge of the SOF, is connected to at least three other segments and/or capping groups, wherein at least one of the connections is via the first linker, and at least one of the connections is via the second linker; or comprises segments that all have an identical structure, and the segments that are not at the edges of the SOF are connected by linkers to at least three other segments and/or capping groups, wherein at least one of the connections is via the first linker, and at least one of the connections is via the second linker.

Segment

A segment is the portion of the molecular building block that supports functional groups and comprises all atoms that are not associated with functional groups. Further, the composition of a molecular building block segment remains unchanged after SOF formation. In embodiments, the SOF may contain a first segment having a structure the same as or different from a second segment. In other embodiments, the structures of the first and/or second segments may be the same as or different from a third segment, forth segment, fifth segment, etc. A segment is also the portion of the molecular building block that can provide an inclined property. Inclined properties are described later in the embodiments.

In specific embodiments, the segment of the SOF comprises at least one atom of an element that is not carbon, such at least one atom selected from the group consisting of hydrogen, oxygen, nitrogen, silicon, phosphorous, selenium, fluorine, boron, and sulfur.

A description of various exemplary molecular building blocks, linkers, SOF types, strategies to synthesize a specific SOF type with exemplary chemical structures, building blocks whose symmetrical elements are outlined, and classes of exemplary molecular entities and examples of members of each class that may serve as molecular building blocks for SOFs are detailed in U.S. patent application Ser. Nos. 12/716, 524; 12/716,449; 12/716,706; 12/716,324; 12/716,686; and 12/716,571, entitled "Structured Organic Films," "Structured Organic Films Having an Added Functionality," "Mixed Solvent Process for Preparing Structured Organic Films," "Composite Structured Organic Films," "Process For Preparing Structured Organic Films (SOFs) Via a Pre-SOF," "Electronic Devices Comprising Structured Organic Films," the disclosures of which are totally incorporated herein by reference in their entireties.

Linker

A linker is a chemical moiety that emerges in a SOF upon chemical reaction between functional groups present on the molecular building blocks and/or capping unit.

A linker may comprise a covalent bond, a single atom, or a group of covalently bonded atoms. The former is defined as a covalent bond linker and may be, for example, a single covalent bond or a double covalent bond and emerges when functional groups on all partnered building blocks are lost entirely. The latter linker type is defined as a chemical moiety linker and may comprise one or more atoms bonded together by single covalent bonds, double covalent bonds, or combinations of the two. Atoms contained in linking groups originate from atoms present in functional groups on molecular building blocks prior to the SOF fowling process. Chemical moiety linkers may be well-known chemical groups such as, for example, esters, ketones, amides, imines, ethers, urethanes, carbonates, and the like, or derivatives thereof.

For example, when two hydroxyl (—OH) functional groups are used to connect segments in a SOF via an oxygen atom, the linker would be the oxygen atom, which may also be described as an ether linker. In embodiments, the SOF may contain a first linker having a structure the same as or different from a second linker. In other embodiments, the structures of the first and/or second linkers may be the same as or different from a third linker, etc.

A capping unit may be bonded in the SOF in any desired amount as long as the general SOF framework is sufficiently maintained. For example, in embodiments, a capping unit may be bonded to at least 0.1% of all linkers, but not more than about 40% of all linkers present in an SOF, such as from about 0.5% to about 30%, or from about 2% to about 20%. In embodiments, substantially all segments may be bound to at least one capping unit, where the term "substantially all" refers, for example, to more than about 95%, such as more than about 99% of the segments of the SOF. In the event capping units bond to more than 50% of the available functional groups on the molecular building blocks (from which the linkers emerge), oligomers, linear polymers, and molecular building blocks that are fully capped with capping units may predominately form instead of a SOF.

In specific embodiments, the linker comprises at least one atom of an element that is not carbon, such at least one atom selected from the group consisting of hydrogen, oxygen, nitrogen, silicon, phosphorous, selenium, fluorine, boron, and sulfur.

Metrical Parameters of SOFs

SOFs have any suitable aspect ratio. In embodiments, SOFs have aspect ratios for instance greater than about 30:1 or greater than about 50:1, or greater than about 70:1, or greater than about 100:1, such as about 1000:1. The aspect ratio of a SOF is defined as the ratio of its average width or diameter (that is, the dimension next largest to its thickness) to its average thickness (that is, its shortest dimension). The term 'aspect ratio,' as used here, is not bound by theory. The longest dimension of a SOF is its length and it is not considered in the calculation of SOF aspect ratio.

Generally, SOFs have widths and lengths, or diameters greater than about 500 micrometers, such as about 10 mm, or 30 mm. The SOFs have the following illustrative thicknesses:

about 10 Angstroms to about 250 Angstroms, such as about 20 Angstroms to about 200 Angstroms, for a mono-segment thick layer and about 20 nm to about 5 mm, about 50 nm to about 10 mm for a multi-segment thick layer.

SOF dimensions may be measured using a variety of tools and methods. For a dimension about 1 micrometer or less, scanning electron microscopy is the preferred method. For a dimension about 1 micrometer or greater, a micrometer (or ruler) is the preferred method.

Multilayer SOFs

A SOF may comprise a single layer or a plurality of layers (that is, two, three or more layers). SOFs that are comprised of a plurality of layers may be physically joined (e.g., dipole and hydrogen bond) or chemically joined. Physically attached layers are characterized by weaker interlayer interactions or adhesion; therefore physically attached layers may be susceptible to delamination from each other. Chemically attached layers are expected to have chemical bonds (e.g., covalent or ionic bonds) or have numerous physical or intermolecular (supramolecular) entanglements that strongly link adjacent layers.

Therefore, delamination of chemically attached layers is much more difficult. Chemical attachments between layers may be detected using spectroscopic methods such as focusing infrared or Raman spectroscopy, or with other methods having spatial resolution that can detect chemical species precisely at interfaces. In cases where chemical attachments between layers are different chemical species than those within the layers themselves it is possible to detect these attachments with sensitive bulk analyses such as solid-state nuclear magnetic resonance spectroscopy or by using other bulk analytical methods.

In the embodiments, the SOF may be a single layer (mono-segment thick or multi-segment thick) or multiple layers (each layer being mono-segment thick or multi-segment thick). "Thickness" refers, for example, to the smallest dimension of the film. As discussed above, in a SOF, segments are molecular units that are covalently bonded through linkers to generate the molecular framework of the film. The thickness of the film may also be defined in terms of the number of segments that is counted along that axis of the film when viewing the cross-section of the film. A "monolayer" SOF is the simplest case and refers, for example, to where a film is one segment thick. A SOF where two or more segments exist along this axis is referred to as a "multi-segment" thick SOF.

An exemplary method for preparing physically attached multilayer SOFs includes: (1) forming a base SOF layer that may be cured by a first curing cycle, and (2) forming upon the base layer a second reactive wet layer followed by a second curing cycle and, if desired, repeating the second step to form a third layer, a forth layer and so on. The physically stacked multilayer SOFs may have thicknesses greater than about 20 Angstroms such as, for example, the following illustrative thicknesses: about 20 Angstroms to about 10 cm, such as about 1 nm to about 10 mm, or about 0.1 mm Angstroms to about 5 mm. In principle there is no limit with this process to the number of layers that may be physically stacked.

In embodiments, a multilayer SOF is formed by a method for preparing chemically attached multilayer SOF by: (1) forming a base SOF layer having functional groups present on the surface (or dangling functional groups) from a first reactive wet layer, and (2) forming upon the base layer a second SOF layer from a second reactive wet layer that comprises molecular building blocks with functional groups capable of reacting with the dangling functional groups on the surface of the base SOF layer. In further embodiments, a capped SOF may serve as the base layer in which the functional groups present that were not suitable or complementary to participate in the specific chemical reaction to link together segments during the base layer SOF forming process may be available for reacting with the molecular building blocks of the second layer to form a chemically bonded multilayer SOF. If desired, the formulation used to form the second SOF layer should comprise molecular building blocks with functional groups capable of reacting with the functional groups from the base layer as well as additional functional groups that will allow for a third layer to be chemically attached to the second layer. The chemically stacked multilayer SOFs may have thicknesses greater than about 20 Angstroms such as, for example, the following illustrative thicknesses: about 20 Angstroms to about 10 cm, such as about 1 nm to about 10 mm, or about 0.1 mm Angstroms to about 5 mm. In principle there is no limit with this process to the number of layers that may be chemically stacked.

In embodiments, the method for preparing chemically attached multilayer SOFs comprises promoting chemical attachment of a second SOF onto an existing SOF (base layer) by using a small excess of one molecular building block (when more than one molecular building block is present) during the process used to form the SOF (base layer) whereby the functional groups present on this molecular building block will be present on the base layer surface. The surface of base layer may be treated with an agent to enhance the reactivity of the functional groups or to create an increased number of functional groups.

In an embodiment the dangling functional groups or chemical moieties present on the surface of an SOF or capped SOF may be altered to increase the propensity for covalent attachment (or, alternatively, to disfavor covalent attachment) of particular classes of molecules or individual molecules, such as SOFs, to a base layer or any additional substrate or SOF layer. For example, the surface of a base layer, such as an SOF layer, which may contain reactive dangling functional groups, may be rendered pacified through surface treatment with a capping chemical group. For example, a SOF layer having dangling hydroxyl alcohol groups may be pacified by treatment with trimethylsiylchloride thereby capping hydroxyl groups as stable trimethylsilylethers. Alternatively, the surface of base layer may be treated with a non-chemically bonding agent, such as a wax, to block reaction with dangling functional groups from subsequent layers.

Molecular Building Block Symmetry

Molecular building block symmetry relates to the positioning of functional groups (Fgs) around the periphery of the molecular building block segments. Without being bound by chemical or mathematical theory, a symmetric molecular building block is one where positioning of Fgs may be associated with the ends of a rod, vertexes of a regular geometric shape, or the vertexes of a distorted rod or distorted geometric shape. For example, the most symmetric option for molecular building blocks containing four Fgs are those whose Fgs overlay with the corners of a square or the apexes of a tetrahedron.

Use of symmetrical building blocks is practiced in embodiments of the present disclosure for two reasons: (1) the patterning of molecular building blocks may be better anticipated because the linking of regular shapes is a better understood process in reticular chemistry, and (2) the complete reaction between molecular building blocks is facilitated because for less symmetric building blocks errant conformations/orientations may be adopted which can possibly initiate numerous linking defects within SOFs.

In embodiments, a Type 1 SOF contains segments, which are not located at the edges of the SOF, that are connected by linkers to at least three other segments. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks. In embodiments, Type 2 and 3 SOF contains at least one segment type, which are not located at the edges of the SOF, that are connected by linkers to at least three other segments. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks.

Practice of Linking Chemistry

In embodiments linking chemistry may occur wherein the reaction between functional groups produces a volatile byproduct that may be largely evaporated or expunged from the SOF during or after the film forming process or wherein no byproduct is formed. Linking chemistry may be selected to achieve a SOF for applications where the presence of linking chemistry byproducts is not desired. Linking chemistry reactions may include, for example, condensation, addition/elimination, and addition reactions, such as, for example, those that produce esters, imines, ethers, carbonates, urethanes, amides, acetals, and silyl ethers.

In embodiments the linking chemistry via a reaction between function groups producing a non-volatile byproduct that largely remains incorporated within the SOF after the film forming process. Linking chemistry in embodiments may be selected to achieve a SOF for applications where the presence of linking chemistry byproducts does not impact the properties or for applications where the presence of linking chemistry byproducts may alter the properties of a SOF (such as, for example, the electroactive, hydrophobic or hydrophilic nature of the SOF). Linking chemistry reactions may include, for example, substitution, metathesis, and metal catalyzed coupling reactions, such as those that produce carbon-carbon bonds.

For all linking chemistry the ability to control the rate and extent of reaction between building blocks via the chemistry between building block functional groups is an important aspect of the present disclosure. Reasons for controlling the rate and extent of reaction may include adapting the film forming process for different coating methods and tuning the microscopic arrangement of building blocks to achieve a periodic SOF, as defined in earlier embodiments.

Innate Properties of COFs

COFs have innate properties such as high thermal stability (typically higher than 400° C. under atmospheric conditions); poor solubility in organic solvents (chemical stability), and porosity (capable of reversible guest uptake). In embodiments, SOFs may also possess these innate properties.

Added Functionality of SOFs

Added functionality denotes a property that is not inherent to conventional COFs and may occur by the selection of molecular building blocks wherein the molecular compositions provide the added functionality in the resultant SOF. Added functionality may arise upon assembly of molecular building blocks and/or capping units having an "inclined property" for that added functionality. Added functionality may also arise upon assembly of molecular building blocks having no "inclined property" for that added functionality but the resulting SOF has the added functionality as a consequence of linking segments (S) and linkers into a SOF. In embodiments, added functionality may also arise upon the addition and assembly of molecular building blocks and capping units having no "inclined property" for that added functionality but the resulting SOF has the added functionality as a consequence of linking segments, linkers, and capping units into a SOF. Furthermore, emergence of added functionality may arise from the combined effect of using molecular building blocks bearing an "inclined property" for that added functionality whose inclined property is modified or enhanced upon linking together the segments and linkers into a SOF.

An Inclined Property of a Molecular Building Block

The term "inclined property" of a molecular building block refers, for example, to a property known to exist for certain molecular compositions or a property that is reasonably identifiable by a person skilled in art upon inspection of the molecular composition of a segment. As used herein, the terms "inclined property" and "added functionality" refer to the same general property (e.g., hydrophobic, electroactive, etc.) but "inclined property" is used in the context of the molecular building block and "added functionality" is used in the context of the SOF.

The hydrophobic (superhydrophobic), hydrophilic, lipophobic (superlipophobic), lipophilic, photochromic and/or electroactive (conductor, semiconductor, charge transport material) nature of an SOF are some examples of the properties that may represent an "added functionality" of an SOF. These and other added functionalities may arise from the inclined properties of the molecular building blocks or may arise from building blocks that do not have the respective added functionality that is observed in the SOF.

The term hydrophobic (superhydrophobic) refers, for example, to the property of repelling water, or other polar species such as methanol, it also means an inability to absorb water and/or to swell as a result. Furthermore, hydrophobic implies an inability to form strong hydrogen bonds to water or other hydrogen bonding species. Hydrophobic materials are typically characterized by having water contact angles greater than 90' and superhydrophobic materials have water contact angles greater than $150°$ as measured using a contact angle goniometer or related device.

The term hydrophilic refers, for example, to the property of attracting, adsorbing, or absorbing water or other polar species, or a surface that is easily wetted by such species. Hydrophilic materials are typically characterized by having less than $20°$ water contact angle as measured using a contact angle goniometer or related device. Hydrophilicity may also be characterized by swelling of a material by water or other polar species, or a material that can diffuse or transport water, or other polar species, through itself. Hydrophilicity, is further characterized by being able to form strong or numerous hydrogen bonds to water or other hydrogen bonding species.

The term lipophobic (oleophobic) refers, for example, to the property of repelling oil or other non-polar species such as alkanes, fats, and waxes. Lipophobic materials are typically characterized by having oil contact angles greater than $90°$ as measured using a contact angle goniometer or related device.

The term lipophilic (oleophilic) refers, for example, to the property attracting oil or other non-polar species such as alkanes, fats, and waxes or a surface that is easily wetted by such species. Lipophilic materials are typically characterized by having a low to nil oil contact angle as measured using, for example, a contact angle goniometer. Lipophilicity can also be characterized by swelling of a material by hexane or other non-polar liquids.

The term photochromic refers, for example, to the ability to demonstrate reversible color changes when exposed to electromagnetic radiation. SOF compositions containing photochromic molecules may be prepared and demonstrate reversible color changes when exposed to electromagnetic radiation. These SOFs may have the added functionality of photochromism. The robustness of photochromic SOFs may enable their use in many applications, such as photochromic SOFs for erasable paper, and light responsive films for window tinting/shading and eye wear. SOF compositions may contain any suitable photochromic molecule, such as a difunctional photochromic molecules as SOF molecular building blocks (chemically bound into SOF structure), a monofunctional photochromic molecules as SOF capping units (chemically bound into SOF structure, or unfunctionalized photochromic molecules in an SOF composite (not chemically bound into SOF structure). Photochromic SOFs may change color upon exposure to selected wavelengths of light and the color change may be reversible.

SOF compositions containing photochromic molecules that chemically bond to the SOF structure are exceptionally chemically and mechanically robust photochromic materials. Such photochromic SOF materials demonstrate many superior properties, such as high number of reversible color change processes, to available polymeric alternatives.

The term electroactive refers, for example, to the property to transport electrical charge (electrons and/or holes). Electroactive materials include conductors, semiconductors, and charge transport materials. Conductors are defined as materials that readily transport electrical charge in the presence of a potential difference. Semiconductors are defined as materials do not inherently conduct charge but may become conductive in the presence of a potential difference and an applied stimuli, such as, for example, an electric field, electromagnetic radiation, heat, and the like. Charge transport materials are defined as materials that can transport charge when charge is injected from another material such as, for example, a dye, pigment, or metal in the presence of a potential difference.

Conductors may be further defined as materials that give a signal using a potentiometer from about 0.1 to about $10^7$ S/cm.

Semiconductors may be further defined as materials that give a signal using a potentiometer from about $10^{-6}$ to about $10^4$ S/cm in the presence of applied stimuli such as, for example an electric field, electromagnetic radiation, heat, and the like. Alternatively, semiconductors may be defined as materials having electron and/or hole mobility measured using time-of-flight techniques in the range of $10^0$ to about $10^6$ cm$^2$V$^{-1}$s$^{-1}$ when exposed to applied stimuli such as, for example an electric field, electromagnetic radiation, heat, and the like.

Charge transport materials may be further defined as materials that have electron and/or hole mobility measured using time-of-flight techniques in the range of $10^{-10}$ to about $10^6$ cm$^2$V$^{-1}$s$^{-1}$. It should be noted that under some circumstances charge transport materials may be also classified as semiconductors.

SOFs with hydrophobic added functionality may be prepared by using molecular building blocks with inclined hydrophobic properties and/or have a rough, textured, or porous surface on the sub-micron to micron scale. A paper describing materials having a rough, textured, or porous surface on the sub-micron to micron scale being hydrophobic was authored by Cassie and Baxter (Cassie, A. B. D.; Baxter, S. *Trans. Faraday Soc.*, 1944, 40, 546).

Molecular building blocks comprising or bearing highly-fluorinated segments have inclined hydrophobic properties and may lead to SOFs with hydrophobic added functionality. Highly-fluorinated segments are defined as the number of fluorine atoms present on the segment(s) divided by the number of hydrogen atoms present on the segment(s) being greater than one. Fluorinated segments, which are not highly-fluorinated segments may also lead to SOFs with hydrophobic added functionality.

The above-mentioned fluorinated segments may include, for example, tetrafluorohydroquinone, perfluoroadipic acid hydrate, 4,4'-(hexafluoroisopropylidene)diphthalic anhydride, 4,4'-(hexafluoroisopropylidene)diphenol, and the like.

SOFs having a rough, textured, or porous surface on the sub-micron to micron scale may also be hydrophobic. The rough, textured, or porous SOF surface can result from dangling functional groups present on the film surface or from the structure of the SOF. The type of pattern and degree of patterning depends on the geometry of the molecular building blocks and the linking chemistry efficiency. The feature size that leads to surface roughness or texture is from about 100 nm to about 10 µm, such as from about 500 nm to about 5 µm.

SOFs with hydrophilic added functionality may be prepared by using molecular building blocks with inclined hydrophilic properties and/or comprising polar linking groups.

Molecular building blocks comprising segments bearing polar substituents have inclined hydrophilic properties and may lead to SOFs with hydrophilic added functionality. The term polar substituents refers, for example, to substituents that can form hydrogen bonds with water and include, for example, hydroxyl, amino, ammonium, and carbonyl (such as ketone, carboxylic acid, ester, amide, carbonate, urea).

SOFs with electroactive added functionality may be prepared by using molecular building blocks with inclined electroactive properties and/or be electroactive resulting from the assembly of conjugated segments and linkers. The following sections describe molecular building blocks with inclined hole transport properties, inclined electron transport properties, and inclined semiconductor properties.

SOFs with hole transport added functionality may be obtained by selecting segment cores such as, for example, triarylamines, hydrazones (U.S. Pat. No. 7,202,002 B2 to Tokarski et al.), and enamines (U.S. Pat. No. 7,416,824 B2 to Kondoh et al.) with the following general structures:

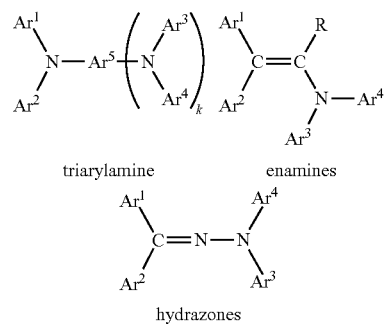

triarylamine    enamines hydrazones

The segment core comprising a triarylamine being represented by the following general formula:

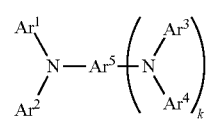

wherein $Ar^1$, $Ar^2$, $Ar^3$, $Ar^4$ and $Ar^5$ each independently represents a substituted or unsubstituted aryl group, or $Ar^5$ independently represents a substituted or unsubstituted arylene group, and k represents 0 or 1, wherein at least two of $Ar^1$, $Ar^2$, $Ar^3$, $Ar^4$ and $Ar^5$ comprises a Fg (previously defined). $Ar^5$ may be further defined as, for example, a substituted phenyl ring, substituted/unsubstituted phenylene, substituted/unsubstituted monovalently linked aromatic rings such as biphenyl, terphenyl, and the like, or substituted/unsubstituted fused aromatic rings such as naphthyl, anthranyl, phenanthryl, and the like.

Segment cores comprising arylamines with hole transport added functionality include, for example, aryl amines such as triphenylamine, N,N,N',N'-tetraphenyl-(1,1'-biphenyl)-4,4'-diamine, N,N'-diphenyl-N,N'-bis(3-methylphenyl)-(1,1'-biphenyl)-4,4'-diamine, N,N'-bis(4-butylphenyl)-N,N'-diphenyl-[p-terphenyl]-4,4''-diamine; hydrazones such as N-phenyl-N-methyl-3-(9-ethyl)carbazyl hydrazone and 4-diethyl amino benzaldehyde-1,2-diphenyl hydrazone; and oxadiazoles such as 2,5-bis(4-N,N'-diethylaminophenyl)-1,2,4-oxadiazole, stilbenes, and the like.

Molecular building blocks comprising triarylamine core segments with inclined hole transport properties may be derived from the list of chemical structures including, for example, those listed below:

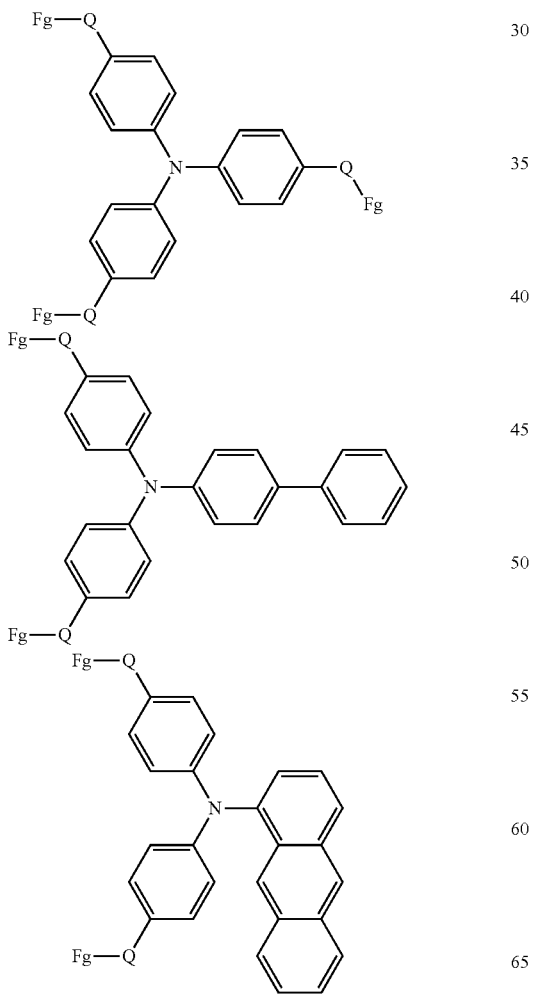

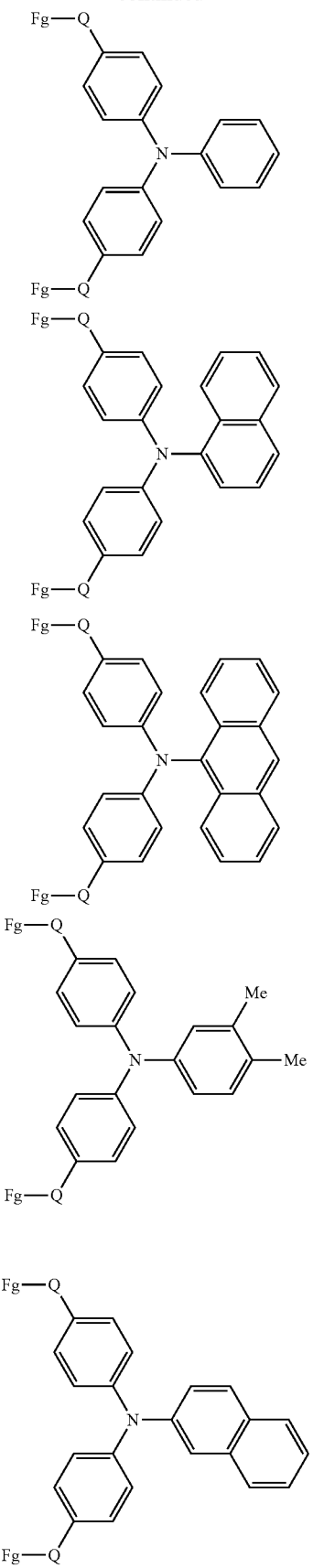

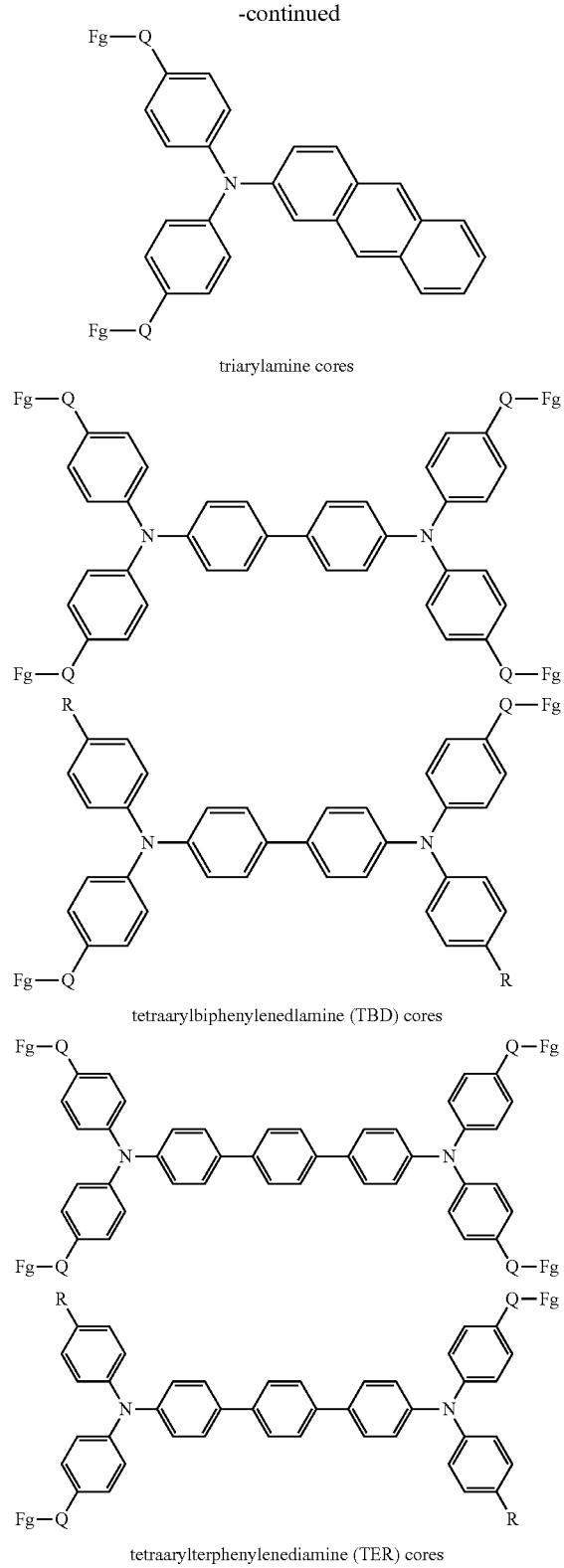

triarylamine cores tetraarylbiphenylenedlamine (TBD) cores tetraarylterphenylenediamine (TER) cores The segment core comprising a hydrazone being represented by the following general formula:

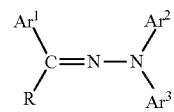

wherein $Ar^1$, $Ar^2$, and $Ar^3$ each independently represents an aryl group optionally containing one or more substituents, and R represents a hydrogen atom, an aryl group, or an alkyl group optionally containing a substituent; wherein at least two of $Ar^1$, $Ar^2$, and $Ar^3$ comprises a Fg (previously defined); and a related oxadiazole being represented by the following general formula:

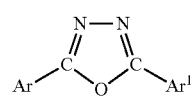

wherein Ar and $Ar^1$ each independently represent an aryl group that comprises a Fg (previously defined).

Molecular building blocks comprising hydrazone and oxadiazole core segments with inclined hole transport properties may be derived from the list of chemical structures including, for example, those listed below:

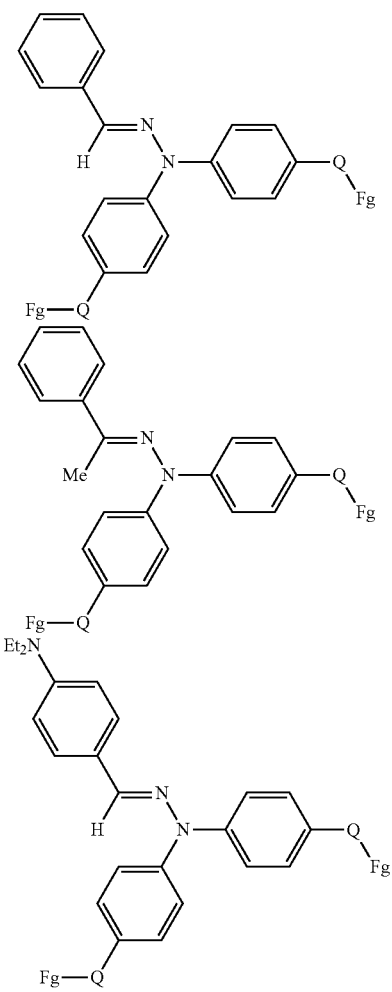

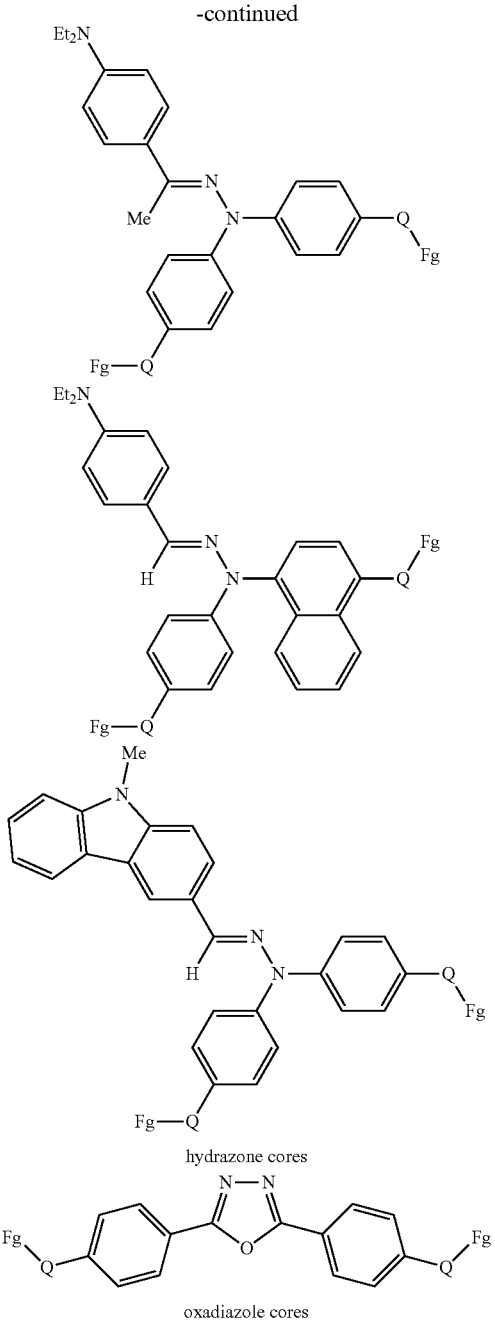

hydrazone cores

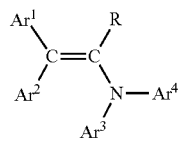

oxadiazole cores

The segment core comprising an enamine being represented by the following general formula:

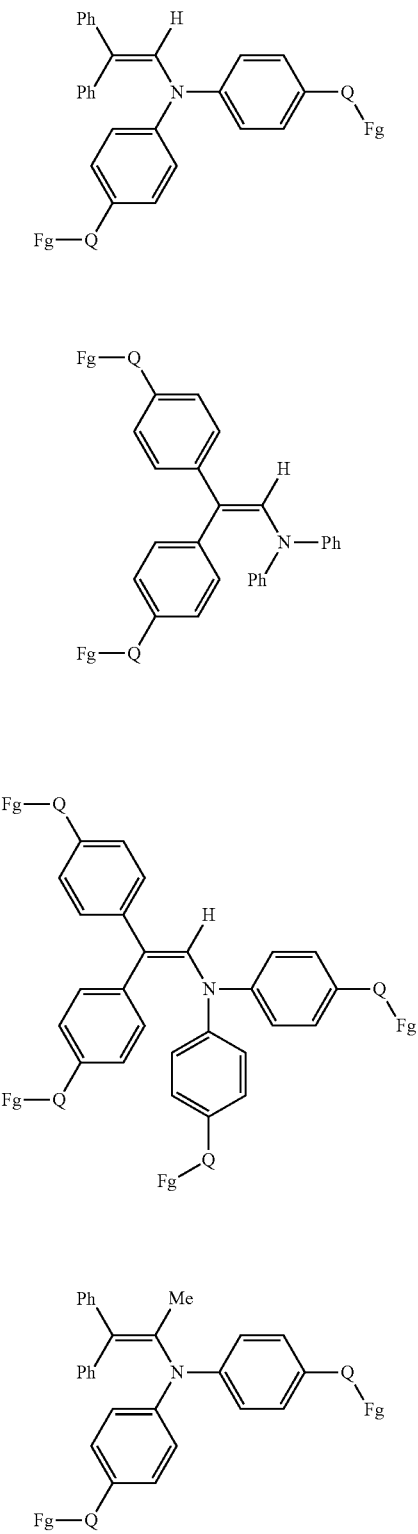

wherein $Ar^1$, $Ar^2$, $Ar^3$, and $Ar^4$ each independently represents an aryl group that optionally contains one or more substituents or a heterocyclic group that optionally contains one or more substituents, and R represents a hydrogen atom, an aryl group, or an alkyl group optionally containing a substituent; wherein at least two of $Ar^1$, $Ar^2$, $Ar^3$, and $Ar^4$ comprises a Fg (previously defined).

Molecular building blocks comprising enamine core segments with inclined hole transport properties may be derived from the list of chemical structures including, for example, those listed below:

-continued

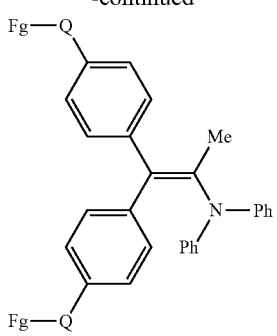

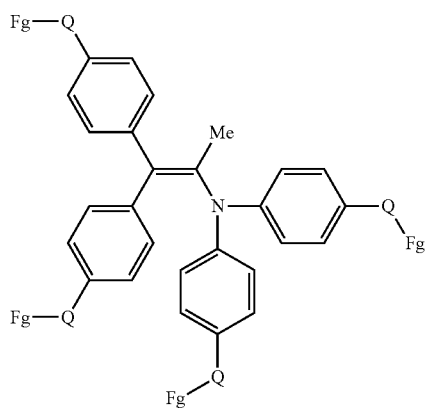

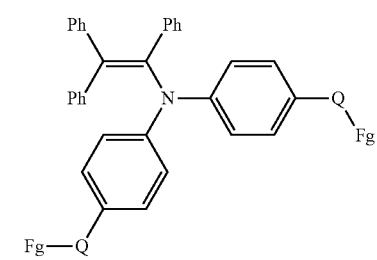

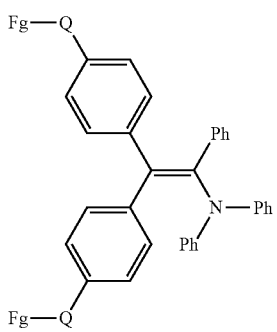

-continued

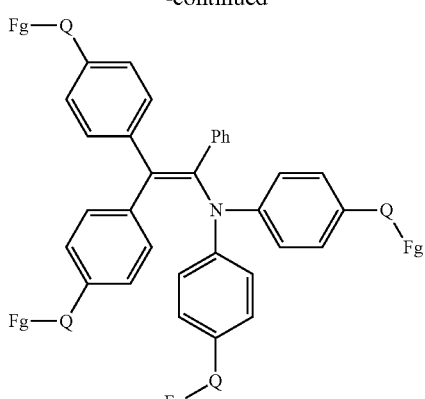

enamine cores

SOFs with electron transport added functionality may be obtained by selecting segment cores comprising, for example, nitrofluorenones, 9-fluorenylidene malonitriles, diphenoquinones, and naphthalenetetracarboxylic diimides with the following general structures:

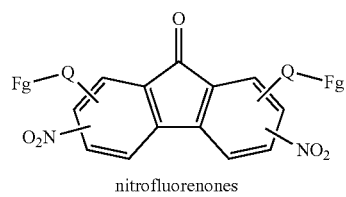

nitrofluorenones

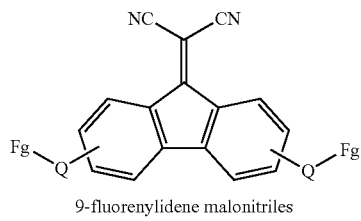

9-fluorenylidene malonitriles

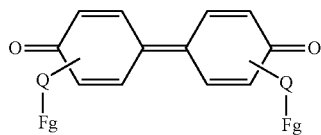

diphenoquinones

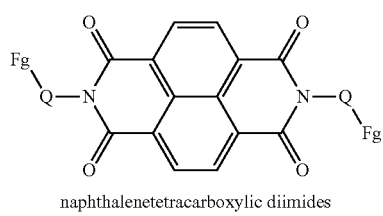

naphthalenetetracarboxylic diimides

It should be noted that the carbonyl groups of diphenylquinones could also act as Fgs in the SOF forming process.

SOFs with semiconductor added functionality may be obtained by selecting segment cores such as, for example, acenes, thiophenes/oligothiophenes/fused thiophenes, perylene bisimides, or tetrathiofulvalenes, and derivatives thereof with the following general structures:

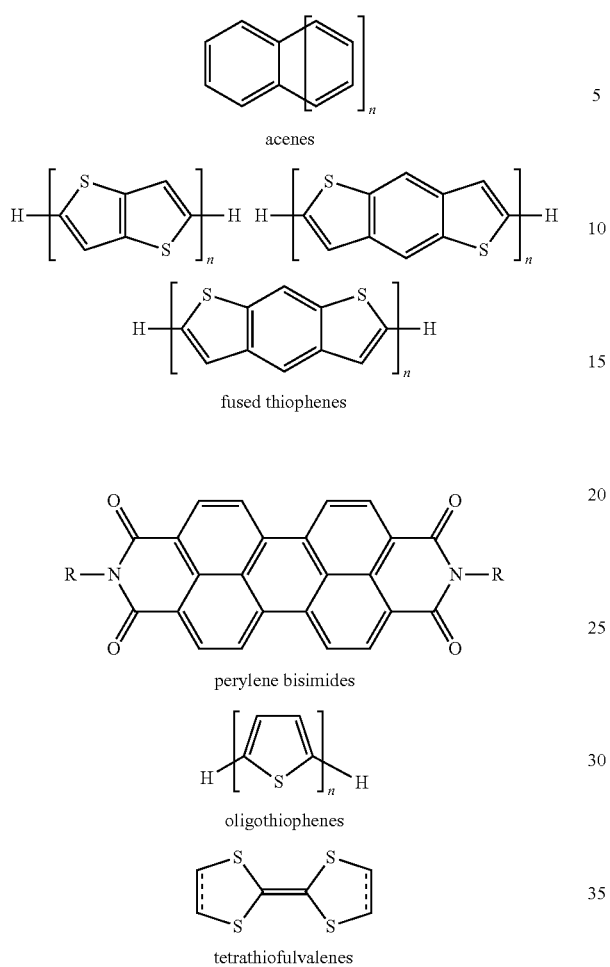

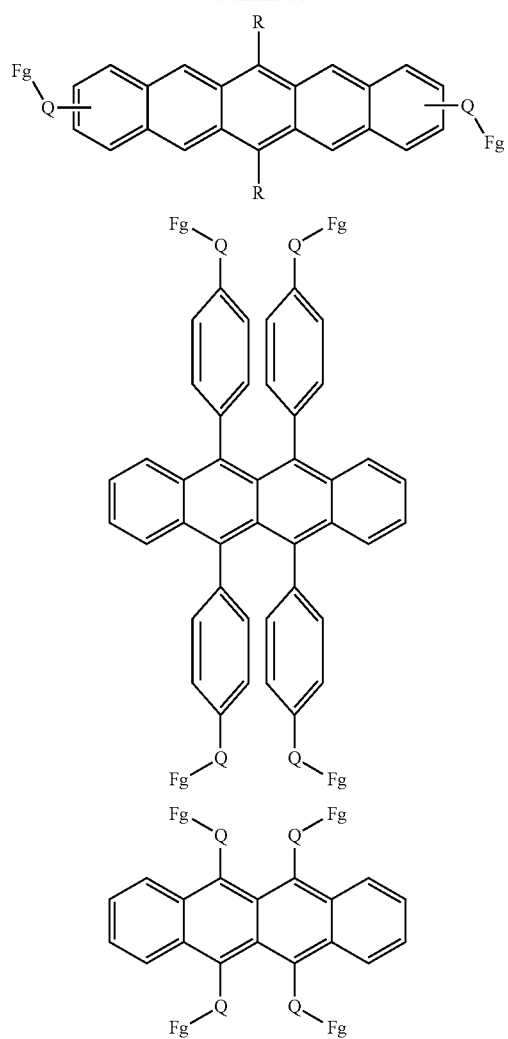

The SOF may be a p-type semiconductor, n-type semiconductor or ambipolar semiconductor. The SOF semiconductor type depends on the nature of the molecular building blocks. Molecular building blocks that possess an electron donating property such as alkyl, alkoxy, aryl, and amino groups, when present in the SOF, may render the SOF a p-type semiconductor. Alternatively, molecular building blocks that are electron withdrawing such as cyano, nitro, fluoro, fluorinated alkyl, and fluorinated aryl groups may render the SOF into the n-type semiconductor.

Molecular building blocks comprising acene core segments with inclined semiconductor properties may be derived from the list of chemical structures including, for example, those listed below:

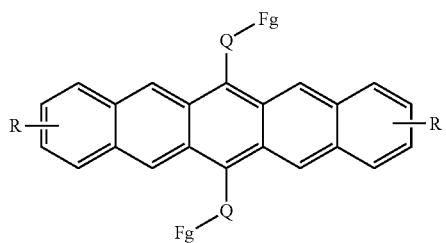

Molecular building blocks comprising thiophene/oligothiophene/fused thiophene core segments with inclined semiconductor properties may be derived from the list of chemical structures including, for example, those listed below:

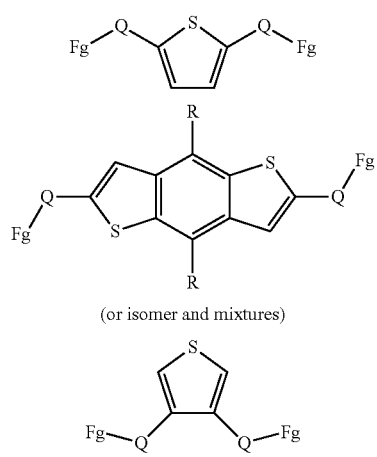

(or isomer and mixtures)

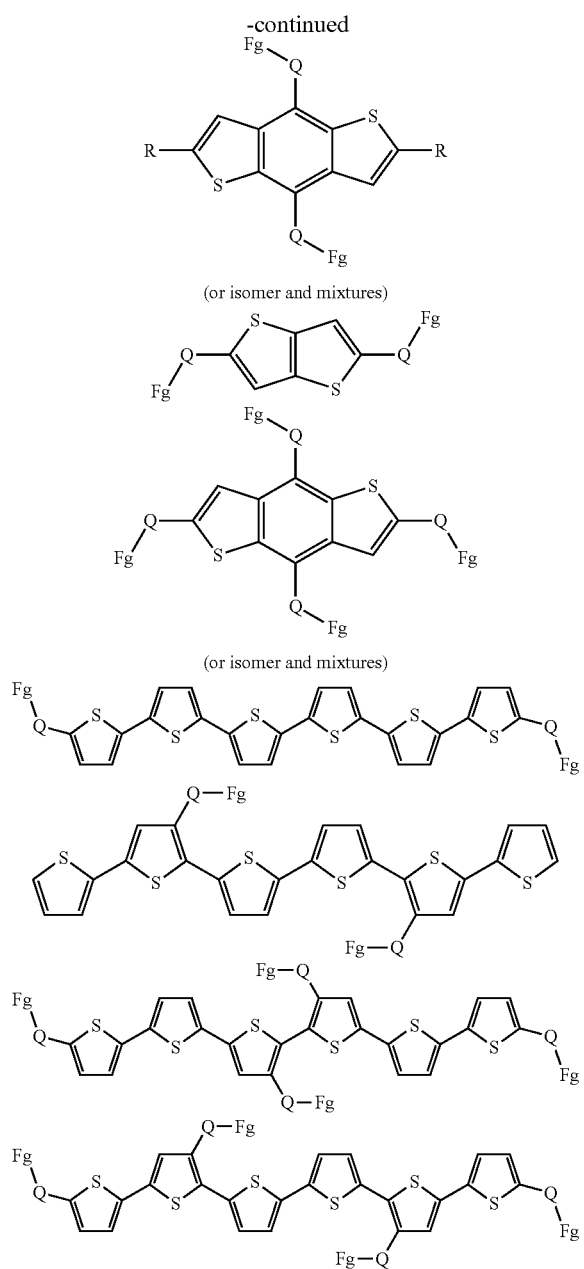

(or isomer and mixtures)

(or isomer and mixtures)

Examples of molecular building blocks comprising perylene bisimide core segments with inclined semiconductor properties may be derived from the chemical structure below:

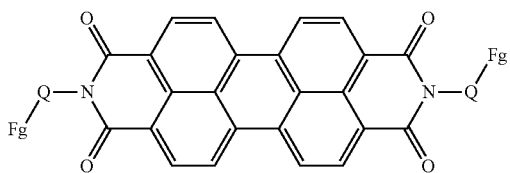

Molecular building blocks comprising tetrathiofulvalene core segments with inclined semiconductor properties may be derived from the list of chemical structures including, for example, those listed below:

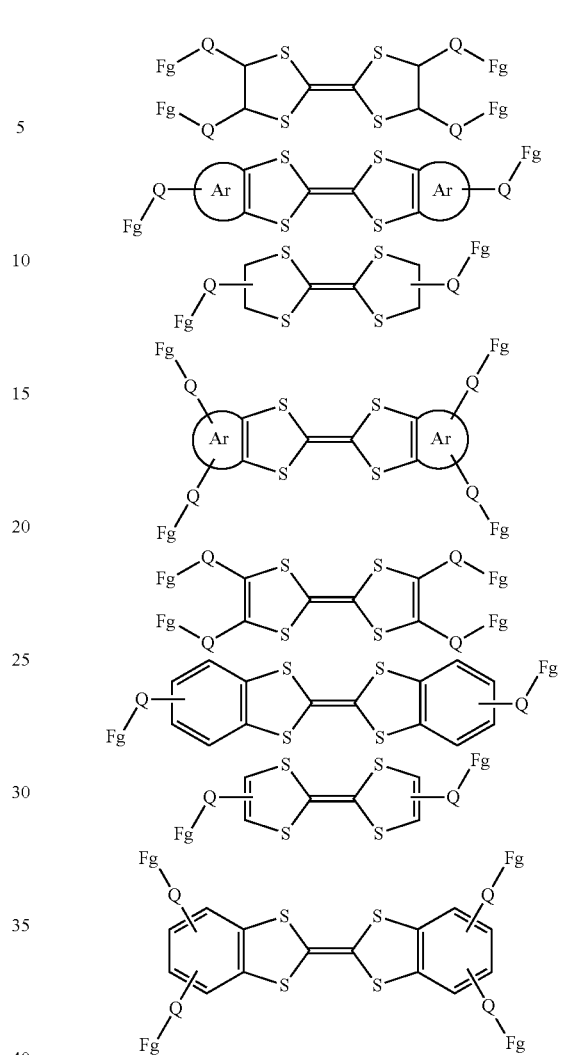

wherein Ar each independently represents an aryl group that optionally contains one or more substituents or a heterocyclic group that optionally contains one or more substituents.

Similarly, the electroactivity of SOFs prepared by these molecular building blocks will depend on the nature of the segments, nature of the linkers, and how the segments are orientated within the SOF. Linkers that favor preferred orientations of the segment moieties in the SOF are expected to lead to higher electroactivity.

Process for Preparing a Capped Structured Organic Film (SOF)

The process for making capped SOFs (which may be referred to as an "SOF" below) typically comprises a similar number of activities or steps (set forth below) that are used to make a non-capped SOF. The capping unit may be added during either step a, b or c, depending the desired distribution of the capping unit in the resulting SOF. For example, if it is desired that the capping unit distribution is substantially uniform over the resulting SOF, the capping unit may be added during step a. Alternatively, if, for example, a more heterogeneous distribution of the capping unit is desired, adding the capping unit (such as by spraying it on the film formed during step b or during the promotion step of step c) may occur during steps b and c.

The process for making SOFs typically comprises a number of activities or steps (set forth below) that may be performed in any suitable sequence or where two or more activities are performed simultaneously or in close proximity in time:

A process for preparing a structured organic film comprising:
(a) preparing a liquid-containing reaction mixture comprising a plurality of molecular building blocks each comprising a segment and a number of functional groups;
(b) depositing the reaction mixture as a wet film;
(c) promoting a change of the wet film including the molecular building blocks to a dry film comprising the SOF comprising a plurality of the segments and a plurality of linkers arranged as a covalent organic framework, wherein at a macroscopic level the covalent organic framework is a film;
(d) optionally removing the SOF from the coating substrate to obtain a free-standing SOF;
(e) optionally processing the free-standing SOF into a roll;
(f) optionally cutting and seaming the SOF into a belt; and
(g) optionally performing the above SOF formation process (es) upon an SOF (which was prepared by the above SOF formation process(es)) as a substrate for subsequent SOF formation process(es).

The above activities or steps may be conducted at atmospheric, super atmospheric, or subatmospheric pressure. The term "atmospheric pressure" as used herein refers to a pressure of about 760 torr. The term "super atmospheric" refers to pressures greater than atmospheric pressure, but less than 20 atm. The term "subatmospheric pressure" refers to pressures less than atmospheric pressure. In an embodiment, the activities or steps may be conducted at or near atmospheric pressure. Generally, pressures of from about 0.1 atm to about 2 atm, such as from about 0.5 atm to about 1.5 atm, or 0.8 atm to about 1.2 atm may be conveniently employed.

Process Action A: Preparation of the Liquid-Containing Reaction Mixture

The reaction mixture comprises a plurality of molecular building blocks that are dissolved, suspended, or mixed in a liquid. The plurality of molecular building blocks may be of one type or two or more types. When one or more of the molecular building blocks is a liquid, the use of an additional liquid is optional. Catalysts may optionally be added to the reaction mixture to enable SOF formation or modify the kinetics of SOF formation during Action C described above. Additives or secondary components may optionally be added to the reaction mixture to alter the physical properties of the resulting SOF.

The reaction mixture components (molecular building blocks, optionally a capping unit, liquid, optionally catalysts, and optionally additives) are combined in a vessel. The order of addition of the reaction mixture components may vary; however, typically the catalyst is added last. In particular embodiments, the molecular building blocks are heated in the liquid in the absence of the catalyst to aid the dissolution of the molecular building blocks. The reaction mixture may also be mixed, stirred, milled, or the like, to ensure even distribution of the formulation components prior to depositing the reaction mixture as a wet film.

In embodiments, the reaction mixture may be heated prior to being deposited as a wet film. This may aid the dissolution of one or more of the molecular building blocks and/or increase the viscosity of the reaction mixture by the partial reaction of the reaction mixture prior to depositing the wet layer. This approach may be used to increase the loading of the molecular building blocks in the reaction mixture.

In particular embodiments, the reaction mixture needs to have a viscosity that will support the deposited wet layer. Reaction mixture viscosities range from about 10 to about 50,000 cps, such as from about 25 to about 25,000 cps or from about 50 to about 1000 cps.

The molecular building block and capping unit loading or "loading" in the reaction mixture is defined as the total weight of the molecular building blocks and optionally the capping units and catalysts divided by the total weight of the reaction mixture. Building block loadings may range from about 3 to 100%, such as from about 5 to about 50%, or from about 15 to about 40%. In the case where a liquid molecular building block is used as the only liquid component of the reaction mixture (i.e. no additional liquid is used), the building block loading would be about 100%. The capping unit loading may be chosen, so as to achieve the desired loading of the capping group. For example, depending on when the capping unit is to be added to the reaction mixture, capping unit loadings may range, by weight, from about 3 to 80%, such as from about 5 to about 50%, or from about 15 to about 40% by weight.

In embodiments, the theoretical upper limit for capping unit loading is the molar amount of capping units that reduces the number of available linking groups to 2 per molecular building block in the liquid SOF formulation. In such a loading, substantial SOF formation may be effectively inhibited by exhausting (by reaction with the respective capping group) the number of available linkable functional groups per molecular building block. For example, in such a situation (where the capping unit loading is in an amount sufficient to ensure that the molar excess of available linking groups is less than 2 per molecular building block in the liquid SOF formulation), oligomers, linear polymers, and molecular building blocks that are fully capped with capping units may predominately form instead of an SOF.

Liquids used in the reaction mixture may be pure liquids, such as solvents, and/or solvent mixtures. Liquids are used to dissolve or suspend the molecular building blocks and catalyst/modifiers in the reaction mixture. Liquid selection is generally based on balancing the solubility/dispersion of the molecular building blocks and a particular building block loading, the viscosity of the reaction mixture, and the boiling point of the liquid, which impacts the promotion of the wet layer to the dry SOF. Suitable liquids may have boiling points from about 30 to about 300° C., such as from about 65° C. to about 250° C., or from about 100° C. to about 180° C.

Liquids can include molecule classes such as alkanes (hexane, heptane, octane, nonane, decane, cyclohexane, cycloheptane, cyclooctane, decalin); mixed alkanes (hexanes, heptanes); branched alkanes (isooctane); aromatic compounds (toluene, o-, m-, p-xylene, mesitylene, nitrobenzene, benzonitrile, butylbenzene, aniline); ethers (benzyl ethyl ether, butyl ether, isoamyl ether, propyl ether); cyclic ethers (tetrahydrofuran, dioxane), esters (ethyl acetate, butyl acetate, butyl butyrate, ethoxyethyl acetate, ethyl propionate, phenyl acetate, methyl benzoate); ketones (acetone, methyl ethyl ketone, methyl isobutylketone, diethyl ketone, chloroacetone, 2-heptanone), cyclic ketones (cyclopentanone, cyclohexanone), amines (1°, 2°, or 3° amines such as butylamine, diisopropylamine, triethylamine, diisoproylethylamine; pyridine); amides (dimethylformamide, N-methylpyrrolidinone, N,N-dimethylformamide); alcohols (methanol, ethanol, n-, i-propanol, n-, i-, t-butanol, 1-methoxy-2-propanol, hexanol, cyclohexanol, 3-pentanol, benzyl alcohol); nitriles (acetonitrile, benzonitrile, butyronitrile), halogenated aromatics (chlorobenzene, dichlorobenzene, hexafluorobenzene), halogenated alkanes (dichloromethane, chloroform, dichloroethylene, tetrachloroethane); and water.

Mixed liquids comprising a first solvent, second solvent, third solvent, and so forth may also be used in the reaction mixture. Two or more liquids may be used to aid the dissolution/dispersion of the molecular building blocks; and/or increase the molecular building block loading; and/or allow a stable wet film to be deposited by aiding the wetting of the substrate and deposition instrument; and/or modulate the promotion of the wet layer to the dry SOF. In embodiments, the second solvent is a solvent whose boiling point or vapor-pressure curve or affinity for the molecular building blocks differs from that of the first solvent. In embodiments, a first solvent has a boiling point higher than that of the second solvent. In embodiments, the second solvent has a boiling point equal to or less than about 100° C., such as in the range of from about 30° C. to about 100° C., or in the range of from about 40° C. to about 90° C., or about 50° C. to about 80° C.

In embodiments, the first solvent, or higher boiling point solvent, has a boiling point equal to or greater than about 65° C., such as in the range of from about 80° C. to about 300° C., or in the range of from about 100° C. to about 250° C., or about 100° C. to about 180° C. The higher boiling point solvent may include, for example, the following (the value in parentheses is the boiling point of the compound): hydrocarbon solvents such as amylbenzene (202° C.), isopropylbenzene (152° C.), 1,2-diethylbenzene (183° C.), 1,3-diethylbenzene (181° C.), 1,4-diethylbenzene (184° C.), cyclohexylbenzene (239° C.), dipentene (177° C.), 2,6-dimethylnaphthalene (262° C.), p-cymene (177° C.), camphor oil (160-185° C.), solvent naphtha (110-200° C.), cis-decalin (196° C.), trans-decalin (187° C.), decane (174° C.), tetralin (207° C.), turpentine oil (153-175° C.), kerosene (200-245° C.), dodecane (216° C.), dodecylbenzene (branched), and so forth; ketone and aldehyde solvents such as acetophenone (201.7° C.), isophorone (215.3° C.), phorone (198-199° C.), methylcyclohexanone (169.0-170.5° C.), methyl n-heptyl ketone (195.3° C.), and so forth; ester solvents such as diethyl phthalate (296.1° C.), benzyl acetate (215.5° C.), γ-butyrolactone (204° C.), dibutyl oxalate (240° C.), 2-ethylhexyl acetate (198.6° C.), ethyl benzoate (213.2° C.), benzyl formate (203° C.), and so forth; diethyl sulfate (208° C.), sulfolane (285° C.), and halohydrocarbon solvents; etherified hydrocarbon solvents; alcohol solvents; ether/acetal solvents; polyhydric alcohol solvents; carboxylic anhydride solvents; phenolic solvents; water; and silicone solvents.

The ratio of the mixed liquids may be established by one skilled in the art. The ratio of liquids a binary mixed liquid may be from about 1:1 to about 99:1, such as from about 1:10 to about 10:1, or about 1:5 to about 5:1, by volume. When n liquids are used, with n ranging from about 3 to about 6, the amount of each liquid ranges from about 1% to about 95% such that the sum of each liquid contribution equals 100%.

In embodiments, the mixed liquid comprises at least a first and a second solvent with different boiling points. In further embodiments, the difference in boiling point between the first and the second solvent may be from about nil to about 150° C., such as from nil to about 50° C. For example, the boiling point of the first solvent may exceed the boiling point of the second solvent by about 1° C. to about 100° C., such as by about 5° C. to about 100° C., or by about 10° C. to about 50° C. The mixed liquid may comprise at least a first and a second solvent with different vapor pressures, such as combinations of high vapor pressure solvents and/or low vapor pressure solvents. The term "high vapor pressure solvent" refers to, for example, a solvent having a vapor pressure of at least about 1 kPa, such as about 2 kPa, or about 5 kPa. The term "low vapor pressure solvent" refers to, for example, a solvent having a vapor pressure of less than about 1 kPa, such as about 0.9 kPa, or about 0.5 kPa. In embodiments, the first solvent may be a low vapor pressure solvent such as, for example, terpineol, diethylene glycol, ethylene glycol, hexylene glycol, N-methyl-2-pyrrolidone, and tri(ethylene glycol) dimethyl ether. A high vapor pressure solvent allows rapid removal of the solvent by drying and/or evaporation at temperatures below the boiling point. High vapor pressure solvents may include, for example, acetone, tetrahydrofuran, toluene, xylene, ethanol, methanol, 2-butanone and water.

In embodiments where mixed liquids comprising a first solvent, second solvent, third solvent, and so forth are used in the reaction mixture, promoting the change of the wet film and forming the dry SOF may comprise, for example, heating the wet film to a temperature above the boiling point of the reaction mixture to form the dry SOF; or heating the wet film to a temperature above the boiling point of the second solvent (below the temperature of the boiling point of the first solvent) in order to remove the second solvent while substantially leaving the first solvent and then after substantially removing the second solvent, removing the first solvent by heating the resulting composition at a temperature either above or below the boiling point of the first solvent to form the dry SOF; or heating the wet film below the boiling point of the second solvent in order to remove the second solvent (which is a high vapor pressure solvent) while substantially leaving the first solvent and, after removing the second solvent, removing the first solvent by heating the resulting composition at a temperature either above or below the boiling point of the first solvent to form the dry SOF.

The term "substantially removing" refers to, for example, the removal of at least 90% of the respective solvent, such as about 95% of the respective solvent. The term "substantially leaving" refers to, for example, the removal of no more than 2% of the respective solvent, such as removal of no more than 1% of the respective solvent.

These mixed liquids may be used to slow or speed up the rate of conversion of the wet layer to the SOF in order to manipulate the characteristics of the SOFs. For example, in condensation and addition/elimination linking chemistries, liquids such as water, 1°, 2°, or 3° alcohols (such as methanol, ethanol, propanol, isopropanol, butanol, 1-methoxy-2-propanol, tert-butanol) may be used.

Optionally a catalyst may be present in the reaction mixture to assist the promotion of the wet layer to the dry SOF. Selection and use of the optional catalyst depends on the functional groups on the molecular building blocks. Catalysts may be homogeneous (dissolved) or heterogeneous (undissolved or partially dissolved) and include Brönsted acids (HCl(aq), acetic acid, p-toluenesulfonic acid, amine-protected p-toluenesulfonic acid such as pyrridium p-toluenesulfonate, trifluoroacetic acid); Lewis acids (boron trifluoroetherate, aluminum trichloride); Brönsted bases (metal hydroxides such as sodium hydroxide, lithium hydroxide, potassium hydroxide; 1°, 2°, or 3° amines such as butylamine, diisopropylamine, triethylamine, diisoproylethylamine); Lewis bases (N,N-dimethyl-4-aminopyridine); metals (Cu bronze); metal salts ($FeCl_3$, $AuCl_3$); and metal complexes (ligated palladium complexes, ligated ruthenium catalysts). Typical catalyst loading ranges from about 0.01% to about 25%, such as from about 0.1% to about 5% of the molecular building block loading in the reaction mixture. The catalyst may or may not be present in the final SOF composition.

Optionally additives or secondary components, such as dopants, may be present in the reaction mixture and wet layer. Such additives or secondary components may also be integrated into a dry SOF. Additives or secondary components can be homogeneous or heterogeneous in the reaction mixture and wet layer or in a dry SOF. In contrast to capping units, the terms "additive" or "secondary component," refer, for example, to atoms or molecules that are not covalently bound in the SOF, but are randomly distributed in the composition. Suitable secondary components and additives are described in U.S. patent application Ser. No. 12/716,324, entitled "Composite Structured Organic Films," the disclosure of which is totally incorporated herein by reference in its entirety.

In embodiments, the secondary components may have similar or disparate properties to accentuate or hybridize (synergistic effects or ameliorative effects as well as the ability to attenuate inherent or inclined properties of the capped SOF) the intended property of the capped SOF to enable it to meet performance targets. For example, doping the capped SOFs with antioxidant compounds will extend the life of the capped SOF by preventing chemical degradation pathways. Additionally, additives maybe added to improve the morphological properties of the capped SOF by tuning the reaction occurring during the promotion of the change of the reaction mixture to faun the capped SOF.

Process Action B: Depositing the Reaction Mixture as a Wet Film

The reaction mixture may be applied as a wet film to a variety of substrates using a number of liquid deposition techniques. The thickness of the SOF is dependant on the thickness of the wet film and the molecular building block loading in the reaction mixture. The thickness of the wet film is dependent on the viscosity of the reaction mixture and the method used to deposit the reaction mixture as a wet film.

Substrates include, for example, polymers, papers, metals and metal alloys, doped and undoped forms of elements from Groups of the periodic table, metal oxides, metal chalcogenides, and previously prepared SOFs or capped SOFs. Examples of polymer film substrates include polyesters, polyolefins, polycarbonates, polystyrenes, polyvinylchloride, block and random copolymers thereof, and the like. Examples of metallic surfaces include metallized polymers, metal foils, metal plates; mixed material substrates such as metals patterned or deposited on polymer, semiconductor, metal oxide, or glass substrates. Examples of substrates comprised of doped and undoped elements from Groups III-VI of the periodic table include, aluminum, silicon, silicon n-doped with phosphorous, silicon p-doped with boron, tin, gallium arsenide, lead, gallium indium phosphide, and indium. Examples of metal oxides include silicon dioxide, titanium dioxide, indium tin oxide, tin dioxide, selenium dioxide, and alumina. Examples of metal chalcogenides include cadmium sulfide, cadmium telluride, and zinc selenide. Additionally, it is appreciated that chemically treated or mechanically modified forms of the above substrates remain within the scope of surfaces which may be coated with the reaction mixture.

In embodiments, the substrate may be composed of, for example, silicon, glass plate, plastic film or sheet. For structurally flexible devices, a plastic substrate such as polyester, polycarbonate, polyimide sheets and the like may be used. The thickness of the substrate may be from around 10 micrometers to over 10 millimeters with an exemplary thickness being from about 50 to about 100 micrometers, especially for a flexible plastic substrate, and from about 1 to about 10 millimeters for a rigid substrate such as glass or silicon.

The reaction mixture may be applied to the substrate using a number of liquid deposition techniques including, for example, spin coating, blade coating, web coating, dip coating, cup coating, rod coating, screen printing, ink jet printing, spray coating, stamping and the like. The method used to deposit the wet layer depends on the nature, size, and shape of the substrate and the desired wet layer thickness. The thickness of the wet layer can range from about 10 nm to about 5 mm, such as from about 100 nm to about 1 mm, or from about 1 μm to about 500 μm.

In embodiments, the capping unit and/or secondary component may be introduced following completion of the above described process action B. The incorporation of the capping unit and/or secondary component in this way may be accomplished by any means that serves to distribute the capping unit and/or secondary component homogeneously, heterogeneously, or as a specific pattern over the wet film. Following introduction of the capping unit and/or secondary component subsequent process actions may be carried out resuming with process action C.

For example, following completion of process action B (i.e., after the reaction mixture may be applied to the substrate), capping unit(s) and/or secondary components (dopants, additives, etc.) may be added to the wet layer by any suitable method, such as by distributing (e.g., dusting, spraying, pouring, sprinkling, etc, depending on whether the capping unit and/or secondary component is a particle, powder or liquid) the capping unit(s) and/or secondary component on the top the wet layer. The capping units and/or secondary components may be applied to the formed wet layer in a homogeneous or heterogeneous manner, including various patterns, wherein the concentration or density of the capping unit(s) and/or secondary component is reduced in specific areas, such as to form a pattern of alternating bands of high and low concentrations of the capping unit(s) and/or secondary component of a given width on the wet layer. In embodiments, the application of the capping unit(s) and/or secondary component to the top of the wet layer may result in a portion of the capping unit(s) and/or secondary component diffusing or sinking into the wet layer and thereby forming a heterogeneous distribution of capping unit(s) and/or secondary component within the thickness of the SOF, such that a linear or nonlinear concentration gradient may be obtained in the resulting SOF obtained after promotion of the change of the wet layer to a dry SOF. In embodiments, a capping unit(s) and/or secondary component may be added to the top surface of a deposited wet layer, which upon promotion of a change in the wet film, results in an SOF having an heterogeneous distribution of the capping unit(s) and/or secondary component in the dry SOF. Depending on the density of the wet film and the density of the capping unit(s) and/or secondary component, a majority of the capping unit(s) and/or secondary component may end up in the upper half (which is opposite the substrate) of the dry SOF or a majority of the capping unit(s) and/or secondary component may end up in the lower half (which is adjacent to the substrate) of the dry SOF.

Process Action C: Promoting the Change of Wet Film to the Dry SOF

The term "promoting" refers, for example, to any suitable technique to facilitate a reaction of the molecular building blocks, such as a chemical reaction of the functional groups of the building blocks. In the case where a liquid needs to be removed to form the dry film, "promoting" also refers to removal of the liquid. Reaction of the capping units, and molecular building blocks, and removal of the liquid can occur sequentially or concurrently. In embodiments, the capping unit may be added while the promotion of the change of the wet film to the dry SOF is occurring. In certain embodiments, the liquid is also one of the molecular building blocks and is incorporated into the SOF. The term "dry SOF" refers, for example, to substantially dry SOFs (such as capped SOFs), for example, to a liquid content less than about 5% by weight of the SOF, or to a liquid content less than 2% by weight of the SOF.

In embodiments, the dry SOF or a given region of the dry SOF (such as the surface to a depth equal to of about 10% of the thickness of the SOF or a depth equal to of about 5% of the thickness of the SOF, the upper quarter of the SOF, or the regions discussed above) the capping units are present in an amount equal to or greater than about 0.5%, by mole, with respect to the total moles of capping units and segments present, such as from about 1% to about 40%, or from about 2% to 25% by mole, with respect to the total moles of capping units and segments present. For example when the capping units are present in an amount of about 0.5% by mole respect to the total moles of capping units and segments present, there would be about 0.05 mols of capping units and about 9.95 mols of segments present in the sample.

Promoting the wet layer to form a dry SOF may be accomplished by any suitable technique. Promoting the wet layer to form a dry SOF typically involves thermal treatment including, for example, oven drying, infrared radiation (IR), and the like with temperatures ranging from 40 to 350° C. and from 60 to 200° C. and from 85 to 160° C. The total heating time can range from about four seconds to about 24 hours, such as from one minute to 120 minutes, or from three minutes to 60 minutes.

IR promotion of the wet layer to the COF film may be achieved using an IR heater module mounted over a belt transport system. Various types of IR emitters may be used, such as carbon IR emitters or short wave IR emitters (available from Heraeus). Additional exemplary information regarding carbon IR emitters or short wave IR emitters is summarized in the following Table.

| IR lamp | Peak Wavelength | Number of lamps | Module Power (kW) |
| --- | --- | --- | --- |
| Carbon | 2.0 micron | 2 - twin tube | 4.6 |
| Short wave | 1.2-1.4 micron | 3 - twin tube | 4.5 |

Process Action D: Optionally Removing the Capped SOF from the Coating Substrate to Obtain a Free-Standing Capped SOF In embodiments, a free-standing SOF is desired. Free-standing capped SOFs may be obtained when an appropriate low adhesion substrate is used to support the deposition of the wet layer. Appropriate substrates that have low adhesion to the SOF may include, for example, metal foils, metalized polymer substrates, release papers and SOFs, such as SOFs prepared with a surface that has been altered to have a low adhesion or a decreased propensity for adhesion or attachment. Removal of the SOF from the supporting substrate may be achieved in a number of ways by someone skilled in the art. For example, removal of the SOF from the substrate may occur by starting from a corner or edge of the film and optionally assisted by passing the substrate and SOF over a curved surface.

Process Action E: Optionally Processing the Free-Standing SOF into a Roll

Optionally, a free-standing SOF or a SOF supported by a flexible substrate may be processed into a roll. The SOF may be processed into a roll for storage, handling, and a variety of other purposes. The starting curvature of the roll is selected such that the SOF is not distorted or cracked during the rolling process.

Process Action F: Optionally Cutting and Seaming the SOF into a Shape, Such as a Belt The method for cutting and seaming the SOF is similar to that described in U.S. Pat. No. 5,455,136 issued on Oct. 3, 1995 (for polymer films), the disclosure of which is herein totally incorporated by reference. An SOF belt may be fabricated from a single SOF, a multi layer SOF or an SOF sheet cut from a web. Such sheets may be rectangular in shape or any particular shape as desired. All sides of the SOF(s) may be of the same length, or one pair of parallel sides may be longer than the other pair of parallel sides. The SOF(s) may be fabricated into shapes, such as a belt by overlap joining the opposite marginal end regions of the SOF sheet. A seam is typically produced in the overlapping marginal end regions at the point of joining. Joining may be affected by any suitable means. Typical joining techniques include, for example, welding (including ultrasonic), gluing, taping, pressure heat fusing and the like. Methods, such as ultrasonic welding, are desirable general methods of joining flexible sheets because of their speed, cleanliness (no solvents) and production of a thin and narrow seam.

Process Action G: Optionally Using a SOF as a Substrate for Subsequent SOF Formation Processes A SOF may be used as a substrate in the SOF forming process to afford a multi-layered structured organic film. The layers of a multi-layered SOF may be chemically bound in or in physical contact. Chemically bound, multi-layered SOFs are formed when functional groups present on the substrate SOF surface can react with the molecular building blocks present in the deposited wet layer used to form the second structured organic film layer. Multi-layered SOFs in physical contact may not chemically bound to one another.

A SOF substrate may optionally be chemically treated prior to the deposition of the wet layer to enable or promote chemical attachment of a second SOF layer to form a multi-layered structured organic film.

Alternatively, a SOF substrate may optionally be chemically treated prior to the deposition of the wet layer to disable chemical attachment of a second SOF layer (surface pacification) to form a physical contact multi-layered SOF.

Other methods, such as lamination of two or more SOFs, may also be used to prepare physically contacted multi-layered SOFs.

Applications of SOFs

SOFs, such as capped SOFs, may be used in for instance electronic devices such as solar cells, radio frequency identification tags, organic light emitting devices, photoreceptors, thin film transistors and the like.

Application A: SOFs in Photoreceptor Layers

Figure 2:
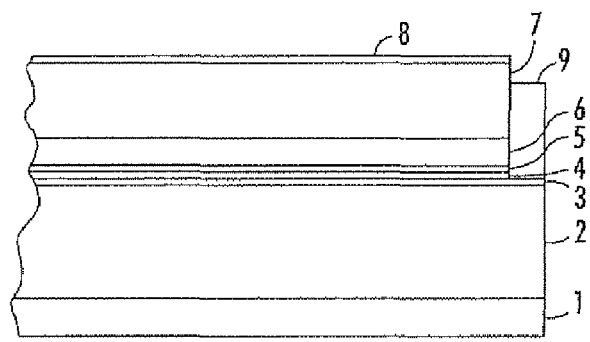
FIG. 2 represents a simplified side view of an exemplary photoreceptor that incorporates a SOF of the present disclosure.
Figure 3:
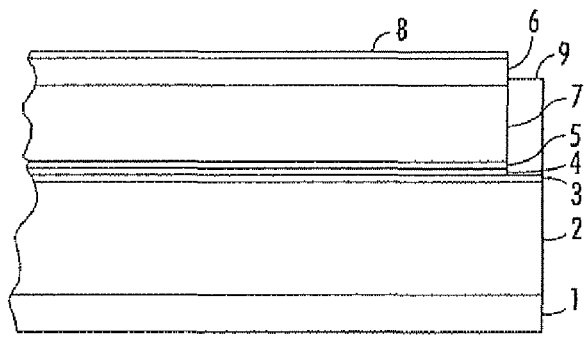
FIG. 3 represents a simplified side view of a second exemplary photoreceptor that incorporates a SOF of the present disclosure.
Figure 4:
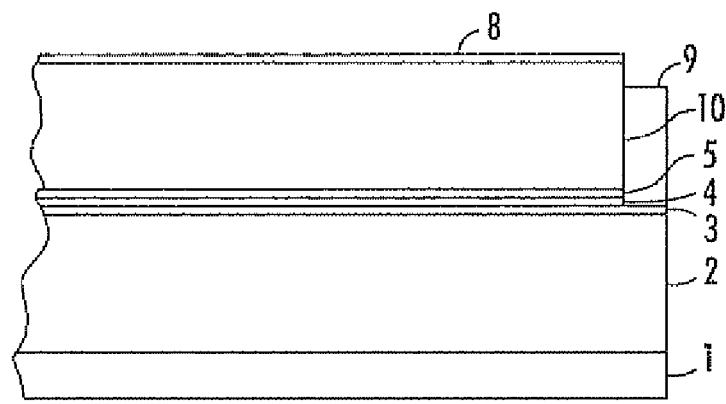
FIG. 4 represents a simplified side view of a third exemplary photoreceptor that incorporates a SOF of the present disclosure.

Representative structures of an electrophotographic imaging member (e.g., a photoreceptor) are shown in FIGS. 2-4. These imaging members are provided with an anti-curl layer 1, a supporting substrate 2, an electrically conductive ground plane 3, a charge blocking layer 4, an adhesive layer 5, a charge generating layer 6, a charge transport layer 7, an overcoating layer 8, and a ground strip 9. In FIG. 4, imaging layer 10 (containing both charge generating material and charge transport material) takes the place of separate charge generating layer 6 and charge transport layer 7.

As seen in the figures, in fabricating a photoreceptor, a charge generating material (CGM) and a charge transport material (CTM) may be deposited onto the substrate surface either in a laminate type configuration where the CGM and CTM are in different layers (e.g., FIGS. 2 and 3) or in a single layer configuration where the CGM and CTM are in the same layer (e.g., FIG. 4). In embodiments, the photoreceptors may be prepared by applying over the electrically conductive layer the charge generation layer 6 and, optionally, a charge transport layer 7. In embodiments, the charge generation layer and, when present, the charge transport layer, may be applied in either order.

Anti Curl Layer

For some applications, an optional anti-curl layer 1, which comprises film-forming organic or inorganic polymers that are electrically insulating or slightly semi-conductive, may be provided. The anti-curl layer provides flatness and/or abrasion resistance.

Anti-curl layer 1 may be formed at the back side of the substrate 2, opposite the imaging layers. The anti-curl layer may include, in addition to the film-forming resin, an adhesion promoter polyester additive. Examples of film-forming resins useful as the anti-curl layer include, but are not limited to, polyacrylate, polystyrene, poly(4,4'-isopropylidene diphenylcarbonate), poly(4,4'-cyclohexylidene diphenylcarbonate), mixtures thereof and the like.

Additives may be present in the anti-curl layer in the range of about 0.5 to about 40 weight percent of the anti-curl layer. Additives include organic and inorganic particles that may further improve the wear resistance and/or provide charge relaxation property. Organic particles include Teflon powder, carbon black, and graphite particles. Inorganic particles include insulating and semiconducting metal oxide particles such as silica, zinc oxide, tin oxide and the like. Another semiconducting additive is the oxidized oligomer salts as described in U.S. Pat. No. 5,853,906. The oligomer salts are oxidized N,N,N',N'-tetra-p-tolyl-4,4'-biphenyldiamine salt.

Typical adhesion promoters useful as additives include, but are not limited to, duPont 49,000 (duPont), Vitel PE-100, Vitel PE-200, Vitel PE-307 (Goodyear), mixtures thereof and the like. Usually from about 1 to about 15 weight percent adhesion promoter is selected for film-forming resin addition, based on the weight of the film-forming resin.

The thickness of the anti-curl layer is typically from about 3 micrometers to about 35 micrometers, such as from about 10 micrometers to about 20 micrometers, or about 14 micrometers.

The anti-curl coating may be applied as a solution prepared by dissolving the film-forming resin and the adhesion promoter in a solvent such as methylene chloride. The solution may be applied to the rear surface of the supporting substrate (the side opposite the imaging layers) of the photoreceptor device, for example, by web coating or by other methods known in the art. Coating of the overcoat layer and the anti-curl layer may be accomplished simultaneously by web coating onto a multilayer photoreceptor comprising a charge transport layer, charge generation layer, adhesive layer, blocking layer, ground plane and substrate. The wet film coating is then dried to produce the anti-curl layer 1.

The Supporting Substrate

As indicated above, the photoreceptors are prepared by first providing a substrate 2, i.e., a support. The substrate may be opaque or substantially transparent and may comprise any additional suitable material(s) having given required mechanical properties, such as those described in U.S. Pat. Nos. 4,457,994; 4,871,634; 5,702,854; 5,976,744; and 7,384,717 the disclosures of which are incorporated herein by reference in their entireties.

The substrate may comprise a layer of electrically non-conductive material or a layer of electrically conductive material, such as an inorganic or organic composition. If a non-conductive material is employed, it may be necessary to provide an electrically conductive ground plane over such non-conductive material. If a conductive material is used as the substrate, a separate ground plane layer may not be necessary.

The substrate may be flexible or rigid and may have any of a number of different configurations, such as, for example, a sheet, a scroll, an endless flexible belt, a web, a cylinder, and the like. The photoreceptor may be coated on a rigid, opaque, conducting substrate, such as an aluminum drum.

Various resins may be used as electrically non-conducting materials, including, for example, polyesters, polycarbonates, polyamides, polyurethanes, and the like. Such a substrate may comprise a commercially available biaxially oriented polyester known as MYLAR™, available from E. I. duPont de Nemours & Co., MELINEX™, available from ICI Americas Inc., or HOSTAPHAN™, available from American Hoechst Corporation. Other materials of which the substrate may be comprised include polymeric materials, such as polyvinyl fluoride, available as TEDLAR™ from E. I. duPont de Nemours & Co., polyethylene and polypropylene, available as MARLEX™ from Phillips Petroleum Company, polyphenylene sulfide, RYTON™ available from Phillips Petroleum Company, and polyimides, available as KAPTON™ from E. I. duPont de Nemours & Co. The photoreceptor may also be coated on an insulating plastic drum, provided a conducting ground plane has previously been coated on its surface, as described above. Such substrates may either be seamed or seamless.

When a conductive substrate is employed, any suitable conductive material may be used. For example, the conductive material can include, but is not limited to, metal flakes, powders or fibers, such as aluminum, titanium, nickel, chromium, brass, gold, stainless steel, carbon black, graphite, or the like, in a binder resin including metal oxides, sulfides, silicides, quaternary ammonium salt compositions, conductive polymers such as polyacetylene or its pyrolysis and molecular doped products, charge transfer complexes, and polyphenyl silane and molecular doped products from polyphenyl silane. A conducting plastic drum may be used, as well as the conducting metal drum made from a material such as aluminum.

The thickness of the substrate depends on numerous factors, including the required mechanical performance and economic considerations. The thickness of the substrate is typically within a range of from about 65 micrometers to about 150 micrometers, such as from about 75 micrometers to about 125 micrometers for optimum flexibility and minimum induced surface bending stress when cycled around small diameter rollers, e.g., 19 mm diameter rollers. The substrate for a flexible belt may be of substantial thickness, for example, over 200 micrometers, or of minimum thickness, for example, less than 50 micrometers, provided there are no adverse effects on the final photoconductive device. Where a drum is used, the thickness should be sufficient to provide the necessary rigidity. This is usually about 1-6 mm.

The surface of the substrate to which a layer is to be applied may be cleaned to promote greater adhesion of such a layer. Cleaning may be effected, for example, by exposing the surface of the substrate layer to plasma discharge, ion bombardment, and the like. Other methods, such as solvent cleaning, may also be used.

Regardless of any technique employed to form a metal layer, a thin layer of metal oxide generally forms on the outer surface of most metals upon exposure to air. Thus, when other layers overlying the metal layer are characterized as "contiguous" layers, it is intended that these overlying contiguous layers may, in fact, contact a thin metal oxide layer that has formed on the outer surface of the oxidizable metal layer.

The Electrically Conductive Ground Plane

As stated above, in embodiments, the photoreceptors prepared comprise a substrate that is either electrically conductive or electrically non-conductive. When a non-conductive substrate is employed, an electrically conductive ground plane 3 must be employed, and the ground plane acts as the conductive layer. When a conductive substrate is employed, the substrate may act as the conductive layer, although a conductive ground plane may also be provided.

If an electrically conductive ground plane is used, it is positioned over the substrate. Suitable materials for the electrically conductive ground plane include, for example, aluminum, zirconium, niobium, tantalum, vanadium, hafnium, titanium, nickel, stainless steel, chromium, tungsten, molybdenum, copper, and the like, and mixtures and alloys thereof. In embodiments, aluminum, titanium, and zirconium may be used.

The ground plane may be applied by known coating techniques, such as solution coating, vapor deposition, and sputtering. A method of applying an electrically conductive ground plane is by vacuum deposition. Other suitable methods may also be used.

In embodiments, the thickness of the ground plane may vary over a substantially wide range, depending on the optical transparency and flexibility desired for the electrophotoconductive member. For example, for a flexible photoresponsive imaging device, the thickness of the conductive layer may be between about 20 angstroms and about 750 angstroms; such as, from about 50 angstroms to about 200 angstroms for an optimum combination of electrical conductivity, flexibility, and light transmission. However, the ground plane can, if desired, be opaque.

The Charge Blocking Layer

After deposition of any electrically conductive ground plane layer, a charge blocking layer 4 may be applied thereto. Electron blocking layers for positively charged photoreceptors permit holes from the imaging surface of the photoreceptor to migrate toward the conductive layer. For negatively charged photoreceptors, any suitable hole blocking layer capable of forming a barrier to prevent hole injection from the conductive layer to the opposite photoconductive layer may be utilized.

If a blocking layer is employed, it may be positioned over the electrically conductive layer. The term "over," as used herein in connection with many different types of layers, should be understood as not being limited to instances wherein the layers are contiguous. Rather, the term "over" refers, for example, to the relative placement of the layers and encompasses the inclusion of unspecified intermediate layers.

The blocking layer 4 may include polymers such as polyvinyl butyral, epoxy resins, polyesters, polysiloxanes, polyamides, polyurethanes, and the like; nitrogen-containing siloxanes or nitrogen-containing titanium compounds, such as trimethoxysilyl propyl ethylene diamine, N-beta(aminoethyl) gamma-aminopropyl trimethoxy silane, isopropyl 4-aminobenzene sulfonyl titanate, di(dodecylbenezene sulfonyl) titanate, isopropyl di(4-aminobenzoyl)isostearoyl titanate, isopropyl tri(N-ethyl amino) titanate, isopropyl trianthranil titanate, isopropyl tri(N,N-dimethyl-ethyl amino) titanate, titanium-4-amino benzene sulfonate oxyacetate, titanium 4-aminobenzoate isostearate oxyacetate, gamma-aminobutyl methyl dimethoxy silane, gamma-aminopropyl methyl dimethoxy silane, and gamma-aminopropyl trimethoxy silane, as disclosed in U.S. Pat. Nos. 4,338,387; 4,286,033; and 4,291,110 the disclosures of which are incorporated herein by reference in their entireties.

The blocking layer may be continuous and may have a thickness ranging, for example, from about 0.01 to about 10 micrometers, such as from about 0.05 to about 5 micrometers.

The blocking layer 4 may be applied by any suitable technique, such as spraying, dip coating, draw bar coating, gravure coating, silk screening, air knife coating, reverse roll coating, vacuum deposition, chemical treatment, and the like. For convenience in obtaining thin layers, the blocking layer may be applied in the form of a dilute solution, with the solvent being removed after deposition of the coating by conventional techniques, such as by vacuum, heating, and the like. Generally, a weight ratio of blocking layer material and solvent of between about 0.5:100 to about 30:100, such as about 5:100 to about 20:100, is satisfactory for spray and dip coating.

The present disclosure further provides a method for forming the electrophotographic photoreceptor, in which the charge blocking layer is formed by using a coating solution composed of the grain shaped particles, the needle shaped particles, the binder resin and an organic solvent.

The organic solvent may be a mixture of an azeotropic mixture of $C_{1-3}$ lower alcohol and another organic solvent selected from the group consisting of dichloromethane, chloroform, 1,2-dichloroethane, 1,2-dichloropropane, toluene and tetrahydrofuran. The azeotropic mixture mentioned above is a mixture solution in which a composition of the liquid phase and a composition of the vapor phase are coincided with each other at a certain pressure to give a mixture having a constant boiling point. For example, a mixture consisting of 35 parts by weight of methanol and 65 parts by weight of 1,2-dichloroethane is an azeotropic solution. The presence of an azeotropic composition leads to uniform evaporation, thereby forming a uniform charge blocking layer without coating defects and improving storage stability of the charge blocking coating solution.

The binder resin contained in the blocking layer may be formed of the same materials as that of the blocking layer formed as a single resin layer. Among them, polyamide resin may be used because it satisfies various conditions required of the binder resin such as (i) polyamide resin is neither dissolved nor swollen in a solution used for forming the imaging layer on the blocking layer, and (ii) polyamide resin has an excellent adhesiveness with a conductive support as well as flexibility. In the polyamide resin, alcohol soluble nylon resin may be used, for example, copolymer nylon polymerized with 6-nylon, 6,6-nylon, 610-nylon, 11-nylon, 12-nylon and the like; and nylon which is chemically denatured such as N-alkoxy methyl denatured nylon and N-alkoxy ethyl denatured nylon. Another type of binder resin that may be used is a phenolic resin or polyvinyl butyral resin.

The charge blocking layer is formed by dispersing the binder resin, the grain shaped particles, and the needle shaped particles in the solvent to form a coating solution for the blocking layer; coating the conductive support with the coating solution and drying it. The solvent is selected for improving dispersion in the solvent and for preventing the coating solution from gelation with the elapse of time. Further, the azeotropic solvent may be used for preventing the composition of the coating solution from being changed as time passes, whereby storage stability of the coating solution may be improved and the coating solution may be reproduced.

The phrase "n-type" refers, for example, to materials which predominately transport electrons. Typical n-type materials include dibromoanthanthrone, benzimidazole perylene, zinc oxide, titanium oxide, azo compounds such as chlorodiane Blue and bisazo pigments, substituted 2,4-dibromotriazines, polynuclear aromatic quinones, zinc sulfide, and the like.

The phrase "p-type" refers, for example, to materials which transport holes. Typical p-type organic pigments include, for example, metal-free phthalocyanine, titanyl phthalocyanine, gallium phthalocyanine, hydroxy gallium phthalocyanine, chlorogallium phthalocyanine, copper phthalocyanine, and the like.

The Adhesive Layer

An intermediate layer 5 between the blocking layer and the charge generating layer may, if desired, be provided to promote adhesion. However, in embodiments, a dip coated aluminum drum may be utilized without an adhesive layer.

Additionally, adhesive layers may be provided, if necessary, between any of the layers in the photoreceptors to ensure adhesion of any adjacent layers. Alternatively, or in addition, adhesive material may be incorporated into one or both of the respective layers to be adhered. Such optional adhesive layers may have thicknesses of about 0.001 micrometer to about 0.2 micrometer. Such an adhesive layer may be applied, for example, by dissolving adhesive material in an appropriate solvent, applying by hand, spraying, dip coating, draw bar coating, gravure coating, silk screening, air knife coating, vacuum deposition, chemical treatment, roll coating, wire wound rod coating, and the like, and drying to remove the solvent. Suitable adhesives include, for example, film-forming polymers, such as polyester, dupont 49,000 (available from E. I. duPont de Nemours & Co.), Vitel PE-100 (available from Goodyear Tire and Rubber Co.), polyvinyl butyral, polyvinyl pyrrolidone, polyurethane, polymethyl methacrylate, and the like. The adhesive layer may be composed of a polyester with a $M_w$ of from about 50,000 to about 100,000, such as about 70,000, and a $M_n$ of about 35,000.

The Imaging Layer(s)

The imaging layer refers to a layer or layers containing charge generating material, charge transport material, or both the charge generating material and the charge transport material.

Either a n-type or a p-type charge generating material may be employed in the present photoreceptor.

In the case where the charge generating material and the charge transport material are in different layers—for example a charge generation layer and a charge transport layer—the charge transport layer may comprise a SOF, which may be a capped SOF. Further, in the case where the charge generating material and the charge transport material are in the same layer, this layer may comprise a SOF, which may be a capped SOF.

Charge Generation Layer

Illustrative organic photoconductive charge generating materials include azo pigments such as Sudan Red, Dian Blue, Janus Green B, and the like; quinone pigments such as Algol Yellow, Pyrene Quinone, Indanthrene Brilliant Violet RRP, and the like; quinocyanine pigments; perylene pigments such as benzimidazole perylene; indigo pigments such as indigo, thioindigo, and the like; bisbenzoimidazole pigments such as Indofast Orange, and the like; phthalocyanine pigments such as copper phthalocyanine, aluminochloro-phthalocyanine, hydroxygallium phthalocyanine, chlorogallium phthalocyanine, titanyl phthalocyanine and the like; quinacridone pigments; or azulene compounds. Suitable inorganic photoconductive charge generating materials include for example cadmium sulfide, cadmium sulfoselenide, cadmium selenide, crystalline and amorphous selenium, lead oxide and other chalcogenides. In embodiments, alloys of selenium may be used and include for instance selenium-arsenic, selenium-tellurium-arsenic, and selenium-tellurium.

Any suitable inactive resin binder material may be employed in the charge generating layer. Typical organic resinous binders include polycarbonates, acrylate polymers, methacrylate polymers, vinyl polymers, cellulose polymers, polyesters, polysiloxanes, polyamides, polyurethanes, epoxies, polyvinylacetals, and the like.

To create a dispersion useful as a coating composition, a solvent is used with the charge generating material. The solvent may be for example cyclohexanone, methyl ethyl ketone, tetrahydrofuran, alkyl acetate, and mixtures thereof. The alkyl acetate (such as butyl acetate and amyl acetate) can have from 3 to 5 carbon atoms in the alkyl group. The amount of solvent in the composition ranges for example from about 70% to about 98% by weight, based on the weight of the composition.

The amount of the charge generating material in the composition ranges for example from about 0.5% to about 30% by weight, based on the weight of the composition including a solvent. The amount of photoconductive particles (i.e, the charge generating material) dispersed in a dried photoconductive coating varies to some extent with the specific photoconductive pigment particles selected. For example, when phthalocyanine organic pigments such as titanyl phthalocyanine and metal-free phthalocyanine are utilized, satisfactory results are achieved when the dried photoconductive coating comprises between about 30 percent by weight and about 90 percent by weight of all phthalocyanine pigments based on the total weight of the dried photoconductive coating. Because the photoconductive characteristics are affected by the relative amount of pigment per square centimeter coated, a lower pigment loading may be utilized if the dried photoconductive coating layer is thicker. Conversely, higher pigment loadings are desirable where the dried photoconductive layer is to be thinner.

Generally, satisfactory results are achieved with an average photoconductive particle size of less than about 0.6 micrometer when the photoconductive coating is applied by dip coating. The average photoconductive particle size may be less than about 0.4 micrometer. In embodiments, the photoconductive particle size is also less than the thickness of the dried photoconductive coating in which it is dispersed.

In a charge generating layer, the weight ratio of the charge generating material ("CGM") to the binder ranges from 30 (CGM):70 (binder) to 70 (CGM):30 (binder).

For multilayered photoreceptors comprising a charge generating layer (also referred herein as a photoconductive layer) and a charge transport layer, satisfactory results may be achieved with a dried photoconductive layer coating thickness of between about 0.1 micrometer and about 10 micrometers. In embodiments, the photoconductive layer thickness is between about 0.2 micrometer and about 4 micrometers. However, these thicknesses also depend upon the pigment loading. Thus, higher pigment loadings permit the use of thinner photoconductive coatings. Thicknesses outside these ranges may be selected providing the objectives of the present invention are achieved.

Any suitable technique may be utilized to disperse the photoconductive particles in the binder and solvent of the coating composition. Typical dispersion techniques include, for example, ball milling, roll milling, milling in vertical attritors, sand milling, and the like. Typical milling times using a ball roll mill is between about 4 and about 6 days.

Charge transport materials include an organic polymer, a non-polymeric material, or a SOF, which may be a capped SOF, capable of supporting the injection of photoexcited holes or transporting electrons from the photoconductive material and allowing the transport of these holes or electrons through the organic layer to selectively dissipate a surface charge.

Organic Polymer Charge Transport Layer

Illustrative charge transport materials include for example a positive hole transporting material selected from compounds having in the main chain or the side chain a polycyclic aromatic ring such as anthracene, pyrene, phenanthrene, coronene, and the like, or a nitrogen-containing hetero ring such as indole, carbazole, oxazole, isoxazole, thiazole, imidazole, pyrazole, oxadiazole, pyrazoline, thiadiazole, triazole, and hydrazone compounds. Typical hole transport materials include electron donor materials, such as carbazole; N-ethyl carbazole; N-isopropyl carbazole; N-phenyl carbazole; tetraphenylpyrene; 1-methylpyrene; perylene; chrysene; anthracene; tetraphene; 2-phenyl naphthalene; azopyrene; 1-ethyl pyrene; acetyl pyrene; 2,3-benzochrysene; 2,4-benzopyrene; 1,4-bromopyrene; poly(N-vinylcarbazole); poly(vinylpyrene); poly(vinyltetraphene); poly(vinyltetracene) and poly(vinylperylene). Suitable electron transport materials include electron acceptors such as 2,4,7-trinitro-9-fluorenone; 2,4,5,7-tetranitro-fluorenone; dinitroanthracene; dinitroacridene; tetracyanopyrene; dinitroanthraquinone; and butylcarbonylfluorenemalononitrile, see U.S. Pat. No. 4,921,769 the disclosure of which is incorporated herein by reference in its entirety. Other hole transporting materials include arylamines described in U.S. Pat. No. 4,265,990 the disclosure of which is incorporated herein by reference in its entirety, such as N,N'-diphenyl-N,N'-bis(alkylphenyl)-(1,1'-biphenyl)-4,4'-diamine wherein alkyl is selected from the group consisting of methyl, ethyl, propyl, butyl, hexyl, and the like. Other known charge transport layer molecules may be selected, reference for example U.S. Pat. Nos. 4,921,773 and 4,464,450 the disclosures of which are incorporated herein by reference in their entireties.

Any suitable inactive resin binder may be employed in the charge transport layer. Typical inactive resin binders soluble in methylene chloride include polycarbonate resin, polyvinylcarbazole, polyester, polyarylate, polystyrene, polyacrylate, polyether, polysulfone, and the like. Molecular weights can vary from about 20,000 to about 1,500,000.

In a charge transport layer, the weight ratio of the charge transport material ("CTM") to the binder ranges from 30 (CTM):70 (binder) to 70 (CTM):30 (binder).

Any suitable technique may be utilized to apply the charge transport layer and the charge generating layer to the substrate. Typical coating techniques include dip coating, roll coating, spray coating, rotary atomizers, and the like. The coating techniques may use a wide concentration of solids. The solids content is between about 2 percent by weight and 30 percent by weight based on the total weight of the dispersion. The expression "solids" refers, for example, to the charge transport particles and binder components of the charge transport coating dispersion. These solids concentrations are useful in dip coating, roll, spray coating, and the like. Generally, a more concentrated coating dispersion may be used for roll coating. Drying of the deposited coating may be effected by any suitable conventional technique such as oven drying, infra-red radiation drying, air drying and the like. Generally, the thickness of the transport layer is between about 5 micrometers to about 100 micrometers, but thicknesses outside these ranges can also be used. In general, the ratio of the thickness of the charge transport layer to the charge generating layer is maintained, for example, from about 2:1 to 200:1 and in some instances as great as about 400:1.

Capped SOF Charge Transport Layer

Illustrative charge transport capped SOFs include for example a positive hole transporting material selected from compounds having a segment containing a polycyclic aromatic ring such as anthracene, pyrene, phenanthrene, coronene, and the like, or a nitrogen-containing hetero ring such as indole, carbazole, oxazole, isoxazole, thiazole, imidazole, pyrazole, oxadiazole, pyrazoline, thiadiazole, triazole, and hydrazone compounds. Typical hole transport SOF segments include electron donor materials, such as carbazole; N-ethyl carbazole; N-isopropyl carbazole; N-phenyl carbazole; tetraphenylpyrene; 1-methylpyrene; perylene; chrysene; anthracene; tetraphene; 2-phenyl naphthalene; azopyrene; 1-ethyl pyrene; acetyl pyrene; 2,3-benzochrysene; 2,4-benzopyrene; and 1,4-bromopyrene. Suitable electron transport SOF segments include electron acceptors such as 2,4,7-trinitro-9-fluorenone; 2,4,5,7-tetranitro-fluorenone; dinitroanthracene; dinitroacridene; tetracyanopyrene; dinitroanthraquinone; and butylcarbonylfluorenemalononitrile, see U.S. Pat. No. 4,921,769. Other hole transporting SOF segments include arylamines described in U.S. Pat. No. 4,265,990, such as N,N'-diphenyl-N,N'-bis(alkylphenyl)-(1,1'-biphenyl)-4,4'-diamine wherein alkyl is selected from the group consisting of methyl, ethyl, propyl, butyl, hexyl, and the like. Other known charge transport SOF segments may be selected, reference for example U.S. Pat. Nos. 4,921,773 and 4,464,450.

The capped SOF charge transport layer may be prepared by
(a) preparing a liquid-containing reaction mixture comprising a plurality of molecular building blocks with inclined charge transport properties each comprising a segment and a number of functional groups;
(b) depositing the reaction mixture as a wet film; and
(c) promoting a change of the wet film including the molecular building blocks to a dry film comprising the SOF comprising a plurality of the segments and a plurality of linkers arranged as a covalent organic framework, wherein at a macroscopic level the covalent organic framework is a film.

Addition of the capping unit may occur during any of the steps a, b, and c, as described above. The deposition of the reaction mixture as a wet layer may be achieved by any suitable conventional technique and applied by any of a number of application methods. Typical application methods include, for example, hand coating, spray coating, web coating, dip coating and the like. The capped SOF forming reaction mixture may use a wide range of molecular building block loadings. In embodiments, the loading is between about 2 percent by weight and 50 percent by weight based on the total weight of the reaction mixture. The term "loading" refers, for example, to the molecular building block components of the charge transport capped SOF reaction mixture. These loadings are useful in dip coating, roll, spray coating, and the like. Generally, a more concentrated coating dispersion may be used for roll coating. Drying of the deposited coating may be affected by any suitable conventional technique such as oven drying, infra-red radiation drying, air drying and the like. Generally, the thickness of the charge transport SOF layer is between about 5 micrometers to about 100 micrometers, such as about 10 micrometers to about 70 micrometers or 10 micrometers to about 40 micrometers. In general, the ratio of the thickness of the charge transport layer to the charge generating layer may be maintained from about 2:1 to 200:1 and in some instances as great as 400:1.

Single Layer P/R—Organic Polymer

The materials and procedures described herein may be used to fabricate a single imaging layer type photoreceptor containing a binder, a charge generating material, and a charge transport material. For example, the solids content in the dispersion for the single imaging layer may range from about 2% to about 30% by weight, based on the weight of the dispersion.

Where the imaging layer is a single layer combining the functions of the charge generating layer and the charge transport layer, illustrative amounts of the components contained therein are as follows: charge generating material (about 5% to about 40% by weight), charge transport material (about 20% to about 60% by weight), and binder (the balance of the imaging layer).

Single Layer P/R—Capped SOF

The materials and procedures described herein may be used to fabricate a single imaging layer type photoreceptor containing a charge generating material and a charge transport capped SOF. For example, the solids content in the dispersion for the single imaging layer may range from about 2% to about 30% by weight, based on the weight of the dispersion.

Where the imaging layer is a single layer combining the functions of the charge generating layer and the charge transport layer, illustrative amounts of the components contained therein are as follows: charge generating material (about 2% to about 40% by weight), with an inclined added functionality of charge transport molecular building block (about 20% to about 75% by weight).

The Overcoating Layer

Embodiments in accordance with the present disclosure can, optionally, further include an overcoating layer or layers 8, which, if employed, are positioned over the charge generation layer or over the charge transport layer. This layer comprises capped SOFs that are electrically insulating or slightly semi-conductive.

Such a protective overcoating layer includes a capped SOF forming reaction mixture containing a capping unit and a plurality of molecular building blocks that optionally contain charge transport segments.

Additives may be present in the overcoating layer in the range of about 0.5 to about 40 weight percent of the overcoating layer. In embodiments, additives include organic and inorganic particles which can further improve the wear resistance and/or provide charge relaxation property. In embodiments, organic particles include Teflon powder, carbon black, and graphite particles. In embodiments, inorganic particles include insulating and semiconducting metal oxide particles such as silica, zinc oxide, tin oxide and the like. Another semiconducting additive is the oxidized oligomer salts as described in U.S. Pat. No. 5,853,906 the disclosure of which is incorporated herein by reference in its entirety. In embodiments, oligomer salts are oxidized N,N,N',N'-tetra-p-tolyl-4,4'-biphenyldiamine salt.

The capped SOF overcoating layer may be prepared by
(a) preparing a liquid-containing reaction mixture comprising a plurality of molecular building blocks with an inclined charge transport properties each comprising a segment and a number of functional groups;
(b) depositing the reaction mixture as a wet film; and
(c) promoting a change of the wet film including the molecular building blocks to a dry film comprising the SOF comprising a plurality of the segments and a plurality of linkers arranged as a covalent organic framework, wherein at a macroscopic level the covalent organic framework is a film.

Addition of the capping unit may occur during any of the steps a, b, and c, as described above. The deposition of the reaction mixture as a wet layer may be achieved by any suitable conventional technique and applied by any of a number of application methods. Typical application methods include, for example, hand coating, spray coating, web coating, dip coating and the like. Promoting the change of the wet film to the dry SOF may be affected by any suitable conventional techniques, such as oven drying, infrared radiation drying, air drying, and the like.

Overcoating layers from about 2 micrometers to about 15 micrometers, such as from about 3 micrometers to about 8 micrometers are effective in preventing charge transport molecule leaching, crystallization, and charge transport layer cracking in addition to providing scratch and wear resistance.

The Ground Strip

The ground strip 9 may comprise a film-forming binder and electrically conductive particles. Cellulose may be used to disperse the conductive particles. Any suitable electrically conductive particles may be used in the electrically conductive ground strip layer 8. The ground strip 8 may, for example, comprise materials that include those enumerated in U.S. Pat. No. 4,664,995 the disclosure of which is incorporated herein by reference in its entirety. Typical electrically conductive particles include, for example, carbon black, graphite, copper, silver, gold, nickel, tantalum, chromium, zirconium, vanadium, niobium, indium tin oxide, and the like.

The electrically conductive particles may have any suitable shape. Typical shapes include irregular, granular, spherical, elliptical, cubic, flake, filament, and the like. In embodiments, the electrically conductive particles should have a particle size less than the thickness of the electrically conductive ground strip layer to avoid an electrically conductive ground strip layer having an excessively irregular outer surface. An average particle size of less than about 10 micrometers generally avoids excessive protrusion of the electrically conductive particles at the outer surface of the dried ground strip layer and ensures relatively uniform dispersion of the particles through the matrix of the dried ground strip layer. Concentration of the conductive particles to be used in the ground strip depends on factors such as the conductivity of the specific conductive materials utilized.

In embodiments, the ground strip layer may have a thickness of from about 7 micrometers to about 42 micrometers, such as from about 14 micrometers to about 27 micrometers.

In embodiments, an imaging member may comprise a capped SOF as the surface layer (OCL or CTL). This imaging member may be a capped SOF that comprises N,N,N',N'-tetra-(methylenephenylene)biphenyl-4,4'-diamine and segments N,N,N',N'-tetraphenyl-terphenyl-4,4'-diamine segments. Such an capped SOF may be prepared from N,N,N',N'-tetrakis-[(4-hydroxymethyl)phenyl]-biphenyl-4,4'-diamine and N,N'-diphenyl-N,N'-bis-(3-hydroxyphenyl)-terphenyl-4,4'-diamine molecular building blocks. The SOF imaging member may also comprise N,N,N',N'-tetra-(methylenephenylene)biphenyl-4,4'-diamine and segments N,N,N',N'-tetraphenyl-biphenyl-4,4'-diamine segments. In embodiments, the SOF of the imagining member may be prepared from N,N,N',N'-tetrakis-[(4-hydroxymethyl)phenyl]-biphenyl-4,4'-diamine and N,N'-diphenyl-N,N'-bis-(3-hydroxyphenyl)-biphenyl-4,4'-diamine molecular building blocks.

In embodiments, imaging member may comprise a SOF, which may be a capped SOF, layer, where the thickness of the SOF layer is between 1 and 15 microns. The SOF, which may be a capped SOF, in such an imaging member may be a single layer or two or more layers.

Application B: Capped SOFs in Thin Film Transistors

Figure 5:
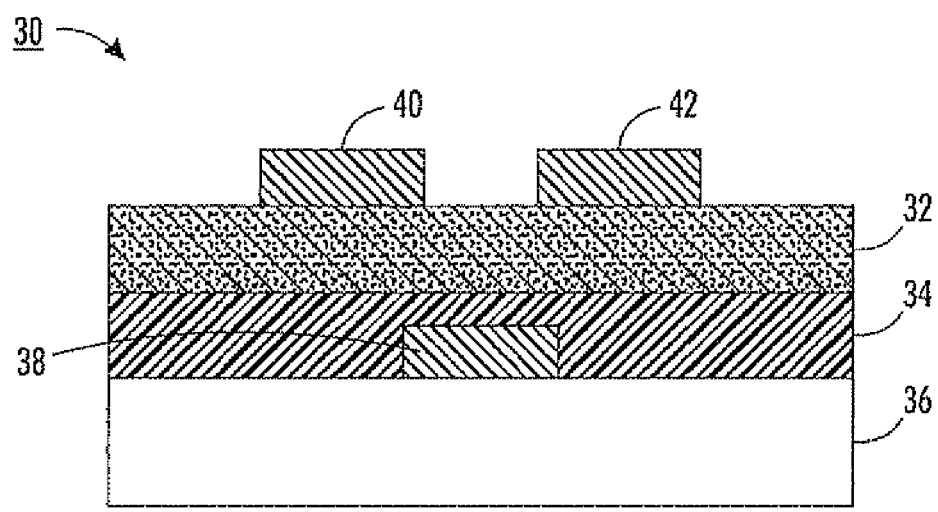
FIG. 5 represents a simplified side view of a first exemplary thin film transistor that incorporates a SOF of the present disclosure.

FIG. 5 schematically illustrates a thin film transistor (TFT) configuration 30 comprised of a substrate 36, a gate electrode 38, a source electrode 40 and a drain electrode 42, an insulating layer 34, and an organic semiconductor layer 32.

The substrate may be composed of for instance silicon wafer, glass plate, metal sheet, plastic film or sheet. For structurally flexible devices, plastic substrate, such as for example polyester, polycarbonate, polyimide sheets and the like may be used. The thickness of the substrate may be from amount 10 micrometers to over 10 millimeters with an exemplary thickness being from about 50 micrometers to about 2 millimeters, especially for a flexible plastic substrate and from about 0.4 to about 10 millimeters for a rigid substrate such as glass or silicon.

The compositions of the gate electrode, the source electrode, and the drain electrode are now discussed. The gate electrode may be a thin metal film, a conducting polymer film, a conducting film made from conducting ink or paste or the substrate itself, for example heavily doped silicon. Examples of gate electrode materials include, for example, aluminum, silver, gold, chromium, indium tin oxide, conducting polymers such as polystyrene sulfonate-doped poly(3,4-ethylenedioxythiophene) (PSS-PEDOT), conducting ink/paste comprised of carbon black/graphite or colloidal silver dispersion in polymer binders, such as ELECTRODAG™ available from Acheson Colloids Company. The gate electrode layer may be prepared by vacuum evaporation, sputtering of metals or conductive metal oxides, coating from conducting polymer solutions or conducting inks by spin coating, casting or printing. The thickness of the gate electrode layer ranges, for example, from about 10 to about 200 nanometers for metal films and in the range of about 1 to about 10 micrometers for polymer conductors. The source and drain electrode layers may be fabricated from materials which provide a low resistance ohmic contact to the semiconductor layer. Typical materials suitable for use as source and drain electrodes include those of the gate electrode materials such as silver, gold, nickel, aluminum, platinum, conducting polymers and conducting inks. Typical thicknesses of source and drain electrodes are about, for example, from about 40 nanometers to about 1 micrometer, such as about 100 to about 400 nanometers.

The insulating layer generally may be an inorganic material film or an organic polymer film. Inorganic materials suitable as the insulating layer include, for example, silicon oxide, silicon nitride, aluminum oxide, barium titanate, barium zirconium titanate and the like; examples of organic polymers for the insulating layer include polyesters, polycarbonates, poly(vinyl phenol), polyimides, polystyrene, poly(methacrylate)s, poly(acrylate)s, epoxy resin, liquid glass, and the like. The thickness of the insulating layer is, for example from about 10 nanometers to about 500 nanometers depending on the dielectric constant of the dielectric material used. An exemplary thickness of the insulating layer is from about 100 nanometers to about 500 nanometers, such as from about 200 nanometers to about 400 nanometers. The insulating layer may have a conductivity that is for example less than about $10^{-12}$ S/cm.

Situated, for example, between and in contact with the insulating layer and the source/drain electrodes is the semiconductor layer wherein the thickness of the semiconductor layer is generally, for example, about 10 nanometers to about 1 micrometer, or about 40 to about 100 nanometers. The semiconductor layer may comprise a capped SOF, such as an capped SOF with semiconductor added functionality. An exemplary process for preparing the capped SOF with semiconductor added functionality may be performed as follows (addition of the capping unit may occur during any of the steps a, b, and c, as described above):

(a) preparing a liquid-containing reaction mixture comprising a plurality of molecular building blocks each comprising a segment with inclined semiconductor properties and a number of functional groups;

(b) depositing the reaction mixture as a wet film; and (c) promoting a change of the wet film including the molecular building blocks to a dry film comprising the SOF comprising a plurality of the segments and a plurality of linkers arranged as a covalent organic framework, wherein at a macroscopic level the covalent organic framework is a film which is multi-segment thick.

The insulating layer, the gate electrode, the semiconductor layer, the source electrode, and the drain electrode are formed in any sequence, particularly where in embodiments the gate electrode and the semiconductor layer both contact the insulating layer, and the source electrode and the drain electrode both contact the semiconductor layer. The phrase "in any sequence" includes sequential and simultaneous formation. For example, the source electrode and the drain electrode may be formed simultaneously or sequentially. The composition, fabrication, and operation of thin film transistors are described in Bao et al., U.S. Pat. No. 6,107,117, the disclosure of which is totally incorporated herein by reference.

Application C: Capped SOFs in Radio Frequency Identification

Recently, radio frequency identification (RFID) technology has gained tremendous popularity as a device for storing and transmitting information. RFID technology utilizes a tag transponder, which is placed on an object, and a reader, also referred to herein as an interrogator, to read and identify the tag. RFID technologies are broadly categorized as using either "active" tags or "passive" tags. Active tags have a local power source (such as a battery) so that the active tag sends a signal to be read by the interrogator. Active tags have a longer signal range. "Passive" tags, in contrast, have no internal power source. Instead, passive tags derive power from the reader, and the passive tag re-transmits or transponds information upon receiving the signal from the reader. Passive tags have a much shorter signal range (typically less than 20 feet).

Generally, both categories of tags have an electronic circuit that is typically in the form of an integrated circuit or silicon chip. The circuit stores and communicates identification data to the reader. In addition to the chip, the tag includes some form of antenna that is electrically connected to the chip. Active tags incorporate an antenna which communicates with the reader from the tag's own power source. For passive tags, the antenna acts as a transducer to convert radio frequency (RF) energy originating from the reader to electrical power. The chip then becomes energized and performs the communication function with the reader. On the other hand, a chipless RFID tag has neither an integrated circuit nor discrete electronic components, such as the transistor. This feature allows chipless RFID tags to be printed directly onto a substrate at lower costs than traditional RFID tags.

As a practical matter, RFID technology uses radio frequencies that have much better penetration characteristics to material than do optical signals, and will work under more hostile environmental conditions than bar code labels. Therefore, the RFID tags may be read through paint, water, dirt, dust, human bodies, concrete, or through the tagged item itself RFID tags may be used in managing inventory, automatic identification of cars on toll roads, security systems, electronic access cards, keyless entry and the like. The RFID antenna may be printed directly on the substrate using a conductive metal ink. Alternatively, metal fibers may be incorporated directly into the substrate. For example, one chipless RFID technology from Inkode Corp uses embedded aluminum fibers that are embedded into paper. The aluminum fibers must be cut to the appropriate wavelength (¼ wavelength) and be incorporated into the paper fibers as a furnish additive during the papermaking process. Any component of the RFID tag may comprise a capped SOF, for example, the substrate and/or the antenna of the RFID tag may comprise a capped SOF.

Any component of a conventional organic light emitting diode (OLED) structure including a substrate, an anode, a hole injecting layer, a hole transmission layer, an electron transmission layer, and a cathode layer may comprise a SOF, which may be a capped SOF. For example, a typical organic light emitting device may include one or more SOFs, one or more of which may be a capped SOF, as a constituent of one or more or the following components: transparent first electrode, which usually acts as a hole-injecting anode and a luminescent region, comprising one or more electroluminescent SOF layer(s), which usually acts as an electron-injecting cathode.

A number of examples of the process used to make SOFs and capped SOFs are set forth herein and are illustrative of the different compositions, conditions, techniques that may be utilized. Identified within each example are the nominal actions associated with this activity. The sequence and number of actions along with operational parameters, such as temperature, time, coating method, and the like, are not limited by the following examples. All proportions are by weight unless otherwise indicated. The term "rt" refers, for example, to temperatures ranging from about 20° C. to about 25° C. Mechanical measurements were measured on a TA Instruments DMA Q800 dynamic mechanical analyzer using methods standard in the art. Differential scanning calorimetry was measured on a TA Instruments DSC 2910 differential scanning calorimeter using methods standard in the art. Thermal gravimetric analysis was measured on a TA Instruments TGA 2950 thermal gravimetric analyzer using methods standard in the art. FT-IR spectra was measured on a Nicolet Magna 550 spectrometer using methods standard in the art. Thickness measurements <1 micron were measured on a Dektak 6m Surface Profiler. Surface energies were measured on a Fibro DAT 1100 (Sweden) contact angle instrument using methods standard in the art. Unless otherwise noted, the SOFs produced in the following examples were either pinhole-free SOFs or substantially pinhole-free SOFs.

The SOFs coated onto Mylar were delaminated by immersion in a room temperature water bath. After soaking for 10 minutes the SOF generally detached from Mylar substrate. This process is most efficient with a SOF coated onto substrates known to have high surface energy (polar), such as glass, mica, salt, and the like.

Given the examples below it will be apparent, that the compositions prepared by the methods of the present disclosure may be practiced with many types of components and may have many different uses in accordance with the disclosure above and as pointed out hereinafter.

The SOF capping units may also be added to an SOF wherein the microscopic arrangement of segments is patterned. The term "patterning" refers, for example, to the sequence in which segments are linked together.

A patterned film may be detected using spectroscopic techniques that are capable of assessing the successful formation of linking groups in a SOF. Such spectroscopies include, for example, Fourier-transfer infrared spectroscopy, Raman spectroscopy, and solid-state nuclear magnetic resonance spectroscopy. Upon acquiring a data by a spectroscopic technique from a sample, the absence of signals from functional groups on building blocks and the emergence of signals from linking groups indicate the reaction between building blocks and the concomitant patterning and formation of an SOF.

Different degrees of patterning are also embodied. Full patterning of a SOF will be detected by the complete absence of spectroscopic signals from building block functional groups. Also embodied are SOFs having lowered degrees of patterning wherein domains of patterning exist within the SOF. SOFs with domains of patterning, when measured spectroscopically, will produce signals from building block functional groups which remain unmodified at the periphery of a patterned domain.

It is appreciated that a very low degree of patterning is associated with inefficient reaction between building blocks and the inability to form a film. Therefore, successful implementation of the process of the present disclosure requires appreciable patterning between building blocks within the SOF. The degree of necessary patterning to form a SOF is variable and can depend on the chosen capping units, building blocks and desired linking groups. The minimum degree of patterning required is that required to form a film using the process described herein, and may be quantified as formation of about 20% or more of the intended linking groups, such as about 40% or more of the intended linking groups or about 50% or more of the intended linking groups. Formation of linking groups and capping units may be detected spectroscopically as described earlier in the embodiments.

Mechanical Properties

Figure 9:
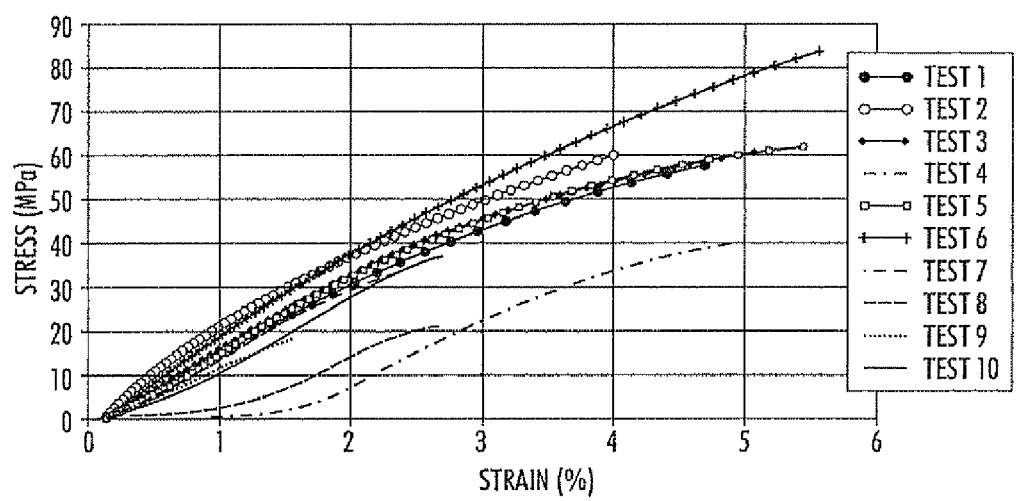
FIG. 9 is a graphic representation of various stress-strain curves for capped SOFs versus a non-capped. SOF.

In embodiments some capped SOFs are found to have different toughness (FIG. 9). By introduction of capping units, and varying capping group loading in a SOF, the toughness of the SOF can be enhanced or the toughness of the SOF can be attenuated.

In embodiments, toughness may be assessed by measuring the stress-strain curve for SOFs. This test is conducted by mounting a dog-bone shaped piece of SOF of known dimensions between two clamps; one stationary, and one moving. The moving clamp applies a force at a known rate (N/min) causing a stress (Force/area) on the film. This stress causes the film to elongate and a graph comparing stress vs. strain is created. The Young's Modulus (slope of the linear section) as well as rupture point (stress and strain at breakage) and toughness (integral of the curve) can be determined. These data provide insight into the mechanical properties of the film. For the purposes of embodiments the differences in mechanical properties (toughness) between SOFs are denoted by their respective rupture points.

FIG. 9 shows the stress-strain curves for some capped SOFs in embodiments. The ends of the curves are the rupture points of the capped SOFs. Different rupture points are evident for capped SOFs versus uncapped SOFs, and different ruptures points are also evident between capping unit loadings and capping unit types.

In embodiments, the rupture points of capped SOF films (with respect to the corresponding non-capped SOF compositions) may be attenuated by about 1% to about 85%, such as from about 5% to about 25%.

In embodiments, the rupture points of capped SOF films (with respect to the corresponding non-capped SOF compositions) may be enhanced by about 1% to about 400%, about 20% to about 200%, or from about 50% to about 100%.

The following experiments demonstrate the development of a SOF without the presence of a capping unit. These experiments are followed by experiments that demonstrate the development of capped SOFs.

EXAMPLES

EXAMPLE 1 describes the synthesis of a Type 2 SOF wherein components are combined such that etherification linking chemistry is promoted between two building blocks. The presence of an acid catalyst and a heating action yield a SOF with the method described in EXAMPLE 1.

Example 1

Type 2 SOF (Action A) Preparation of the liquid containing reaction mixture. The following were combined: the building block benzene-1,4-dimethanol [segment=p-xylyl; Fg=hydroxyl (—OH); (0.47 g, 3.4 mmol)] and a second building block N4,N4,N4',N4'-tetrakis(4-(methoxymethyl)phenyl)biphenyl-4,4'-diamine [segment=N4,N4,N4',N4'-tetra-p-tolylbiphenyl-4,4'-diamine; Fg=methoxy ether (—OCH$_3$); (1.12 g, 1.7 mmol)], and 17.9 g of 1-methoxy-2-propanol. The mixture was shaken and heated to 60° C. until a homogenous solution resulted. Upon cooling to room temperature, the solution was filtered through a 0.45 micron PTFE membrane. To the filtered solution was added an acid catalyst delivered as 0.31 g of a 10 wt % solution of p-toluenesulfonic acid in 1-methoxy-2-propanol to yield the liquid containing reaction mixture.

(Action B) Deposition of reaction mixture as a wet film. The reaction mixture was applied to the reflective side of a metalized (TiZr) MYLAR™ substrate using a constant velocity draw down coater outfitted with a bird bar having an 8 mil gap.

Figure 6:
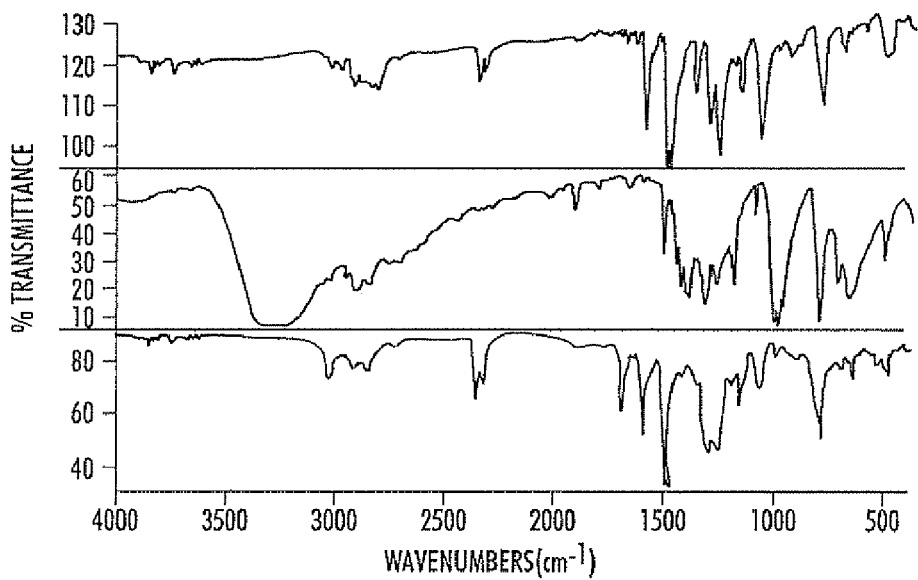
FIG. 6 is a graphic representation that compares the Fourier transform infrared spectral of the products of control experiments mixtures, wherein only N4,N4,N4',N4'-tetrakis(4-(methoxymethyl)phenyl)biphenyl-4,4'-diamine is added to the liquid reaction mixture (top), wherein only benzene-1,4-dimethanol is added to the liquid reaction mixture (middle), and wherein the necessary components needed to form a patterned Type 2 SOF are included into the liquid reaction mixture (bottom).

(Action C) Promotion of the change of the wet film to a dry SOF. The metalized MYLAR™ substrate supporting the wet layer was rapidly transferred to an actively vented oven preheated to 130° C. and left to heat for 40 min. These actions provided a SOF having a thickness ranging from about 3-6 microns, which may be delaminated from the substrate as a single free-standing SOF. The color of the SOF was green. The Fourier-transform infrared spectrum of a portion of this SOF is provided in FIG. 6.

To demonstrate that the SOF prepared in EXAMPLE 1 comprises segments from the employed molecular building blocks that are patterned within the SOF, three control experiments were conducted. Namely, three liquid reaction mixtures were prepared using the same procedure as set forth in Action A in EXAMPLE 1; however, each of these three formulations were modified as follows:

(Control reaction mixture 1; Example 2) the building block benzene-1,4-dimethanol was not included.
(Control reaction mixture 2; Example 3) the building block N4,N4,N4',N4'-tetrakis(4-(methoxymethyl)phenyl)biphenyl-4,4'-diamine was not included.
(Control reaction mixture 3; Example 4) the catalyst p-toluenesulfonic acid was not included The full descriptions of the SOF forming process for the above described control experiments are detailed in EXAMPLES 2-4 below.

Example 2

Control Experiment Wherein the Building Block Benzene-1,4-Dimethanol was not Included (Action A) Preparation of the liquid containing reaction mixture. The following were combined: the building block N4,N4,N4',N4'-tetrakis(4-(methoxymethyl)phenyl)biphenyl-4,4'-diamine [segment=N4,N4,N4',N4'-tetra-p-tolylbiphenyl-4,4'-diamine; Fg=methoxy ether (—OCH$_3$); (1.12 g, 1.7 mmol)], and 17.9 g of 1-methoxy-2-propanol. The mixture was shaken and heated to 60° C. until a homogenous solution resulted. Upon cooling to room temperature, the solution was filtered through a 0.45 micron PTFE membrane. To the filtered solution was added an acid catalyst delivered as 0.31 g of a 10 wt % solution of p-toluenesulfonic acid in 1-methoxy-2-propanol to yield the liquid containing reaction mixture.

(Action B) Deposition of reaction mixture as a wet film. The reaction mixture was applied to the reflective side of a metalized (TiZr) MYLAR™ substrate using a constant velocity draw down coater outfitted with a bird bar having an 8 mil gap.

(Action C) Attempted promotion of the change of the wet film to a dry SOF. The metalized MYLAR™ substrate supporting the wet layer was rapidly transferred to an actively vented oven preheated to 130° C. and left to heat for 40 min. These actions did not provide a film. Instead, a precipitated powder of the building block was deposited onto the substrate.

Example 3

Control Experiment wherein the Building Block N4,N4,N4',N4'-tetrakis(4-(methoxymethyl)phenyl) biphenyl-4,4'-diamine was not Included (Action A) Preparation of the liquid containing reaction mixture. The following were combined: the building block benzene-1,4-dimethanol [segment=p-xylyl; Fg=hydroxyl (—OH); (0.47 g, 3.4 mmol)] and 17.9 g of 1-methoxy-2-propanol. The mixture was shaken and heated to 60° C. until a homogenous solution resulted. Upon cooling to room temperature, the solution was filtered through a 0.45 micron PTFE membrane. To the filtered solution was added an acid catalyst delivered as 0.31 g of a 10 wt % solution of p-toluenesulfonic acid in 1-methoxy-2-propanol to yield the liquid containing reaction mixture.

(Action B) Deposition of reaction mixture as a wet film. The reaction mixture was applied to the reflective side of a metalized (TiZr) MYLAR™ substrate using a constant velocity draw down coater outfitted with a bird bar having an 8 mil gap.

(Action C) Attempted promotion of the change of the wet film to a dry SOF. The metalized MYLAR™ substrate supporting the wet layer was rapidly transferred to an actively vented oven preheated to 130° C. and left to heat for 40 min. These actions did not provide a film. Instead, a precipitated powder of the building block was deposited onto the substrate.

Example 4

Control Experiment Wherein the Acid Catalyst p-toluenesulfonic Acid was not Included (Action A) Preparation of the liquid containing reaction mixture. The following were combined: the building block benzene-1,4-dimethanol [segment p-xylyl; Fg=hydroxyl (—OH); (0.47 g, 3.4 mmol)] and a second building block N4,N4,N4',N4'-tetrakis(4-(methoxymethyl)phenyl)biphenyl-4,4'-diamine [segment=N4,N4,N4',N4'-tetra-p-tolylbiphenyl-4,4'-diamine; Fg=methoxy ether (—OCH$_3$); (1.12 g, 1.7 mmol)], and 17.9 g of 1-methoxy-2-propanol. The mixture was shaken and heated to 60° C. until a homogenous solution resulted. Upon cooling to room temperature, the solution was filtered through a 0.45 micron PTFE membrane to yield the liquid containing reaction mixture.

(Action B) Deposition of reaction mixture as a wet film. The reaction mixture was applied to the reflective side of a metalized (TiZr) MYLAR™ substrate using a constant velocity draw down coater outfitted with a bird bar having an 8 mil gap.

(Action C) Attempted promotion of the change of the wet film to a dry SOF. The metalized MYLAR™ substrate supporting the wet layer was rapidly transferred to an actively vented oven preheated to 130° C. and left to heat for 40 min. These actions did not provide a film. Instead, a precipitated powder of the building blocks was deposited onto the substrate.

As described in EXAMPLES 2-4, each of the three control reaction mixtures were subjected to Action B and Action C as outlined in EXAMPLE 1. However, in all cases a SOF did not form; the building blocks simply precipitated on the substrate. It is concluded from these results that building blocks cannot react with themselves under the stated processing conditions nor can the building blocks react in the absence of a promoter (p-toluenesulfonic acid). Therefore, the activity described in EXAMPLE 1 is one wherein building blocks (benzene-1,4-dimethanol and N4,N4,N4',N4'-tetrakis(4-(methoxymethyl)phenyl)biphenyl-4,4'-diamine) can only react with each other when promoted to do so. A patterned SOF results when the segments p-xylyl and N4,N4,N4',N4'-tetra-p-tolylbiphenyl-4,4'-diamine connect only with each other. The Fourier-transform infrared spectrum, compared to that of the products of the control experiments, demonstrates the absence of functional groups (notably the absence of the hydroxyl band from the benzene-1,4-dimethanol) from the starting materials and further supports that the connectivity between segments has proceed as described above. Also, the complete absence of the hydroxyl band in the spectrum for the SOF indicates that the patterning is to a very high degree.

Described below are further Examples of pinhole-free SOFs and/or substantially pinhole-free SOFs prepared in accordance with the present disclosure.

Example 5

Figure 7:
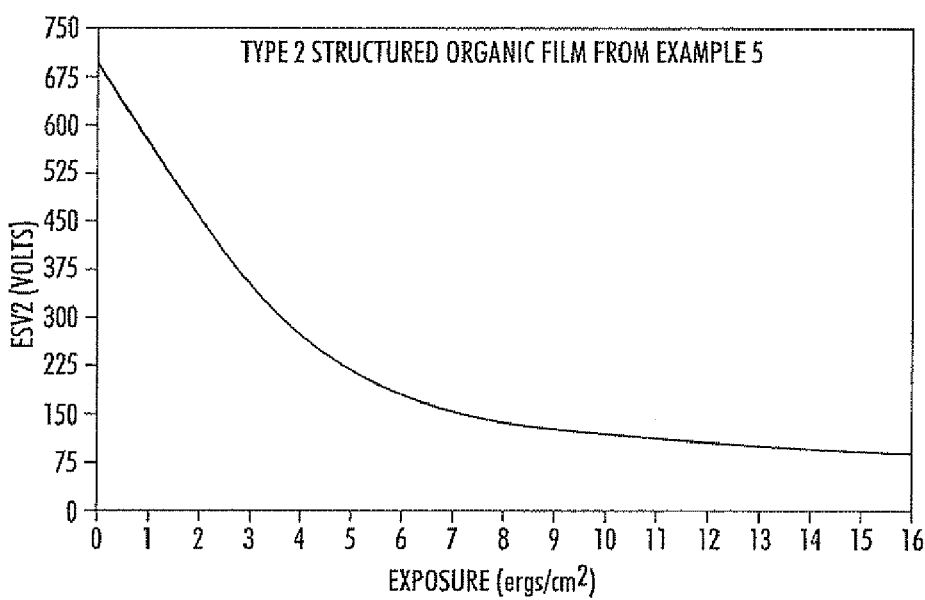
FIG. 7 is a graphic representation of a photo-induced discharge curve (PIDC) illustrating the photoconductivity of a Type 2 structured organic film overcoat layer.

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4''-diamine; Fg=hydroxy (—OH); 3.36 g] and the building block N,N'-diphenyl-N,N'-bis-(3-hydroxyphenyl)-biphenyl-4,4'-diamine [segment=N,N,N',N'-tetraphenyl-biphenyl-4,4'-diamine; Fg=hydroxyl (—OH); 5.56 g]; the additives Cymel303 (480 mg) and Silclean 3700 (383 mg), and the catalyst Nacure XP-357 (480 mg) and 1-methoxy-2-propanol (33.24 g). The mixture was mixed on a rolling wave rotator for 10 min and then heated at 55° C. for 65 min until a homogenous solution resulted. The mixture was placed on the rotator and cooled to room temperature. The solution was filtered through a 1 micron PTFE membrane. (Action B) The reaction mixture was applied to a commercially available, 30 mm drum photoreceptor using a cup coater (Tsukiage coating) at a pull-rate of 485 mm/min. (Action C) The photoreceptor drum supporting the wet layer was rapidly transferred to an actively vented oven preheated to 140° C. and left to heat for 40 min. These actions provided a film having a thickness ranging from 6.0 to 6.2 microns. FIG. 7 is a photo-induced discharge curve (PIDC) illustrating the photoconductivity of this SOF overcoat layer (voltage at 75 ms (expose-to-measure)).

Example 6

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4''-diamine; Fg=hydroxy (—OH); 4.24 g] and the building block N,N'-diphenyl-N,N'-bis-(3-hydroxyphenyl)-terphenyl-4,4'-diamine [segment=N,N,N',N'-tetraphenyl-terphenyl-4,4'-diamine; Fg=hydroxyl (—OH); 5.62 g]; the additives Cymel303 (530 mg) and Silclean 3700 (420 mg), and the catalyst Nacure XP-357 (530 mg) and 1-methoxy-2-propanol (41.62 g). The mixture was mixed on a rolling wave rotator for 10 min and then heated at 55° C. for 65 min until a homogenous solution resulted. The mixture was placed on the rotator and cooled to room temperature. The solution was filtered through a 1 micron PTFE membrane. (Action B) The reaction mixture was applied to a commercially available, 30 mm drum photoreceptor using a cup coater (Tsukiage coating) at a pull-rate of 485 mm/min. (Action C) The photoreceptor dram supporting the wet layer was rapidly transferred to an actively vented oven preheated to 155° C. and left to heat for 40 min. These actions provided a SOF having a thickness of 6.2 microns. As seen in the Table 1 below, the specific SOF overcoat layer composition of N,N'-diphenyl-N,N'-bis-(3-hydroxyphenyl)-terphenyl-4,4'-diamine (or N,N'-diphenyl-N,N-bis-(3-hydroxyphenyl)-biphenyl-4,4'-diamine) and N,N,N',N'-tetrakis-[(4-hydroxymethyl)phenyl]-biphenyl-4,4'-diamine provide improved properties for photoreceptors with biased charge roll (BCR)-charging. Additionally, The use of N,N'-diphenyl-N,N'-bis-(3-hydroxyphenyl)-terphenyl-4,4'-diamine (or N,N'-diphenyl-N,N'-bis-(3-hydroxyphenyl)-terphenyl-4,4'-diamine) and N,N,N',N'-tetrakis-[(4-hydroxymethyl)phenyl]-biphenyl-4,4'-diamine allows for SOF overcoat layers to be prepared with hole transport molecule loadings greater than 90% leading to excellent electrical performance (low Vr) for overcoat layers with thicknesses greater than six microns. Experiments have shown that changing the ratio of the two molecular building blocks may modulate the wear rate.

TABLE 1

SOF overcoat layer compositions.

| | Properties | Cross-linked polymer | SOF | SOF | SOF | SOF |
|---|---|---|---|---|---|---|
| Chemicals | cross-linker | Cymel 303 | N/A | N/A | N/A | N/A |
| | HTM (1) | N,N'-diphenyl-N,N'-bis-(3-hydroxyphenyl)-biphenyl-4,4'-diamine | N,N'-diphenyl-N,N'-bis-(3-hydroxyphenyl)-biphenyl-4,4'-diamine (58%) | N,N'-diphenyl-N,N'-bis-(3-hydroxyphenyl)-biphenyl-4,4'-diamine (63%) | N,N'-diphenyl-N,N'-bis-(3-hydroxyphenyl)-biphenyl-4,4'-diamine (58%) | N,N'-diphenyl-N,N'-bis-(3-hydroxyphenyl)-biphenyl-4,4'-diamine (53%) |
| | HTM (2) | N/A | N,N,N',N'-tetrakis-[(4-hydroxymethyl)phenyl]- | N,N,N',N'-tetrakis-[(4-hydroxymethyl)phenyl]- | N,N,N',N'-tetrakis-[(4-hydroxymethyl)phenyl]- | N,N,N',N'-tetrakis-[(4-hydroxymethyl)phenyl]- |

TABLE 1-continued

SOF overcoat layer compositions.

| | Properties | Cross-linked polymer | SOF | SOF | SOF | SOF |
|---|---|---|---|---|---|---|
| | | | biphenyl-4,4'-diamine (35%) | biphenyl-4,4'-diamine (30%) | biphenyl-4,4'-diamine (35%) | biphenyl-4,4'-diamine (40%) |
| | HTM wt % | 54% | 93% | 93% | 93% | 93% |
| | Acid Catalyst | Nacure XP-357 | Nacure XP-357 (1%) | Nacure XP-357 (1%) | Nacure XP-357 (1%) | Nacure XP-357 (1%) |
| | Additives | Silclean 3700 | Silclean 3700 (1%) | Silclean 3700 (1%) | Silclean 3700 (1%) | Silclean 3700 (1%) |
| | | | Cymel 303 (5%) | Cymel 303 (5%) | Cymel 303 (5%) | Cymel 303 (5%) |
| | Solvent | Dowanol | Dowanol | Dowanol | Dowanol | Dowanol |
| Processing | Drying Temp (C.) | 150 | 155 | 155 | 155 | 155 |
| Conditions | Drying Time (min) | 40 | 40 | 40 | 40 | 40 |
| | Layer Thickness | 7.1 | 6.1 | 6.2 | 6.3 | 6.1 |
| Electrical | Vr (V) | 209 | 90 | 63 | 91 | 70 |
| Properties | Dark Decay | 20 | 15 | 15 | 21 | 19 |
| (73 ms) | Vr(60-150) | 17 | 23 | N/A | 19 | N/A |
| | Vr(60-150) | 3 | 1 | N/A | 1 | N/A |
| Wear Rate | (nm/kcycle) | 37.1 | 45.2 | 64.1 | 48.7 | 29.4 |

The Table demonstrates that SOF photoreceptor overcoat layer compositions prepared from N,N,N',N'-tetrakis-[(4-hydroxymethyl)phenyl]-biphenyl-4,4'-diamine and N,N'-diphenyl-N,N-bis-(3-hydroxyphenyl)-terphenyl-4,4'-diamine (or N,N'-diphenyl-N,N'-bis-(3-hydroxyphenyl)-biphenyl-4,4'-diamine) molecular building blocks have been shown to be promising photoreceptor overcoat layer compositions for BCR-based charging systems. This SOF overcoat layer design has better electrical performance than a related cross-linked polymer design ($V_r$=90 V vs. 209 V). Further, the wear rate of this SOF overcoat layer design can be tuned (64 to 34 nm/kcycle) by simply changing the HTM ratio without negatively affecting the electrical performance of the photoreceptor device.

Example 7

(Action A) Attempted preparation of the liquid containing reaction mixture. The following were combined: the building block tris-[(4-hydroxymethyl)-phenyl]-amine [segment=tri-(p-tolyl)-amine; Fg=hydroxy (—OH); 5.12 g]; the additives Cymel303 (55 mg), Silclean 3700 (210 mg), and 1-methoxy-2-propanol (13.27 g). The mixture was heated to 55° C. for 65 min in an attempt to fully dissolve the molecular building block. However it did not fully dissolve. A catalyst Nacure XP-357 (267 mg) was added and the heterogeneous mixture was further mixed on a rolling wave rotator for 10 min. In this Example, the catalyst was added after the heating step. The solution was not filtered prior to coating due to the amount of undissolved molecular building block, (Action B) Deposition of reaction mixture as a wet film. The reaction mixture was applied to a commercially available, 30 mm drum photoreceptor using a cup coater (Tsukiage coating) at a pull-rate of 240 mm/min. (Action C) Promotion of the change of the wet film to a dry film. The photoreceptor drum supporting the wet layer was rapidly transferred to an actively vented oven preheated to 140° C. and left to heat for 40 min. These actions did not provide a uniform film. There were some regions where a non-uniform film formed that contained particles and other regions where no film was formed at all.

Example 8

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4'-diamine; Fg=hydroxy (—OH); 1.84 g] and the building block 3,3'-(4,4'-(biphenyl-4-ylazanediyl)bis(4,1-phenylene))dipropan-1-ol [segment=3,3'-(4,4'-(biphenyl-4-ylazanediyl)bis(4,1-phenylene))dipropyl; Fg=hydroxy (—OH); (2.41 g) and a catalyst p-toluenesulphonic acid (10 wt % solution in dowanol, 460 mg) and 1-methoxy-2-propanol (16.9 g—containing 50 ppm DC510). The mixture was mixed on a rolling wave rotator for 5 min and then heated at 70° C. for 30 min until a homogenous solution resulted. The mixture was placed on the rotator and cooled to room temperature. The solution was filtered through a 1 micron PTFE membrane. (Action B) The reaction mixture was applied to a production-coated web photoreceptor with a Hirano web coater. Syringe pump speed: 4.5 mL/min. (Action C) The photoreceptor supporting the wet layer was fed at a rate of 1.5 m/min into an actively vented oven preheated to 130° C. for 2 min. These actions provided a SOF overcoat layer having a thickness of 2.1 microns on a photoreceptor.

Example 9

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4"-diamine; Fg=hydroxy (—OH); 5.0 g] and the building block benzenedimethanol [segment=p-xylyl; Fg=hydroxyl (—OH); 2.32 g] and a catalyst p-toluenesulphonic acid (10 wt % solution in dowanol, 720 mg) and 1-methoxy-2-propanol (22.5 g—containing 50 ppm DC510). The mixture was mixed on a rolling wave rotator for 5 min and then heated at 40° C. for 5 min until a homogenous solution resulted. The mixture was placed on the rotator and cooled to room temperature. The solution was filtered through a 1 micron PIPE membrane. (Action B) The reaction mixture was applied to a production-coated, production web photoreceptor a Hirano web coater. Syringe pump speed: 5 mL/min. (Action C) The photoreceptor supporting the wet layer was fed at a rate of 1.5 m/min into an actively vented oven preheated to 130° C. for 2 min. These actions provided a SOF overcoat layer having a thickness of 2.2 microns on a photoreceptor.

Example 10

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4'-diamine; Fg=hydroxy (—OH); 5.0 g] and the building block benzenedimethanol [segment=p-xylyl; Fg=hydroxyl (—OH); 2.32 g] and a catalyst p-toluenesulphonic acid (10 wt % solution in dowanol, 720 mg) and 1-methoxy-2-propanol (22.5 g—containing 50 ppm DC510). The mixture was mixed on a rolling wave rotator for 5 min and then heated at 40° C. for 5 min until a homogenous solution resulted. The mixture was placed on the rotator and cooled to room temperature. The solution was filtered through a 1 micron PTFE membrane. (Action B) The reaction mixture was applied to a production-coated, production web photoreceptor with a Hirano web coater. Syringe pump speed: 10 mL/min. (Action C) The photoreceptor supporting the wet layer was fed at a rate of 1.5 m/min into an actively vented oven preheated to 130° C. for 2 min. These actions provided a SOF overcoat layer having a thickness of 4.3 microns on a photoreceptor.

The Examples below further demonstrate that SOP photoreceptor overcoat layer (OCL) compositions, such as, for example, those prepared from N,N,N',N'-tetrakis-[(4-hydroxymethyl)phenyl]-biphenyl-4,4'-diamine and N,N'-diphenyl-N,N'-bis-(3-hydroxyphenyl)-terphenyl-4,4'-diamine (or N,N'-diphenyl-N,N'-bis-(3-hydroxyphenyl)-biphenyl-4,4'-diamine) molecular building blocks are excellent OCL candidates for BCR-based charging systems.

Example 11

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4'-diamine; Fg=hydroxy (—OH); 4.11 g] and the building block N,N'-diphenyl-N,N'-bis-(3-hydroxyphenyl)-biphenyl-4,4'-diamine [segment=N,N,N',N'-tetraphenyl-biphenyl-4,4'-diamine; Fg=hydroxyl (—OH); 6.81 g]; the additives Cymel303 (585 mg) and Silclean 3700 (462 mg), and the catalyst Nacure XP-357 (581 mg) and 1-methoxy-2-propanol (32.60 g). The mixture was mixed on a rolling wave rotator for 60 min and filtered through a 1 micron PTFE membrane. (Action B) The reaction mixture was applied to a commercially available, 30 mm drum photoreceptor using a cup coater (Tsukiage coating) at a pull-rate of 230 mm/min. (Action C) The photoreceptor drum supporting the wet layer was rapidly transferred to an actively vented oven preheated to 155° C. and left to heat for 40 min. These actions provided a film having a thickness of 6.4 microns.

Example 12

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4'-diamine; Fg=hydroxy (—OH); 5.71 g] and the building block N,N'-diphenyl-N,N'-bis-(3-hydroxyphenyl)-biphenyl-4,4'-diamine [segment=N,N,N',N'-tetraphenyl-biphenyl-4,4'-diamine; Fg=hydroxyl (—OH); 9.46 g]; the additives Cymel303 (814 mg) and Silclean 3700 (660 mg), and the catalyst Nacure XP-357 (812 mg) and 1-methoxy-2-propanol (29.14 g). The mixture was mixed on a rolling wave rotator for 60 min and filtered through a 1 micron PTFE membrane. (Action B) The reaction mixture was applied to a commercially available, 30 mm drum photoreceptor using a cup coater (Tsukiage coating) at a pull-rate of 105 or 260 mm/min. (Action C) The photoreceptor drum supporting the wet layer was rapidly transferred to an actively vented oven preheated to 155° C. and left to heat for 40 min. These actions provided films having thickness of 10.1 and 14.5 microns.

Example 13

(Action A) The following were combined: the building block N,N,N',N'-tetrakis-[(4-hydroxymethyl)phenyl]-biphenyl-4,4'-diamine [segment N,N,N',N' tetra-(p-tolyl)biphenyl-4,4]-diamine; Fg=hydroxy (—OH); 4.43 and the building block N,N'-diphenyl-N,N'-bis-(3-hydroxyphenyl)-terphenyl-4,4'-diamine [segment=N,N,N',N'-tetraphenyl-terphenyl-4,4'-diamine; Fg=hydroxyl (—OH); 5.87 g]; the additives Cymel303 (554 mg) and Silclean 3700 (442 mg), and the catalyst Nacure XP-357 (554 mg) and 1-methoxy-2-propanol (34.34 g). The mixture was mixed on a rolling wave rotator for 10 min and then heated at 55° C. for 65 min until a homogenous solution resulted. The mixture was placed on the rotator and cooled to room temperature. The solution was filtered through a 1 micron PTFE membrane. (Action B) Deposition of reaction mixture as a wet film (first pass). The reaction mixture was applied to a commercially available, 30 mm drum photoreceptor using a cup coater (Tsukiage coating) at a pull-rate of 235 mm/min. (Action C) Promotion of the change of the wet film to a dry COF film (first pass). The photoreceptor drum supporting the wet layer was rapidly transferred to an actively vented oven preheated to 155° C. and left to heat for 5 min. (Action B2) Deposition of reaction mixture as a wet film (second pass). The reaction mixture was applied to a commercially available, 30 mm drum photoreceptor using a cup coater (Tsukiage coating) at a pull-rate of either 110 and 250 mm/min. (Action C2) Promotion of the change of the wet film to a dry COF film (second pass). The photoreceptor drum supporting the wet layer was rapidly transferred to an actively vented oven preheated to 155° C. and left to heat for 40 min. These actions provided a films having a thickness of 10.6 and 13.3 microns.

One-pass and two-pass SOF photoreceptor overcoat layers with thicknesses up to 15 microns have been prepared and been shown to have excellent electrical properties (Vr<100 V, stable short-term cycling) while maintaining other benefits observed for SOF OCLs (low BCR wear rate).

One-pass SOF OCLs were prepared using N,N,N',N'-tetrakis-[(4-hydroxymethyl)phenyl]-biphenyl-4,4'-diamine and N,N'-diphenyl-N,N'-bis-(3-hydroxyphenyl)-biphenyl-4,4'-diamine molecular building blocks. The solid content in the coating formulations and the coating pull rate may be varied to obtain the desired thicknesses, such as greater than 15 microns, or up to 30 microns.

Multi-pass SOF layers, such as two-pass (three-pass, four-pass, five pass, etc., layers) SOF OCLs may be prepared using N,N,N',N'-tetrakis-[(4-hydroxymethyl)phenyl]-biphenyl-4, 4'-diamine and N,N'-diphenyl-N,N'-bis-(3-hydroxyphenyl)-terphenyl-4,4'-diamine molecular building blocks or other molecular building blocks as desired. Optionally, a shortened heating step (such as 5 min instead of 40 min) may by used to partially cure the first pass before applying subsequent layers. Such thick, robust photoreceptor layers allow the lifetime of the device to be extended by around 1.5 to about 10 times and from around 2 to about 5 times using a thick layer while the wear rate may be increased from around 30 nm/kcycle to about 120 nm/kcycle and from around 35 nm/kcycle to about 65 nm/kcycle (BCR wear fixture) to obtain high image quality.

As demonstrated above, SOF photoreceptor overcoat layer (OCL) compositions prepared from N,N,N',N'-tetrakis-[(4-hydroxymethyl)phenyl]-biphenyl-4,4'-diamine and N,N'-diphenyl-N,N'-bis-(3-hydroxyphenyl)-terphenyl-4,4'-diamine (or N,N'-diphenyl-N,N'-bis-(3-hydroxyphenyl)-biphenyl-4,4'-diamine) molecular building blocks have been shown to be promising OCL candidates for BCR-based charging systems. SOF photoreceptor layers (CTL and/or OCL) comprising HTM loadings greater than 90% have excellent electrical performance (low Vr, stable cycling) for layers thicker than 10 μm.

Example 14

(Action A) The following were combined: the building block N,N,N'N'-tetrakis-[(4-hydroxymethyl)phenyl]-biphenyl-4,4'-diamine [segment=N,N,N',N'-tetra-(p-tolyl)biphenyl-4,4'-diamine; Fg=hydroxy (—OH); in the amounts listed in Table 2] and the capping unit as designated in Table 2, except Test 10 (which did not include a capping unit; the additive Silclean 3700, and the catalyst Nacure XP-357 and dowanol. The mixture was mixed on a rolling wave rotator for 10 min and then heated at 65° C. for 60 min until a homogenous solution resulted. The mixture was placed on the rotator and cooled to room temperature. The solution was filtered through a 1 micron PTFE membrane. (Action B) The reaction mixture was applied to an aluminum substrate. (Action C) The aluminum substrate supporting the wet layer was rapidly transferred to an actively vented oven preheated to 140° C. and left to heat for 40 min. These actions provided a film having a thickness ranging from 4 to 10 microns.

TABLE 2

Capped SOF formulations

| Test # | Building Block 1 | Capping Unit | Additive | Solvent | Catalyst | Gap | Notes |
|---|---|---|---|---|---|---|---|
| 1 Mass (g) | N,N,N',N'-tetrakis-[(4-hydroxymethyl)phenyl]-biphenyl-4,4'-diamine 0.3474 | 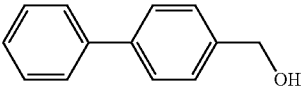<br>Biphenyl-4-methanol<br>0.0526 | Silclean 3700 0.0200 | dowanol 1.5600 | 2% Nacure XP357 0.02 | 10 mil | 1.5 Molar Ratio of Capping Unit: Building Block |
| 2 Mass (g) | N,N,N',N'-tetrakis-[(4-hydroxymethyl)phenyl]-biphenyl-4,4'-diamine 0.2751 | 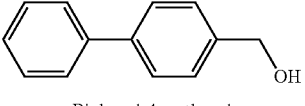<br>Biphenyl-4-methanol<br>0.1249 | Silclean 3700 0.0200 | dowanol 1.5600 | 2% Nacure XP357 0.02 | 10 mil | 0.5 Molar Ratio of Capping Unit: Building Block |
| 3 Mass (g) | N,N,N',N'-tetrakis-[(4-hydroxymethyl)phenyl]-biphenyl-4,4'-diamine 0.3262 | 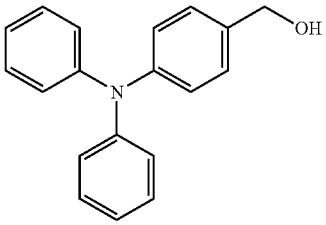<br>(4-(diphenylamino)phenyl)methanol<br>0.0738 | Silclean 3700 0.0200 | dowanol 1.5600 | 2% Nacure XP357 0.02 | 10 mil | 1.5 Molar Ratio of Capping Unit: Building Block |
| 4 Mass (g) | N,N,N',N'-tetrakis-[(4-hydroxymethyl)phenyl]-biphenyl-4,4'-diamine 0.2383 | 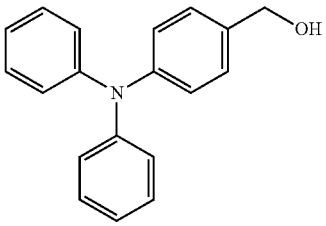<br>(4-(diphenylamino)phenyl)methanol<br>0.1617 | Silclean 3700 0.0200 | dowanol 1.5600 | 2% Nacure XP357 0.02 | 10 mil | 0.5 Molar Ratio of Capping Unit: Building Block |

TABLE 2-continued

Capped SOF formulations

| Test # | Building Block 1 | Capping Unit | Additive | Solvent | Catalyst | Gap | Notes |
|---|---|---|---|---|---|---|---|
| 5 | N,N,N',N'-tetrakis-[(4-hydroxymethyl)phenyl]-biphenyl-4,4'-diamine 0.3295 | triphenylmethanol 0.0705 | Silclean 3700 0.0200 | dowanol 1.5600 | 2% Nacure XP357 0.02 | 10 mil | 1.5 Molar Ratio of Capping Unit: Building Block |
| 6 | N,N,N',N'-tetrakis-[(4-hydroxymethyl)phenyl]-biphenyl-4,4'-diamine 0.2437 | triphenylmethanol 0.1563 | Silclean 3700 0.0200 | dowanol 1.5600 | 2% Nacure XP357 0.02 | 10 mil | 0.5 Molar Ratio of Capping Unit: Building Block |
| 7 | N,N,N',N'-tetrakis-[(4-hydroxymethyl)phenyl]-biphenyl-4,4'-diamine 0.3519 | adamantane-1-methanol 0.0481 | Silclean 3700 0.0200 | dowanol 1.5600 | 2% Nacure XP357 0.02 | 10 mil | 0.5 Molar Ratio of Capping Unit: Building Block |
| 8 | N,N,N',N'-tetrakis-[(4-hydroxymethyl)phenyl]-biphenyl-4,4'-diamine 0.3635 | 4-methylbenzyl alcohol 0.0365 | Silclean 3700 0.0200 | dowanol 1.5600 | 2% Nacure XP357 0.02 | 10 mil | 0.5 Molar Ratio of Capping Unit: Building Block |
| 9 | N,N,N',N'-tetrakis-[(4-hydroxymethyl)phenyl]-biphenyl-4,4'-diamine 0.3262 | 3-(phenyl(p-tolyl)amino)phenol 0.0738 | Silclean 3700 0.0200 | dowanol 1.5600 | 2% Nacure XP357 0.02 | 10 mil | 0.5 Molar Ratio of Capping Unit: Building Block |

All of the above formulations produced pinhole-free SOFs from visual inspection. FT-IR spectroscopy of the SOF demonstrated that the linking between N,N,N',N'-tetrakis-[(4-hydroxymethyl)phenyl]-biphenyl-4,4'-diamine building blocks and capping units was successful and efficient since —OH bands detected in the films were strongly attenuated or completely absent.

Figure 8:
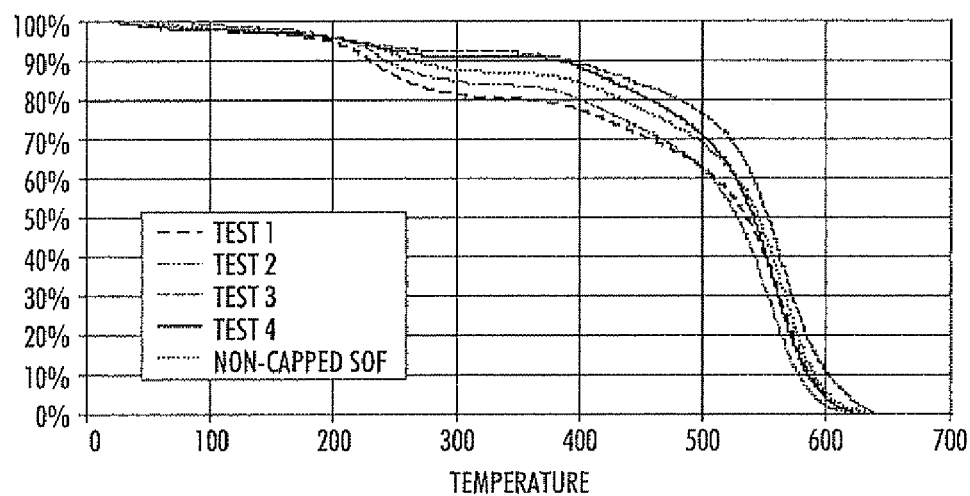
FIG. 8 is a graphic representation of TGA curves for capped SOFs versus a non-capped SOF.

The thermal stability of the capped SOFs is comparable to that of the N,N,N',N'-tetrakis-[(4-hydroxymethyl)phenyl]-biphenyl-4,4'-diamine SOF without capping units. FIG. 8 demonstrates that no decomposition observed until 400° C., which is indicative of a highly-linked material.

Mechanical properties of films were strongly affected by the introduction of capping units. The mechanical properties of capped SOF films were assessed by collecting stress-strain data for the free standing films (FIG. 9) of the above capped SOF films and other capped SOF films. In general, SOF films containing capping units had greater toughness and a less-linear stress-strain curve compared to the pure SOF film constructed only from N,N,N',N'-tetrakis-[(4-hydroxymethyl)phenyl]-biphenyl-4,4'-diamine. The above mechanical data clearly that the change at the microscopic level attained through introduction of capping units into SOFs has a direct effect on the macroscopic properties of the film.

Example 15

(Action A) The following were combined: the building block N,N,N',N'-tetrakis-[(4-hydroxymethyl)phenyl]-biphenyl-4,4'-diamine [segment=N,N,N',N'-tetra-(p-tolyl)biphenyl-4,4'-diamine; Fg=hydroxy (—OH); in the amounts listed in Tables 3-6] and the capping unit, the additive Silclean 3700, the catalyst Nacure XP-357 and Dowanol (as designated in Table 3-6). The mixture was mixed on a rolling wave rotator for 10 min and then heated at 65° C. for 60 min until a homogenous solution resulted. The mixture was placed on the rotator and cooled to room temperature. The solution was filtered through a 1 micron PTFE membrane. (Action B) The reaction mixture was applied to a commercially available, 30 mm drum photoreceptor using a cup coater (Tsukiage coating) at a pull-rate of 485 mm/min. (Action C) The photoreceptor drum supporting the wet layer was rapidly transferred to an actively vented oven preheated to 140° C. and left to heat for 40 min. These actions provided a film having a thickness ranging from 6 to 7 microns.

TABLE 3

Test 11 - low biphenyl-4-methanol loading (12 wt %, 4.5 mmol)

| Type | Building Block | Cap Unit | Curing | Catalyst | Additive | Solvent | % Solid Content |
|---|---|---|---|---|---|---|---|
| Compound | N,N,N',N'-tetrakis-[(4-hydroxymethyl)-phenyl]-biphenyl-4,4'-diamine | biphenyl-4-methanol | Cymel 303 | Nacure XP-357 | Silclean 3700 | Dowanol PM | 28.0% |
| % Active | 1.00 | 1.00 | 1.00 | 0.20 | 0.25 | 0.00 | Total Mass |
| Total weight (gr.) | 3.6856 | 0.5461 | 0.2275 | 0.2264 | 0.1815 | 11.4000 | 16.2671 |
| Active weight (gr.) | 3.69 | 0.55 | 0.23 | 0.05 | 0.05 | 0.00 | Scaling Factor |
| Percent weight (%) | 81.00% | 12.00% | 5.00% | 1.00% | 1.00% | 0.00% | 1.50 |
| Scaled weight (gr.) | 5.5284 | 0.8192 | 0.3413 | 0.3396 | 0.2723 | 17.1000 | 24.4007 |
| Actual weight (gr.) | 5.5290 | 0.8189 | 0.3434 | 0.3408 | 0.2744 | 17.1096 | 24.4161 |

TABLE 4

Test 12 - high biphenyl-4-methanol loading (30 wt %, 11 mmol)

| Type | Building Block | Cap Unit | Curing | Catalyst | Additive | Solvent | % Solid Content |
|---|---|---|---|---|---|---|---|
| Compound | N,N,N',N'-tetrakis-[(4-hydroxymethyl)-phenyl]-biphenyl-4,4'-diamine | biphenyl-4-methanol | Cymel 303 | Nacure XP-357 | Silclean 3700 | Dowanol PM | 28.0% |
| % Active | 1.00 | 1.00 | 1.00 | 0.20 | 0.25 | 0.00 | Total Mass |
| Total weight (gr.) | 2.8668 | 1.3652 | 0.2275 | 0.2264 | 0.1815 | 11.4000 | 16.2674 |
| Active weight (gr.) | 2.87 | 1.37 | 0.23 | 0.05 | 0.05 | 0.00 | Scaling Factor |
| Percent weight (%) | 63.00% | 30.00% | 5.00% | 1.00% | 1.00% | 0.00% | 1.50 |
| Scaled weight (gr.) | 4.3002 | 2.0478 | 0.3413 | 0.3396 | 0.2723 | 17.1000 | 24.4011 |
| Actual weight (gr.) | 4.3001 | 2.0485 | 0.3444 | 0.3330 | 0.2712 | 17.1078 | 24.4050 |

TABLE 5

Test 13 - low (4-(diphenylamino)phenyl)methanol loading (17 wt %, 4.5 mmol)

| Type | Building Block | Cap Unit | Curing | Catalyst | Additive | Solvent | % Solid Content |
|---|---|---|---|---|---|---|---|
| Compound | N,N,N',N'-tetrakis-[(4-hydroxymethyl)-phenyl]-biphenyl-4,4'-diamine | (4-(diphenylamino)-phenyl)methanol | Cymel 303 | Nacure XP-357 | Silclean 3700 | Dowanol PM | 28.0% |
| % Active | 1.00 | 1.00 | 1.00 | 0.20 | 0.25 | 0.00 | Total Mass |
| Total weight (gr.) | 3.4581 | 0.7736 | 0.2275 | 0.2264 | 0.1815 | 11.4000 | 16.2671 |
| Active weight (gr.) | 3.46 | 0.77 | 0.23 | 0.05 | 0.05 | 0.00 | Scaling Factor |
| Percent weight (%) | 76.00% | 17.00% | 5.00% | 1.00% | 1.00% | 0.00% | 1.50 |
| Scaled weight (gr.) | 5.1872 | 1.1604 | 0.3413 | 0.3396 | 0.2723 | 17.1000 | 24.4007 |
| Actual weight (gr.) | 5.1869 | 1.1603 | 0.3407 | 0.3390 | 0.2710 | 17.0993 | 24.3972 |

TABLE 6

Test 14 - high (4-(diphenylamino)phenyl)methanol loading (37 wt %, 11 mmol)

| Type | Building Block | Cap Unit | Curing | Catalyst | Additive | Solvent | % Solid Content |
|---|---|---|---|---|---|---|---|
| Compound | N,N,N',N'-tetrakis-[(4-hydroxymethyl)phenyl]-biphenyl-4,4'-diamine | (4-(diphenylamino)phenyl)-methanol | Cymel 303 | Nacure XP-357 | Silclean 3700 | Dowanol PM | 28.0% |
| % Active | 1.00 | 1.00 | 1.00 | 0.20 | 0.25 | 0.00 | Total Mass |
| Total weight (gr.) | 2.5483 | 1.6837 | 0.2275 | 0.2264 | 0.1815 | 11.4000 | 16.2674 |
| Active weight (gr.) | 2.55 | 1.68 | 0.23 | 0.05 | 0.05 | 0.00 | Scaling Factor |
| Percent weight (%) | 56.00% | 37.00% | 5.00% | 1.00% | 1.00% | 0.00% | 1.50 |
| Scaled weight (gr.) | 3.8225 | 2.5256 | 0.3413 | 0.3396 | 0.2723 | 17.1000 | 24.4011 |
| Actual weight (gr.) | 3.8227 | 2.5270 | 0.3413 | 0.3405 | 0.2716 | 17.1024 | 24.4055 |

Figure 10:
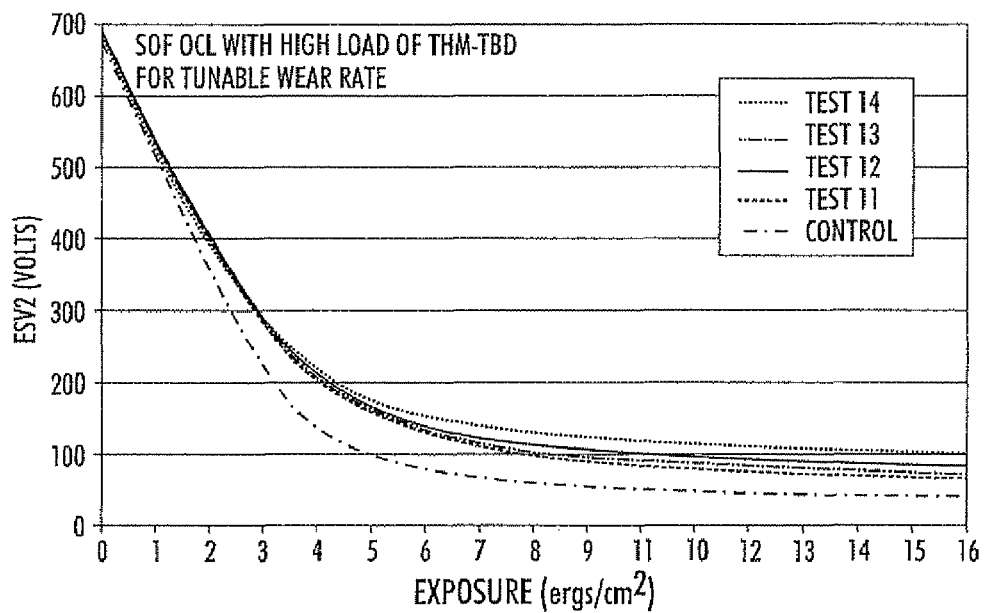
FIG. 10 is a graphic representation of a photo-induced discharge curve (PIDC) illustrating the photoconductivity of a various overcoat layers.
Figure 11:
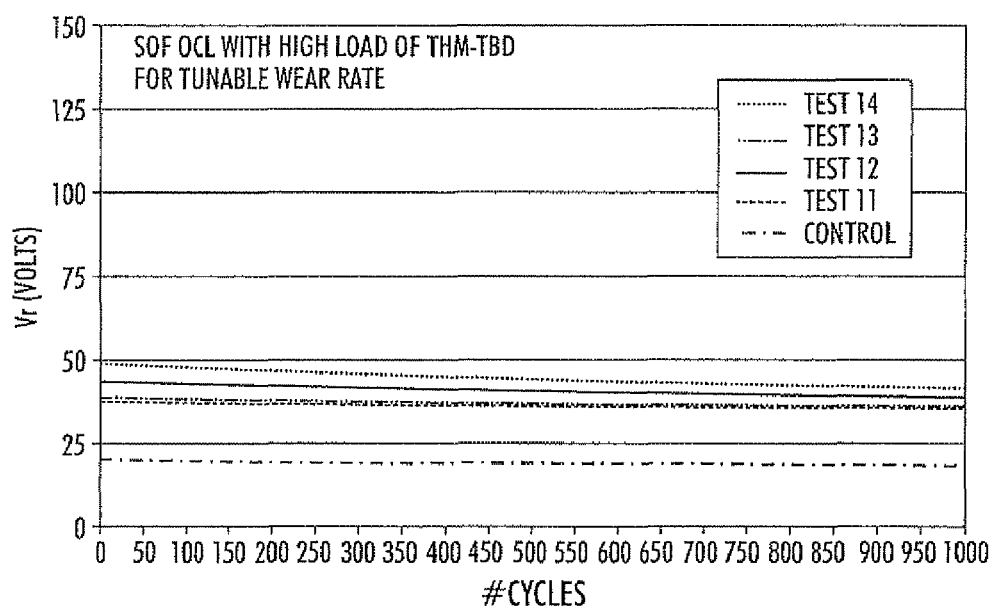
FIG. 11 is a graphic representation of cycling data that was acquired for various overcoat layers.

All of the above formulations produced pinhole-free SOFs from visual inspection. FT-IR spectroscopy of the SOF demonstrated that the linking between N,N,N',N'-tetrakis-[(4-hydroxymethyl)phenyl]-biphenyl-4,4'-diamine building blocks and capping units was successful and efficient since —OH bands detected in the films were strongly attenuated or completely absent. FIG. 10 is a photo-induced discharge curve (PIDC) illustrating the photoconductivity of a capped SOF overcoat layer (voltage at 75 ms (expose-to-measure)). The electrical properties of the devices are excellent (low Vr and no cycle up). See PIDCs and cycling data in FIGS. 10 and 11, respectively.

BCR wear data for capped SOF OCLs shows (for both types of capping units) higher wear rates with respect to capping unit loading (Table 7, below). Conventional charge transport layers suffer from a fast, nearly catastrophic wear rate of 8 to 10 microns or more per 100 kilocycles when the photoreceptor is charged using a bias charging roll (BCR), such as an AC BCR. The use of AC bias charging rolls to charge a photoreceptor surface is conventional in the art for forming images in low speed, for example up to 40 ppm, imaging devices (e.g., copiers and printers). However, the corona generated from the AC current, applied to the BCR, decomposes on the top photoreceptor layer. The decomposed material can be easily removed by a cleaning blade. Such a repeated process during the printing cycle wears out the photoreceptor top layer very quickly.

Wear rate is a significant property in that it limits the life of the photoreceptor, and photoreceptor replacement in electrostatographic devices such as copiers and printers is very expensive. It is thus very significant to control wear of the photoreceptor so as to achieve a long life photoreceptor, particularly with respect to small diameter organic photoreceptor drums typically used in low speed copiers and printers that are charged with an AC BCR. In such small diameter drums, 100 kilocycles translates into as few as 10,000 prints. CTL wear results in a considerable reduction in device sensitivity, which is a major problem in office copiers and printers that typically do not employ exposure control. In addition, the rapid wear of the top photoreceptor layer requires better cleaning of the debris from the photoreceptor surface in order to maintain good toner transfer and good copy quality. The wear magnitude and difference between high and low loadings is small, indicating that considerable latitude exists to increase wear rates by further increasing capping unit loading, which would also lower the amount (and cost) of required HTM.

TABLE 7

BCR wear data for capped SOF Photoreceptor Overcoat Layers

| | Curing: 40 minutes | SOF overcoat | BCR Wear |
|---|---|---|---|
| Sample | (μm) | (μm) | nm/kcycle | mg/kcycle |
| Test 14 | 5.7 | 0.9 | 18.4 | 3006 |
| Test 13 | 5.7 | 1.0 | 20.4 | 3192 |
| Test 12 | 7.3 | 1.2 | 24.2 | 2986 |
| Test 11 | 6.6 | 1.4 | 28.8 | 3095 |

Print tests present no print quality issues and are essentially identical to non-overcoated P/R devices.

It will be appreciated that several of the above-disclosed and other features and functions, or alternatives thereof, may be desirably combined into many other different systems or applications. Various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A structured organic film (SOF) comprising a plurality of segments, a plurality of linkers arranged as a covalent organic framework (COF), wherein the framework of the SOF comprises a capping unit bonded to the framework of the SOF via a linker group.

2. The SOF of claim 1, wherein the linker group is a covalent bond linker or a chemical moiety linker.

3. The SOF of claim 1, wherein the capping unit is bonded to at least 1% of the segments of the SOF.

4. The SOF of claim 1, wherein the capping unit is bonded to substantially all the segments of the SOF.

5. The SOF of claim 1, wherein the capping unit is distributed randomly within the SOF.

6. The SOF of claim 1, wherein the capping unit is distributed in a non-uniformly within the SOF.

7. The SOF of claim 1, wherein the capping unit comprises chemical moieties or functional groups that are not bonded to any segments.

8. The SOF of claim 1, wherein the capping unit enhances an inclined or inherent property of the SOF.

9. The SOF of claim 1, wherein the capping unit attenuates an inclined or inherent property of the SOF.

10. The SOF of claim 1, wherein the capping unit comprises a first capping unit and a second capping unit and the first capping unit's structure is different from the structure of the second capping unit.

11. The SOF of claim 1, wherein the SOF is a substantially pinhole-free film.

12. The SOF of claim 1, wherein the plurality of segments consists of segments having an identical structure and the plurality of linkers consists of linkers having an identical structure, wherein the segments that are neither at the edges of the SOF nor bonded to the capping unit are connected by linkers to at least three other segments.

13. The SOF of claim 1, wherein the SOF is a composite SOF.

14. The SOF of claim 1, wherein the SOF has the added functionality of electro activity.

15. The SOF of claim 1, wherein the rupture point of the SOF is enhanced from about 80% to about 200%.

16. The SOF of claim 1, wherein the rupture point of the SOF is attenuated from about 10% to about 50%.

17. A process for preparing a capped structured organic film, comprising:
(a) preparing a liquid-containing reaction mixture comprising:
a plurality of molecular building blocks each comprising a segment and a number of functional groups, and
a capping unit molecule;
(b) depositing the reaction mixture as a wet film; and
(c) promoting change of the wet film to form a dry SOF with capping units bonded within the SOF.

18. The process of claim 17, wherein the capping unit molecule comprises a single functional group that participates in a chemical reaction to link the capping unit molecule to the segment via a linker during the promoting change of the wet film to form a dry SOF.

19. The process of claim 17, wherein the capping unit molecule comprises one or more chemical moieties or functional groups that do not participate in a chemical reaction to link the capping unit molecule to the segment during the promoting change of the wet film to form a dry SOF.

20. The process of claim 17, wherein the SOF has the added functionality of electro activity.

21. The process of claim 17, wherein the dry SOF comprises a plurality of segments including at least a first segment type, a plurality of linkers including at least a first linker type arranged as a covalent organic framework (COF), wherein the first segment type and/or the first linker type comprises at least one atom that is not carbon.

22. The SOF of claim 1, wherein the SOF is a mono-segment thick layer with a thickness of from about 10 Angstroms to about 250 Angstroms; or the SOF is a multi-segment thick layer with a thickness of from about 20 nm to about 5 mm.

23. A structured organic film (SOF) comprising a plurality of segments including at least a first segment type and a plurality of linkers including at least a first linker type arranged as a covalent organic framework (COF), wherein
the first segment type and/or the first linker type comprises at least one atom that is not carbon, and
the framework of the SOF comprises a capping unit bonded to the framework of the SOF via a linker group.

24. The SOF of claim 23, wherein the at least one atom of an element that is not carbon is selected from the group consisting of hydrogen, oxygen, nitrogen, silicon, phosphorous, selenium, fluorine, boron, and sulfur.

25. A structured organic film (SOF) comprising a plurality of segments including at least a first segment type and a plurality of linkers including at least a first linker type arranged as a covalent organic framework (COF), wherein the SOF is a substantially defect-free film, and the first segment type and/or the first linker type comprises a hydrogen, and the framework of the SOF comprises a capping unit bonded to the framework of the SOF via a linker group.

26. The SOF of claim 25, wherein the SOF is a mono-segment thick layer with a thickness of from about 10 Angstroms to about 250 Angstroms; or the SOF is a multi-segment thick layer with a thickness of from about 20 nm to about 5 mm.

27. The SOF of claim 25, wherein the plurality of segments comprises at least the first segment type comprising a hydrogen atom and a second segment type that is structurally different from the first segment type.

28. The SOF of claim 25, wherein the plurality of linkers comprises at least the first linker type comprising a hydrogen and a second linker type that is structurally different from the first linker type.

29. The SOF of claim 25, wherein the plurality of segments have a core selected from the group consisting of carbon, nitrogen, silicon, or phosphorous atomic cores, alkoxy cores, aryl cores, carbonate cores, carbocyclic cores, carbobicyclic cores, carbotricyclic cores, and oligothiophene cores; or the plurality of linkers are selected from the group consisting of single atom linkers, single covalent bond linkers, and double covalent bond linkers, ester linkers, ketone linkers, amide linkers, amine linkers, imine linkers, ether linkers, urethane linkers, and carbonates linkers.

30. The SOF of claim 25, wherein the plurality of segments and/or the plurality of linkers comprises at least one atom selected from the group consisting of oxygen, nitrogen, silicon, phosphorous, selenium, fluorine, boron, and sulfur.

* * * * *